US008722622B2

(12) United States Patent
Das et al.

(10) Patent No.: US 8,722,622 B2
(45) Date of Patent: May 13, 2014

(54) FGF21 CONJUGATES AND ANTI-DIABETIC USES THEREOF

(75) Inventors: Tapan Kanti Das, Ballwin, MO (US); Tamara Shafer Hodge, Ballwin, MO (US); Tetsuya Ishino, Boston, MA (US); Nancy Jane Levin, Encinitas, CA (US); Moorthy Sitharamaiah Suriyanarayana Palanki, Encinitas, CA (US); Erin Kristen Parsons, University City, MO (US); Bernard Norman Violand, Wildwood, MO (US)

(73) Assignees: COVX Technologies Ireland, Limited, Dun Laoghaire, County Dublin (IE); Pfizer Inc., New York, NY (US)

( * ) Notice: Subject to any disclaimer, the term of this patent is extended or adjusted under 35 U.S.C. 154(b) by 0 days.

(21) Appl. No.: 13/289,533

(22) Filed: Nov. 4, 2011

(65) Prior Publication Data

US 2012/0282279 A1 Nov. 8, 2012

Related U.S. Application Data

(60) Provisional application No. 61/410,715, filed on Nov. 5, 2010.

(51) Int. Cl.
*A61K 38/18* (2006.01)
*A61K 39/395* (2006.01)

(52) U.S. Cl.
USPC .......................................... 514/9.1; 424/179.1

(58) Field of Classification Search
None
See application file for complete search history.

(56) References Cited

U.S. PATENT DOCUMENTS

| | | | |
|---|---|---|---|
| 5,985,626 A | 11/1999 | Barbas et al. | |
| 6,210,938 B1 | 4/2001 | Barbas et al. | |
| 6,309,881 B2 | 10/2001 | Barbas et al. | |
| 6,326,176 B1 | 12/2001 | Barbas et al. | |
| 6,368,839 B1 | 4/2002 | Barbas et al. | |
| 6,589,766 B1 | 7/2003 | Barbas et al. | |
| 6,716,626 B1 | 4/2004 | Itoh et al. | |
| 7,408,047 B1 | 8/2008 | Thomason et al. | |
| 7,491,697 B2 | 2/2009 | Beals et al. | |
| 7,521,425 B2 | 4/2009 | Bradshaw et al. | |
| 7,576,190 B2 | 8/2009 | Glaesner et al. | |
| 7,582,607 B2 | 9/2009 | Frye et al. | |
| 7,622,445 B2 | 11/2009 | Frye et al. | |
| 7,655,627 B2 | 2/2010 | Frye et al. | |
| 8,012,931 B2 | 9/2011 | Cujec et al. | |
| 8,034,770 B2 | 10/2011 | Belouski et al. | |
| 8,383,365 B2* | 2/2013 | Cujec et al. | 435/69.1 |
| 2003/0175921 A1 | 9/2003 | Barbas et al. | |
| 2007/0265200 A1 | 11/2007 | Glaesner et al. | |
| 2008/0166364 A1 | 7/2008 | Bradshaw et al. | |
| 2008/0176790 A1 | 7/2008 | DeFrees | |
| 2008/0261875 A1 | 10/2008 | Etgen et al. | |
| 2009/0098130 A1* | 4/2009 | Bradshaw et al. | 424/139.1 |
| 2009/0111742 A1 | 4/2009 | Kharitonenkov et al. | |
| 2011/0104152 A1* | 5/2011 | Sonoda | 424/133.1 |

FOREIGN PATENT DOCUMENTS

| | | |
|---|---|---|
| WO | WO03059270 | 7/2003 |
| WO | WO2010065439 | 6/2010 |
| WO | WO 2010/129600 A2 | 11/2010 |
| WO | WO2012007896 | 1/2012 |

OTHER PUBLICATIONS

Barbas, C.F., et al., "Immune Versus Natural Selection: Antibody Aldolases with Enzymic Rates But Broader Scope," Sciencemag.org, 1997, 2085-2092, vol. 278.
Doppalapudi, V.R., et al., "Chemically programmed antibodies: Endothelin receptor targeting CovX-Bodies™," Bioorganic and Medicinal Chemistry Letters, 2007, 501-506, vol. 17, No. 2.
Huang, H., et al., "Angiopoietin-2 antagonistic CovX-BodyTM inhibits tumor growth and reduces microvessel density," Proceedings of the Annual Meeting of the American Association for Cancer Research, 2007, 509, col. 48, No. XP001536926.
Murphy, R.E., et al., "Combined use of immunoassay and two-dimensional liquid chromatography mass spectrometry for the detection and identification of metabolites from biotherapeutic pharmacokinetic samples," Journal of Pharmaceutical and Biomedical Analysis, 2010, 221-227, vol. 53, No. 3.
Rader, C., et al., "A Humanized Aldolase Antibody for Selective Chemotherapy and Adaptor Immunotherapy," Journal of Molecular Biology, 2003, 889-899, vol. 332.
Rosen, L. S., et al., "First-In-Human-Dose-Escalation Safety and PK Trial of a Novel Intravenous Humanized Monoclonal CovX Body Inhibiting Angiopoietin 2," Journal of Clinical Oncology, 2010, 2524, vol. 28, No. 15.

* cited by examiner

*Primary Examiner* — Christine J Saoud
(74) *Attorney, Agent, or Firm* — Wendy L. Hsu

(57) ABSTRACT

The present invention provides a FGF21 molecule covalently attached to the combining site of an antibody via a linker, wherein the linker is covalently attached to the side chain of a linking residue within FGF21. Various uses of the compounds are provided, including methods to prevent or treat diabetes or diabetes-related conditions.

21 Claims, 25 Drawing Sheets

```
                    Fr1                           CDR1                    FR2                CDR2              FR3                                      CDR3            FR4
                             1         2           3                       4          5             6          7          8                      9          1
       12345678901234567890123  4567890¹abcde234  567890123456789  0123456  7890123456789012345678  901234567  8901234567
m38c2  DVVMTQTPLSLPVRLGDQASISC  RSSQSLLHTYGSPYLN  WYLQKPGQSPKLLIY  KVSNRFS  GVPDRFSGGSGTDFTLRISRVEAEDLGVYFC  SQGTHLPYT  FGGGTKLEIK
       ***    ****    ***  *     *        *           *    **       ** ***           *    ****  **             * ****        *
h38c2  ELQMTQSPSSLSASVGDRVTITC  RSSQSLLHTYGSPYLN  WYLQKPGQSPKLLIY  KVSNRFS  GVPSRFSGSGSGTDFTLTISSLQPEDFAVYFC  SQGTHLPYT  FGGGTKVEIK
        **                      ********                                                                     * *****  *
DPK-9  DIQMTQSPSSLSASVGDRVTITC  RASQSISS-----YLN  WYQQKPGKAPKLLIY  AASSLQS  GVPSRFSGSGSGTDFTLTISSLQPEDFATYYC  QQSYSTP
JK4                                                                                                                   LT  FGGGTKVEIK
```

VH

```
                   FR1                          CDR1        FR2                   CDR2                       FR3                                              CDR3              FR4
                            1         2          3                   4          5          6          7          8                                        9      1          1
       1234567890123456789012345678901ab2345  6789012345678  9  012abc345678901234567  67890123456789012abc345678901234  5678901  2  345678901234567
m38c2  EVKLVESGGGLVQPGGTMKLSCEISGLTFR  N--YWMS  WVRQSPEKGLEWVA  EIRLRSDNYATHYAESVKG  KFTISRDDSKSRLYLQMNSLRTEETGIYYCKY  YFY-SFSY  WGQGTLVTVSA
           *           ***  *  *    *       *                   *                     *       *                           *                            *
h38c2  EVQLVESGGGLVQPGGSLRLSCAASGFTFS  N--YWMS  WVRQSPEKGLEWVS  EIRLRSDNYATHYAESVKG  RFTISRDNSKNTLYLQMNSLRAEDTGIYYCKT  YFY-SFSY  WGQGTLVTVSS
           *           **  * * *      *                            **                  *   ****  *                        **   **
DP-47  EVQLLESGGGLVQPGGSLRLSCAASGFTFS  S---YAMS  WVRQAPGKGLEWVS  AISG--SGGSTYYADSVKG  RFTISRDNSKNTLYLQMNSLRAEDTAVYYCAK
JH4                                                                                                                                                         YFDY  WGQGTLVTVSS
```

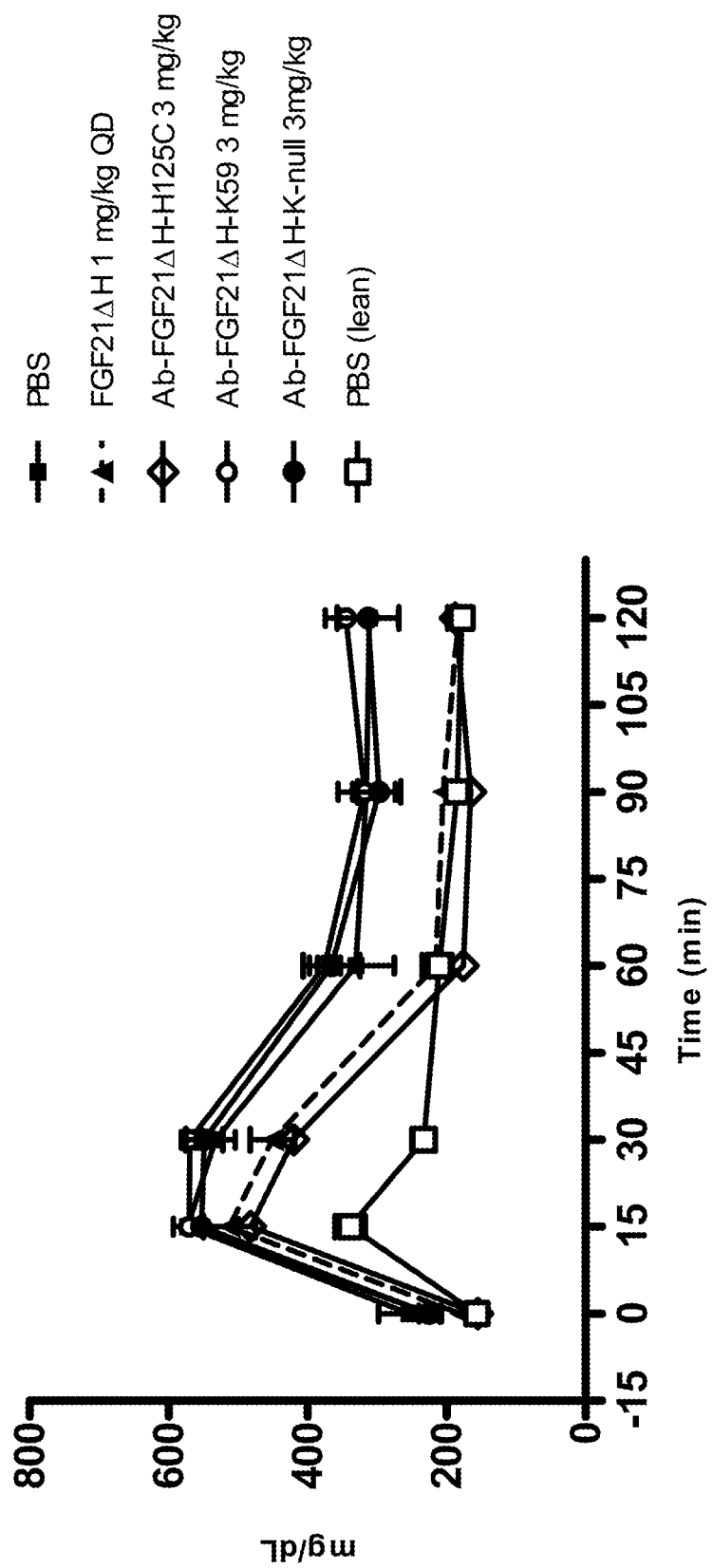

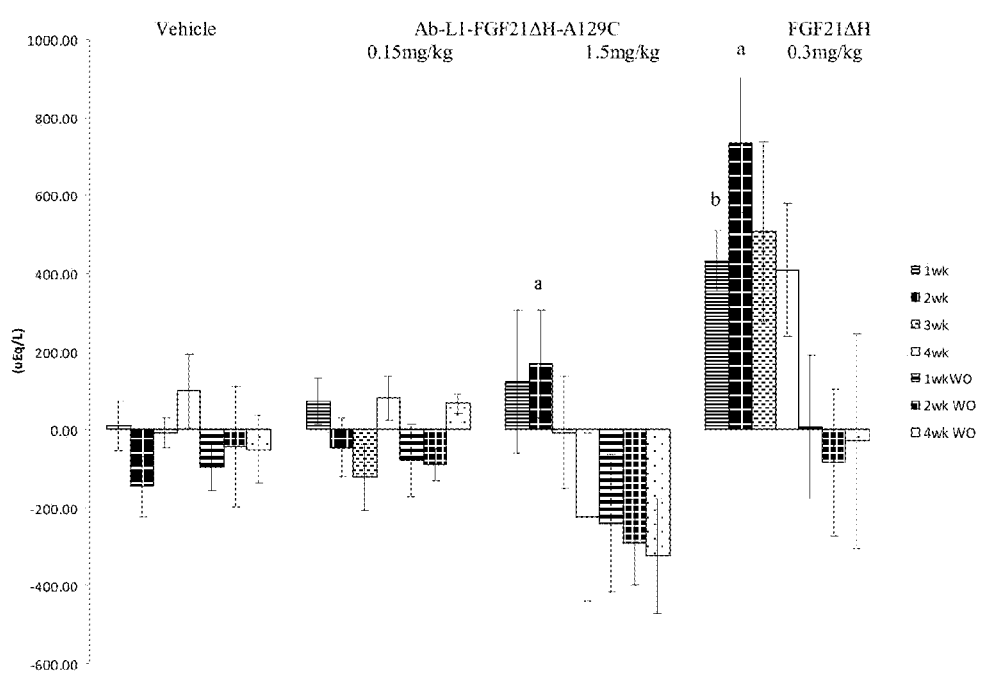

FGF21 CONJUGATES AND ANTI-DIABETIC USES THEREOF

REFERENCE TO RELATED APPLICATIONS

This application claims the benefit of U.S. Provisional Application No. 61/410,715, filed Nov. 5, 2010, which is incorporated herein by reference in its entirety.

REFERENCE TO SEQUENCE LISTING

This application is being filed electronically via EFS-Web and includes an electronically submitted sequence listing in .txt format. The .txt file contains a sequence listing entitled "PC71671A_Seq_List_ST25.txt" created on Nov. 3, 2011 and having a size of 52 KB. The sequence listing contained in the .txt file is part of the specification and is herein incorporated by reference in its entirety. This application includes an electronically submitted amended sequence listing in .txt format. The .txt file contains a sequence listing entitled "PC71671ASeqListAmended.txt" created on Sep. 17, 2012 and having a size of 52KB. The amended sequence listing contained in this .txt file is part of the specification and is herein incorporated by reference in its entirety.

FIELD OF THE INVENTION

The present invention relates to novel compounds that promote insulin secretion and lower blood glucose levels, and methods of making and using these compounds.

BACKGROUND

Type II diabetes is the most prevalent form of diabetes. The disease is caused by insulin resistance and pancreatic β cell failure, which results in decreased glucose-stimulated insulin secretion. Fibroblast growth factor (FGF) 21, a member of the FGF family, has been identified as a metabolic regulator and is preferentially expressed in the liver and adipose tissue and exerts its biological activities through the cell surface receptor composed of FGFR1c and β-Klotho on target cells such as liver and adipose tissues (WO0136640, and WO0118172). The receptor complex is thought to trigger cytoplasmic signaling and to up-regulate the GLUT1 expression through the Ras/MAP kinase pathway. Its abilities to provide sustained glucose and lipid control, and improve insulin sensitivity and β-cell function, without causing any apparent adverse effects in preclinical settings, have made FGF21 an attractive therapeutic agent for type-2 diabetes and associated metabolic disorders.

There have been a number of efforts towards developing therapies based on FGF21. WO2006065582, WO2006028714, WO2006028595, and WO2005061712 relate to muteins of FGF21, comprising individual amino-acid substitutions. WO2006078463 is directed towards a method of treating cardiovascular disease using FGF21. WO2005072769 relates to methods of treating diabetes using combinations of FGF21 and thiazolidinedione. WO03059270 relates to methods of reducing the mortality of critically ill patients comprising administering FGF21. WO03011213 relates to a method of treating diabetes and obesity comprising administering FGF21.

However, many of these proposed therapies suffer from the problem that FGF21 has an in-vivo half-life of between 1.5 and 2 hrs in humans. Some attempts have been made to overcome this drawback. WO2005091944, WO2006050247 and WO2008121563 disclose FGF21 molecules linked to PEG via lysine or cysteine residues, glycosyl groups and non-natural amino acid residues, respectively. WO2005113606 describes FGF21 molecules recombinantly fused via their C-terminus to albumin and immunoglobulin molecules using polyglycine linkers. However, developing protein conjugates into useful, cost-effective pharmaceuticals presents a number of significant and oftentimes competing challenges: a balance must be struck between in vivo efficacy, in vivo half-life, stability for in vitro storage, and ease and efficiency of manufacture, including conjugation efficiency and specificity. In general, it is an imperative that the conjugation process does not eliminate or significantly reduce the desired biological action of the protein in question. The protein-protein interactions required for function may require multiple regions of the protein to act in concert, and perturbing any of these with the nearby presence of a conjugate may interfere with the active site(s), or cause sufficient alterations to the tertiary structure so as to reduce active-site function. Unless the conjugation is through the N' or C' terminus, internal mutations to facilitate the linkage may be required. These mutations can have unpredictable effects on protein structure and function. There therefore continues to be a need for alternative FGF21-based therapeutics.

The reference to any art in this specification is not, and should not be taken as, an acknowledgement of any form or suggestion that the referenced art forms part of the common general knowledge.

SUMMARY OF INVENTION

The present invention relates to a composition comprising a FGF21 molecule covalently attached to the combining site of an antibody via a linker, wherein the linker is covalently attached to the side chain of a linking residue within FGF21.

The linking residue may be cysteine or lysine. The linking residue may be located at a position selected from the group consisting of amino acid residue numbers 56, 59, 69, 79, 86, 122, 125 and 129, according to the numbering of SEQ ID NO:1. The linking residue may be located at a position selected from the group consisting of amino acid residue numbers 56, 59, 86, and 122 according to the numbering of SEQ ID NO:1. The linking residue may be located at a position selected from the group consisting of residue 79, 125 and 129 according to the numbering of SEQ ID NO:1.

In some aspects, the invention provides a composition comprising a FGF21 molecule covalently connected to at least one half-life-increasing moiety at a linking residue located at residue number 56, 59, 69, 79, 86, 122, 125 and/or 129 according to the numbering of SEQ ID NO:1. In some aspects, the FGF21 molecule is covalently connected to one half life-increasing moiety. In some aspect, the linking residue is selected form the group consisting of residue numbers 79, 125 and 129. The term "half life-increasing moiety" refers to any molecule that when connected to the FGF21 molecule, increases the circulating half-life of the FGF21 molecule and/or inhibits or reduces renal clearance of the FGF21 molecule. Examples of half life-increasing moieties include PEG, mPEG, phosphorylcholine containing polymers, Fc domains, Fab, Fab', F(ab')$_2$, F$_v$, dsF$_v$, scF$_v$, V$_H$, V$_L$, diabodies, minibodies, antibodies, catalytic antibodies (discussed below), proteins (such as albumin), and other macromolecules known in the art.

The side chain of the linking residue may comprise a thiol group. The linking residue may be cysteine.

The FGF21 molecule may comprise SEQ ID NO:3. The FGF21 molecule may comprise SEQ ID NO:4. The FGF21 molecule may comprise a sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:13.

The linking residue may be located at position 125 according to the numbering of SEQ ID NO:1. The FGF21 molecule may comprise a sequence selected from the group consisting of SEQ ID NO:3, SEQ ID NO:4, SEQ ID NO:5, SEQ ID NO:6, and SEQ ID NO:7. In some embodiments, the FGF21 sequence is SEQ ID NO:7.

The linking residue may be located at position 129 according to the numbering of SEQ ID NO:1. The FGF21 molecule may comprise a sequence selected from the group consisting of SEQ ID NO:3, SEQ ID NO:4, SEQ ID NO:8, SEQ ID NO:9, and SEQ ID NO:10. In some embodiments, the FGF21 sequence is SEQ ID NO: 9.

The linking residue may be located at position 79 according to the numbering of SEQ ID NO:1. The FGF21 molecule may comprise a sequence selected from the group consisting of SEQ ID NO:3, SEQ ID NO:4, SEQ ID NO:11, SEQ ID NO:12, and SEQ ID NO:13. In some embodiments, the FGF21 sequence is SEQ ID NO:13.

In some embodiments, the linking residue may be located at a position selected from the group consisting of 1, 2, 56, 59, 69, and 122 according to the numbering of SEQ ID NO:1. In some embodiments, the linking residue may be located at a position selected from the group consisting of 1, 2, 56, 59, and 122 according to the numbering of SEQ ID NO:1. The linking residue may be lysine. The FGF21 molecule may comprise SEQ ID NO:17. The FGF21 molecule may comprise a sequence selected from the group consisting of SEQ ID NO:18, SEQ ID NO:19, SEQ ID NO:20, SEQ ID NO:21, and SEQ ID NO:23.

Certain suitable linkers are disclosed in US2009098130, the contents of which are incorporated herein by reference. In particular, aspects of US2009098130 pertaining to the general formulae describing linkers, specific linker structure, synthesis of linkers and combinations of different elements of X, Y and Z groups as specifically and generally described therein are herein included. The linker may be linear or branched, and optionally includes one or more carbocyclic or heterocyclic groups. Linker length may be viewed in terms of the number of linear atoms, with cyclic moieties such as aromatic rings and the like to be counted by taking the shortest route around the ring. In some embodiments, the linker has a linear stretch of between 5-15 atoms, in other embodiments 15-30 atoms, in still other embodiments 30-50 atoms, in still other embodiments 50-100 atoms, and in still other embodiments 100-200 atoms. Other linker considerations include the effect on physical or pharmacokinetic properties of the resulting compound, such as solubility, lipophilicity, hydrophilicity, hydrophobicity, stability (more or less stable as well as planned degradation), rigidity, flexibility, immunogenicity, and modulation of antibody binding, the ability to be incorporated into a micelle or liposome, and the like.

In some aspects of the invention, the compound comprises a linker covalently linked to the side chain of the linking residue. The linker may comprise the formula: X—Y—Z; wherein X is a biologically compatible connecting chain including any atom selected from the group consisting of C, H, N, O, P, S, F, Cl, Br, and I, and may comprise a polymer or block co-polymer, and is covalently linked to the linking residue where the linker is linear, Y is an optionally present recognition group comprising at least a ring structure; and Z is an attachment moiety comprising a covalent link to an amino acid side chain in a combining site of an antibody.

When present, Y may have the optionally substituted structure:

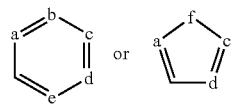

wherein a, b, c, d, and e are independently carbon or nitrogen; f is carbon, nitrogen, oxygen, or sulfur; Y is attached to X and Z independently at any two ring positions of sufficient valence; and no more than four of a, b, c, d, e, or f are simultaneously nitrogen and preferably a, b, c, d, and e in the ring structure are each carbon. In some aspects, Y may be phenyl. Although not wishing to be bound by any theory, it is believed that the Y group can assist in positioning the reactive group into an antibody combining site so that the Z group can react with a reactive amino acid side chain.

The linker may be designed such that it contains a reactive group capable of covalently or non-covalently forming a bond with a macromolecule, such as an antibody, protein, or fragment thereof. The reactive group is chosen for use with a reactive residue in a particular combining site. E.g. a chemical moiety for modification by an aldolase antibody may be a ketone, diketone, beta lactam, active ester haloketone, lactone, anhydride, maleimide, alpha-haloacetamide, cyclohexyl diketone, epoxide, aldehyde, amidine, guanidine, imine, enamine, phosphate, phosphonate, epoxide, aziridine, thioepoxide, masked or protected diketone (e.g. ketal), lactam, haloketone, aldehyde, and the like. In embodiments of the present invention linking a peptide of the invention with a linker, Z is the reactive group.

In some embodiments, Z, prior to conjugation with the side-chain of a residue in the combining site of an antibody, includes one or more C=O groups arranged to form an azitidinone, diketone, an acyl beta-lactam, an active ester, a haloketone, a cyclohexyl diketone group, an aldehyde, a maleimide, an activated alkene, an activated alkyne or, in general, a molecule comprising a leaving group susceptible to nucleophilic or electrophilic displacement. Other groups may include a lactone, an anhydride, an alpha-haloacetamide, an imine, a hydrazide, or an epoxide. Exemplary linker electrophilic reactive groups that can covalently bond to a reactive nucleophilic group (e.g., a lysine or cysteine side chain) in a combining site of antibody include acyl beta-lactam, simple diketone, succinimide active ester, maleimide, haloacetamide with linker, haloketone, cyclohexyl diketone, aldehyde, amidine, guanidine, imine, enamine, phosphate, phosphonate, epoxide, aziridine, thioepoxide, a masked or protected diketone (a ketal for example), lactam, sulfonate, and the like, masked C=O groups such as imines, ketals, acetals, and any other known electrophilic group. In certain embodiments, the reactive group includes one or more C=O groups arranged to form an acyl beta-lactam, simple diketone, succinimide active ester, maleimide, haloacetamide with linker, haloketone, cyclohexyl diketone, or aldehyde. Z may be a substituted alkyl, substituted cycloalkyl, substituted aryl, substituted arylalkyl, substituted heterocyclyl, or substituted heterocyclylalkyl, wherein at least one substituent is a 1,3-diketone moiety, an acyl beta-lactam, an active ester, an alpha-haloketone, an aldehyde, a maleimide, a lactone, an anhydride, an alpha-haloacetamide, an amine, a hydrazide, or an epoxide. Z group may be covalently linked to a macromolecule scaffold that can provide increased half-life to the peptides of the invention. Z group if present may be covalently linked to the combining site of an antibody.

In some aspects, prior to conjugation (for example, with the combining site of an antibody), Z has the structure:

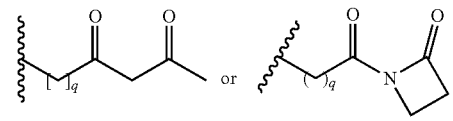

wherein q=0-5. q may be 1 or 2. q may be 1. In other aspects, q may be 2.

In some aspects, following conjugation with the antibody combining site, Z has the structure:

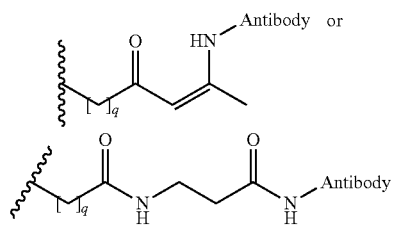

wherein q=0-5 and Antibody-N— is a covalent bond to a side chain in a combining site of an antibody. q may be 1 or 2. q may be 1. In other aspects, q may be 2.

X may be a group comprising three components; Xp-Xs-Xy, wherein Xp is a group specifically adapted to be combinable with the side chain of the linking residue of the FGF21 protein, Xs is a spacer region of the X group, and Xy is a group adapted to bind to the Y group. In some aspects, Xy is selected from an amide bond, an enamine bond, or a guanidinium bond. Xy may be selected so as to provide a hydrogen molecule adjacent (within two atoms) to the Y group. While not wishing to be bound by theory, it is believed that the H atom can assist the Y group recognition of a hydrophobic pocket through H-bond interaction, particularly in respect of the hydrophobic pocket of the binding cleft of a catalytic antibody, such as h38C2. Thus the amide bond, for example, may be orientated such that the NH group is directly bonded to the Y group, providing the H of the NH group for hydrogen bonding. Alternatively, the C=O group of an amide may be bonded to the Y group, with the H of the NH group up to 2 atoms adjacent to the Y group, but still available for H-bonding. In some embodiments, Xy is absent. In some embodiments the Xy group has the formula:

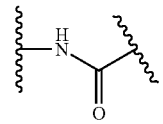

In some aspects, Xs is selected such that Xs does not provide any overly reactive groups. Xs may be selected so as to provide an overall length of the X groups of between 2-15 atoms. Xs may be selected so that the overall length of the X group is between 2 and 10 atoms. Xs may be selected so that the overall length of X group is 4-8 atoms. Xs may be selected so that the overall length of X group is 5 atoms. Xs may be selected so that the overall length of X group is 6 atoms. In some aspects, Xs may comprise one of the following formulae:

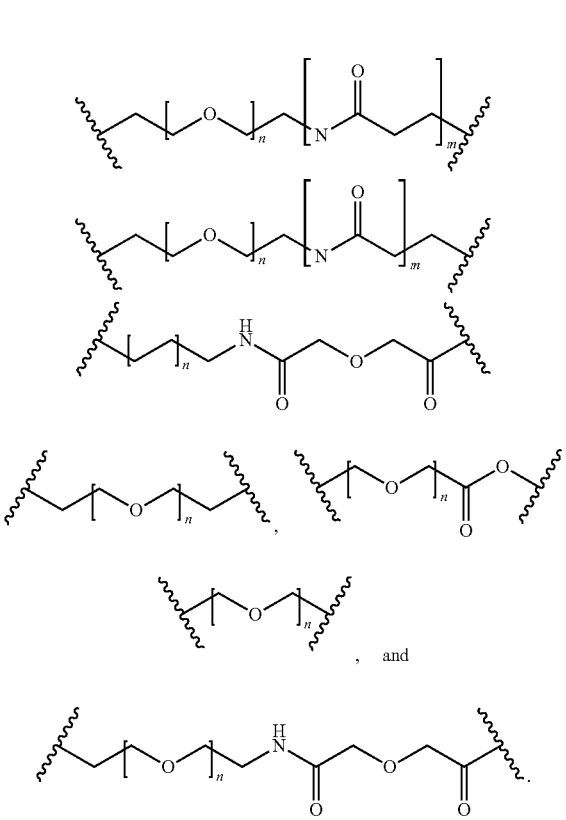

where n=1, 2, 3, 4, 5, 6, 7, 8, 9, or 10, and m is present or absent; n may be 1, 2, 3, 4, 5, or 6; n may be 1, 2, 3, or 4; n may be 1; n may be 2; n may be 3; n may be 4.

In some aspects, Xs comprises one of the following formulae:

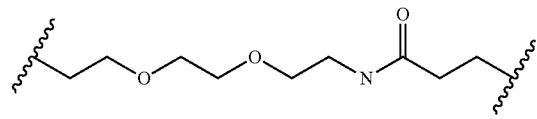

(exemplified in L1 and L2)

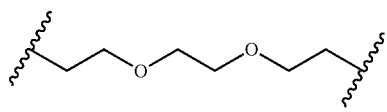

(exemplified in L3 and L7)

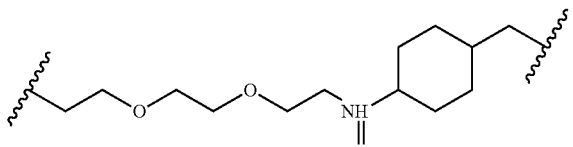

(exemplified in L4)

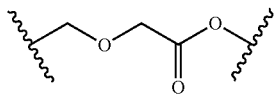 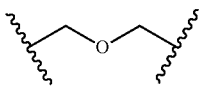

(exemplified in L5)  (exemplified in L6)

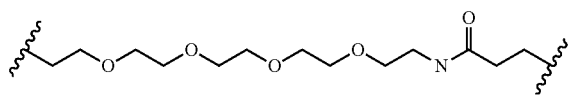

(exemplified in L8)

Xp ideally is selected so as to enable a specific directional covalent linking strategy to the linking residue of the FGF21 protein. For example, where the linking residue comprises a nucleophilic group, Xp may be an electrophilic group and vice versa. For example, if the linking residue side chain comprises an amine group, such as K, H, Y, orthinine, Dap, or Dab, Xp may be COOH, or other similarly reactive electrophile. If the linking residue is D or E, Xp may comprise a nucleophilic group, such as an amine group. Either of these strategies permits a covalent bond to be formed between the Xp group and the linking reside by amide bond formation strategies. Where the linking group is an amine group, Xp may comprise the formula:

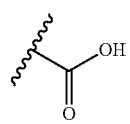

Where the linking residue is C, homologs of C, or other thiol-group containing residues, Xp may comprise a maleimide group (or similar) permitting a thiol-maleimide addition reaction strategy to covalently link the Xp group to the linking residue. In some aspects, Xp may also comprise a thiol group, allowing a disulphide bridge to be formed between the linking residue and Xp group. In some aspects, Xp may be maleimide:

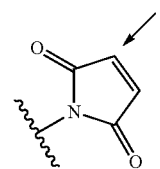 [SMILES: *N1C(=O)C=CC1=O]

wherein the arrow indicates the point of attachment to the FGF21 linking residue and the parallel line represents to attachment to the Y group of the linker. Where the FGF21 linking residue is a cysteine residue, or other thiol bearing side chain, the mechanism of conjugation may be as follows:

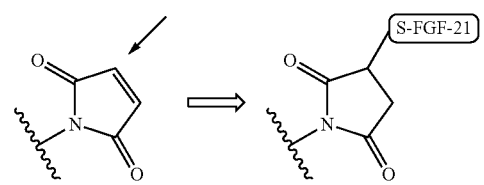

In some aspects, the Xp group comprises a substituted maleimide:

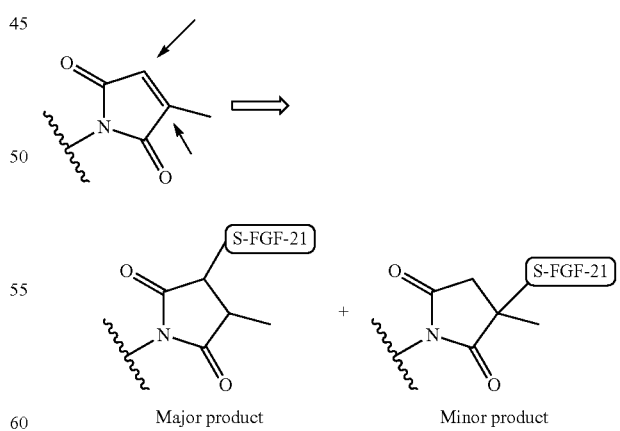

Major product    Minor product

In some aspects, the XY components of the linker prior to conjugation and following conjugation may be selected from the following:

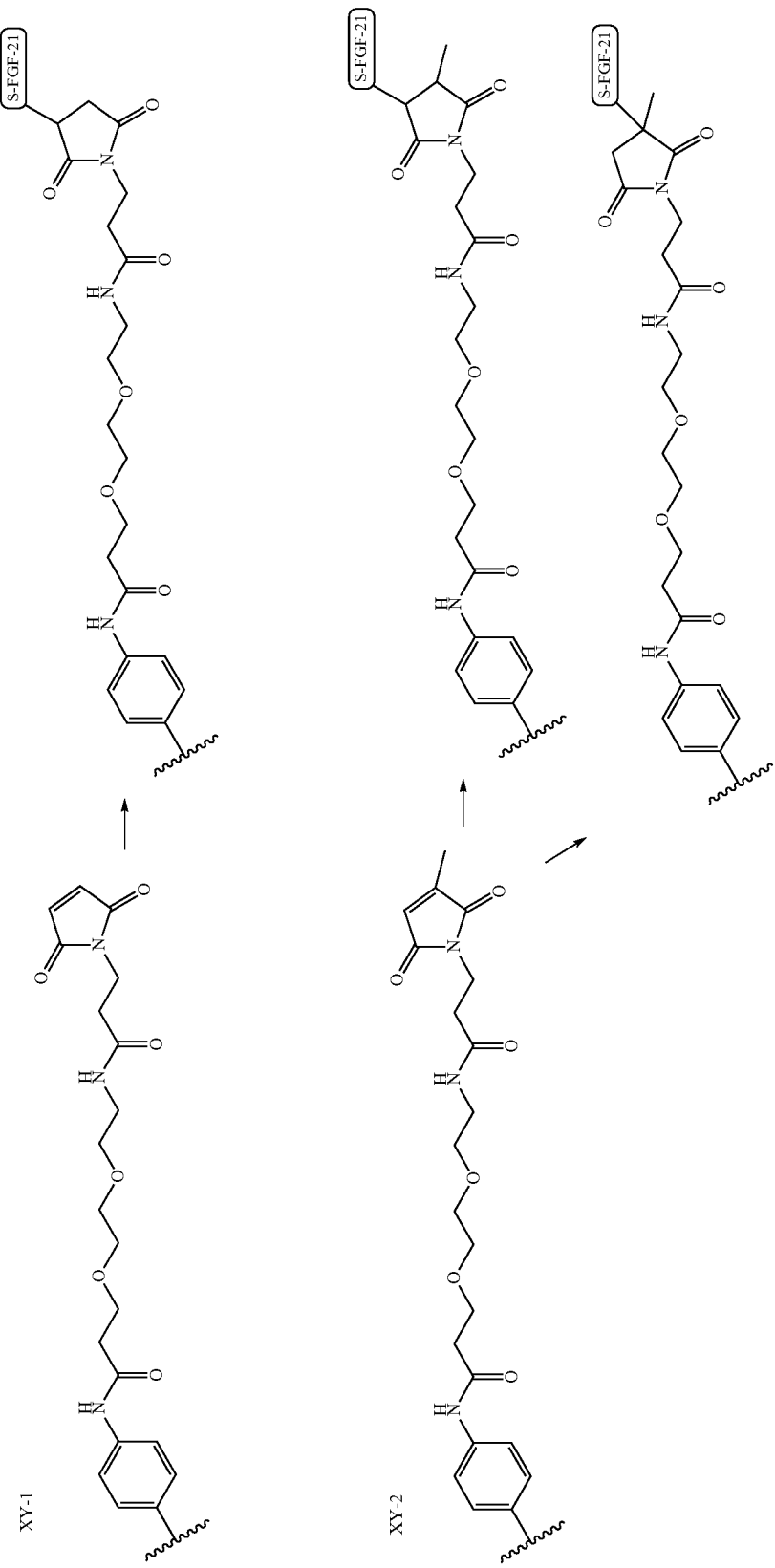

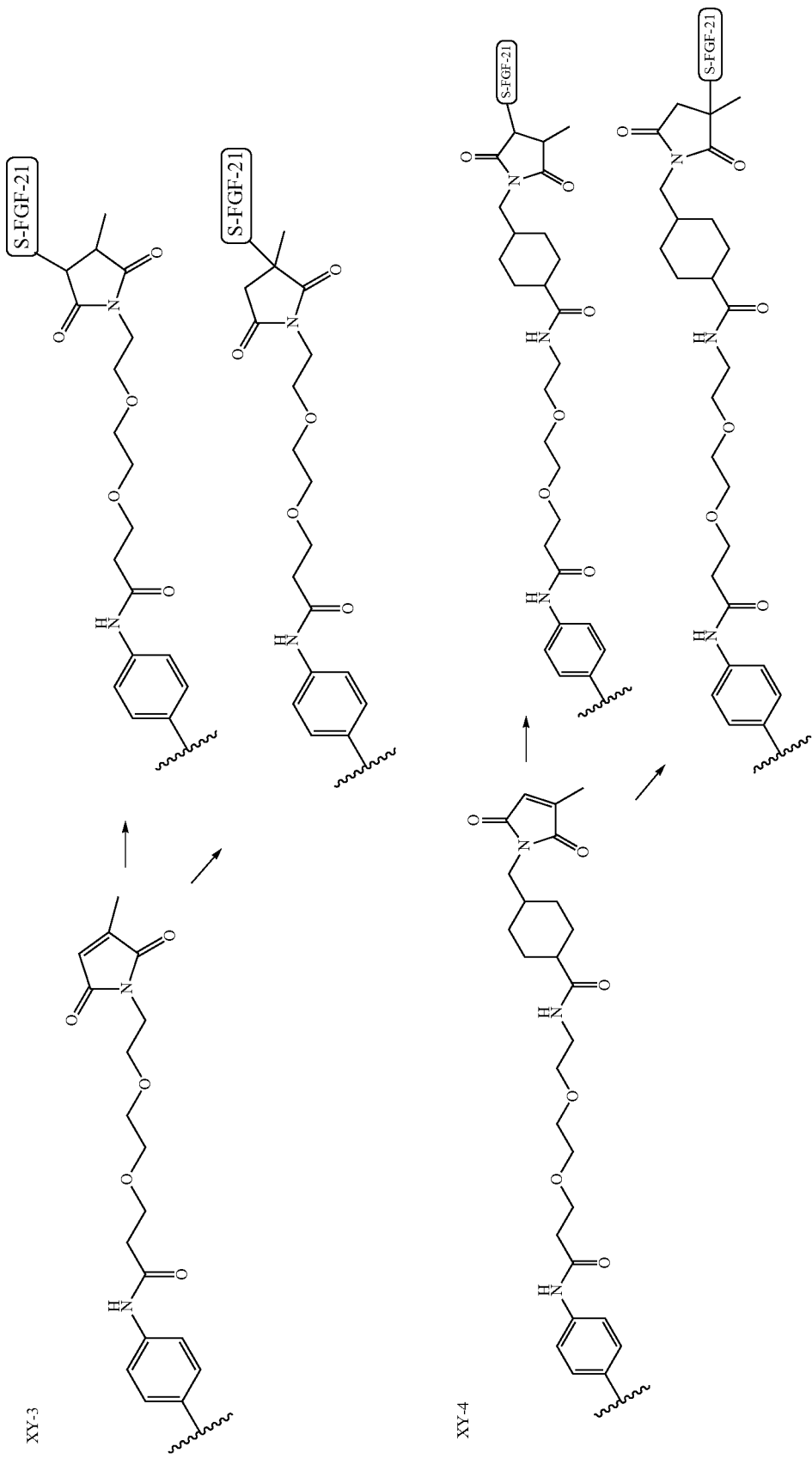

Components XY-1, XY-2, XY-3, and XY-4 are particularly useful in embodiments conjugating to a thiol-group bearing side chain on the FGF21 molecule.

In some embodiments, the linker may be Linker-1 (L1):

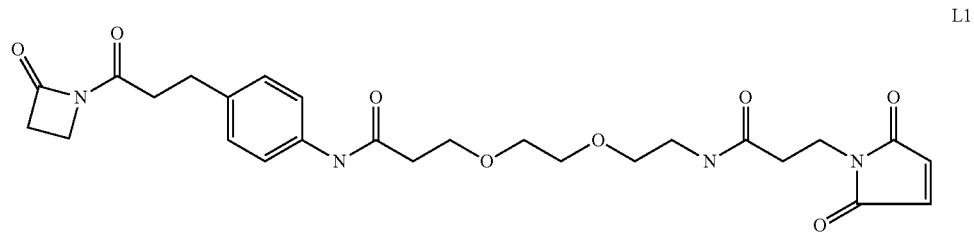 [SMILES: O=C(CCN1C(=O)C=CC1=O)NCCOCCOCCC(=O)Nc1ccc(CCC(=O)N2CCC2=O)cc1]

L1

When L1 is conjugated to the antibody, the antibody-L1 complex may comprise the formula:

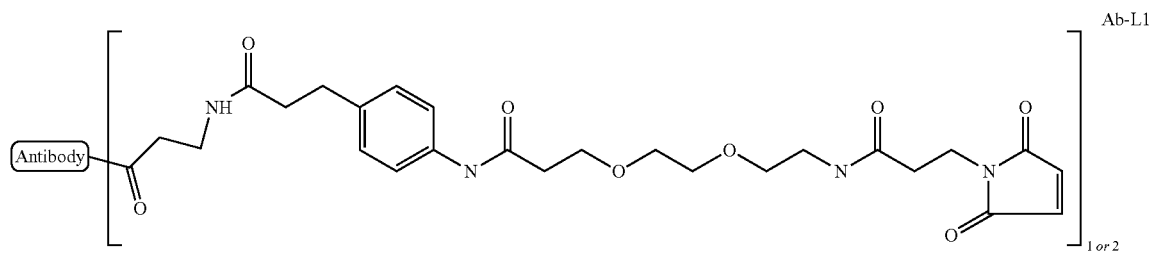

Ab-L1

When L1 is conjugated to the FGF21 molecule, the L1-FGF21 complex may comprise the formula:

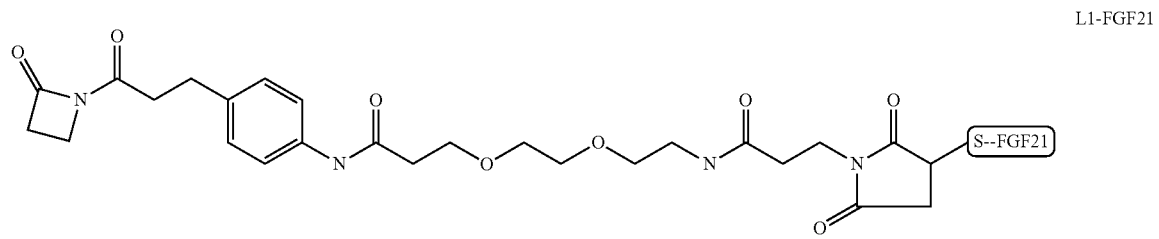 [SMILES: CC1CC(=O)N(CCC(=O)NCCOCCOCCC(=O)Nc2ccc(CCC(=O)N3CCC3=O)cc2)C1=O]

L1-FGF21

When L1 is conjugated to the antibody and FGF21 molecule, the antibody-L1-FGF21 complex may comprise the formula:

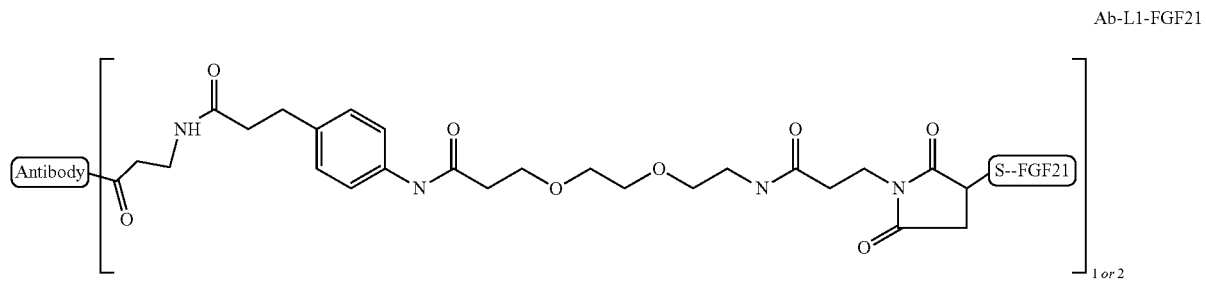

Ab-L1-FGF21

In some embodiments, the linker may be Linker-2 (L2):

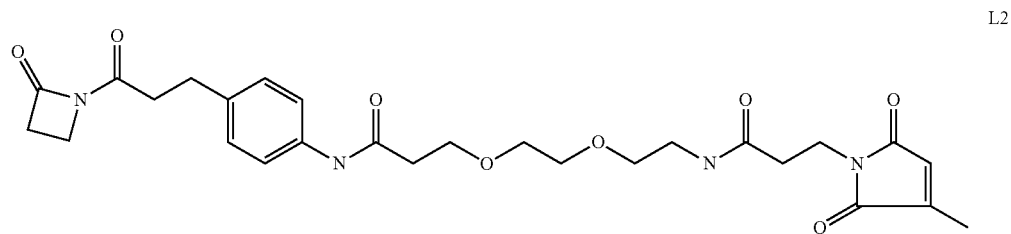 [SMILES: CC1=CC(=O)N(CCC(=O)NCCOCCOCCC(=O)Nc2ccc(CCC(=O)N3CCC3=O)cc2)C1=O]

L2

When L2 is conjugated to the antibody, the antibody-L2 complex may comprise the formula:

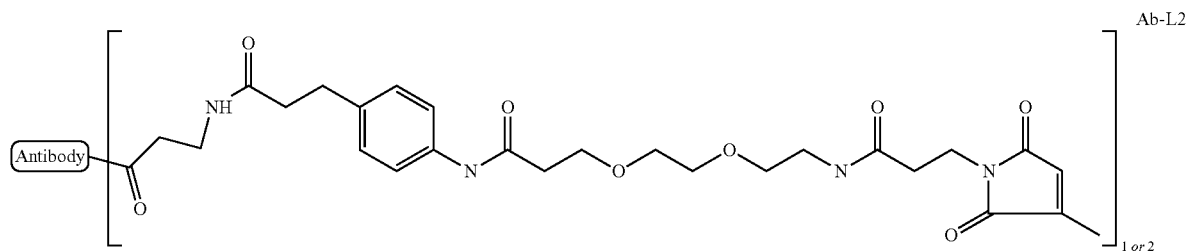

Ab-L2

When L2 is conjugated to the FGF21 molecule, the L2-FGF21 complex may comprise one of the following formulae:

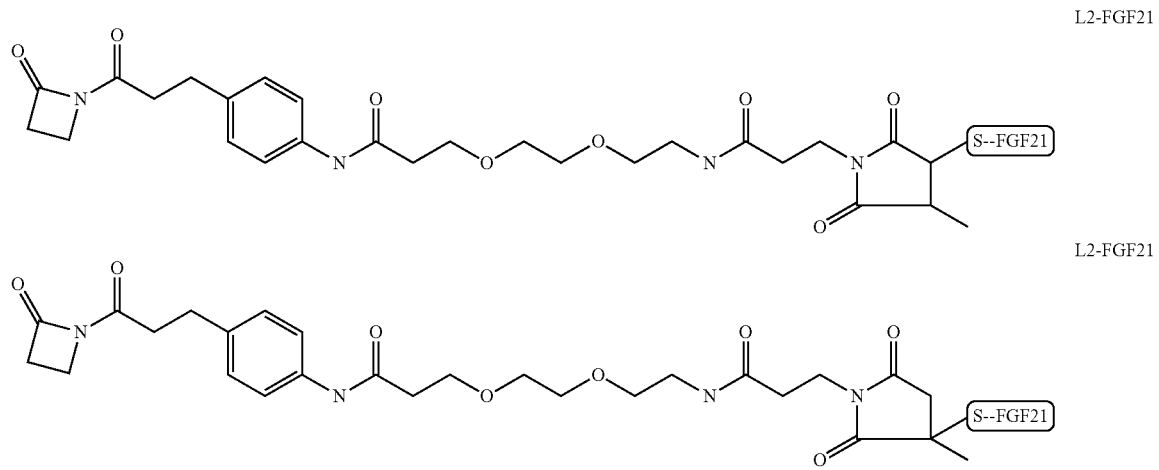

L2-FGF21

L2-FGF21

When L2 is conjugated to the antibody and the FGF21 molecule, the antibody-L2-FGF21 complex may comprise one of the following formulae:

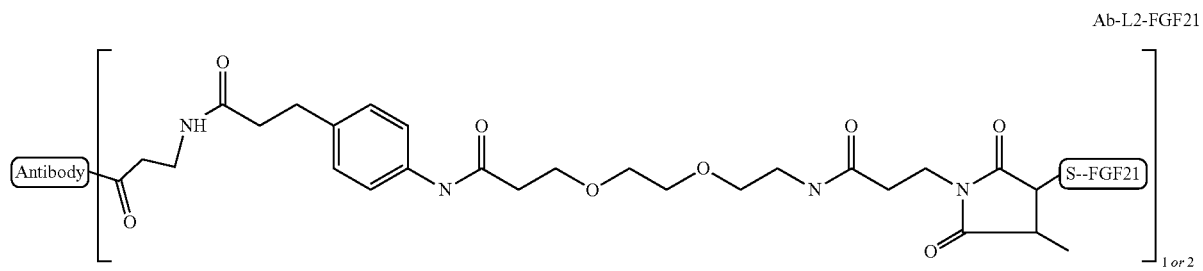

Ab-L2-FGF21

-continued
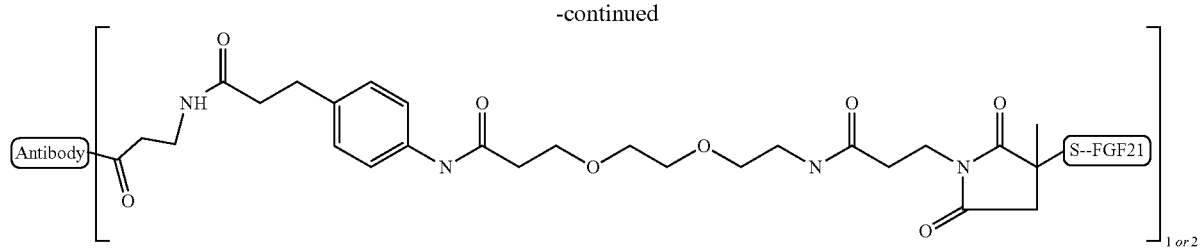
In some embodiments, the linker may be Linker-3 (L3):
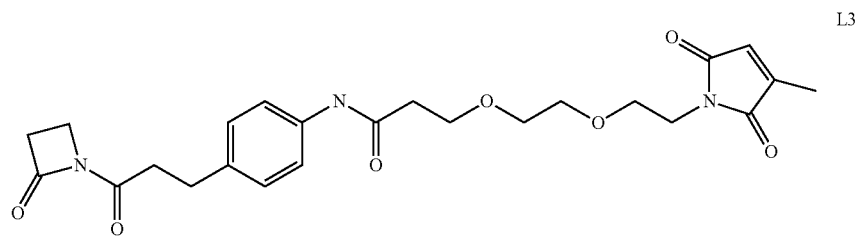 [SMILES: CC1=CC(=O)N(CCOCCOCCC(=O)Nc2ccc(CCC(=O)N3CCC3=O)cc2)C1=O]
When L3 is conjugated to the antibody, the antibody-L3 complex may comprise the formula:
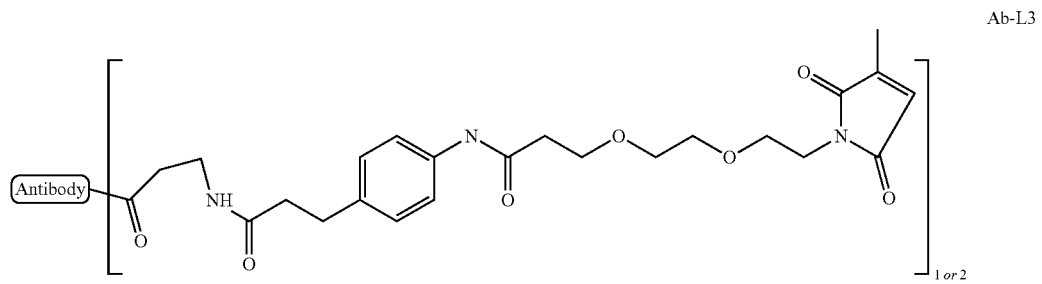
When L3 is conjugated to the FGF21 molecule, the L3-FGF21 complex may comprise one of the following formulae:
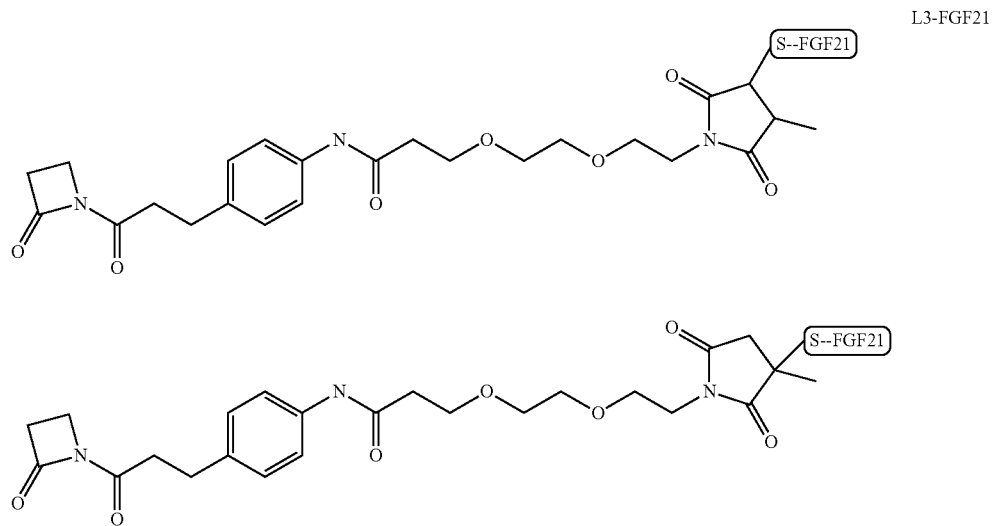

When L3 is conjugated to the antibody and the FGF21 molecule, the antibody-L3-FGF21 complex may comprise the formula:
Ab-L3-FGF21
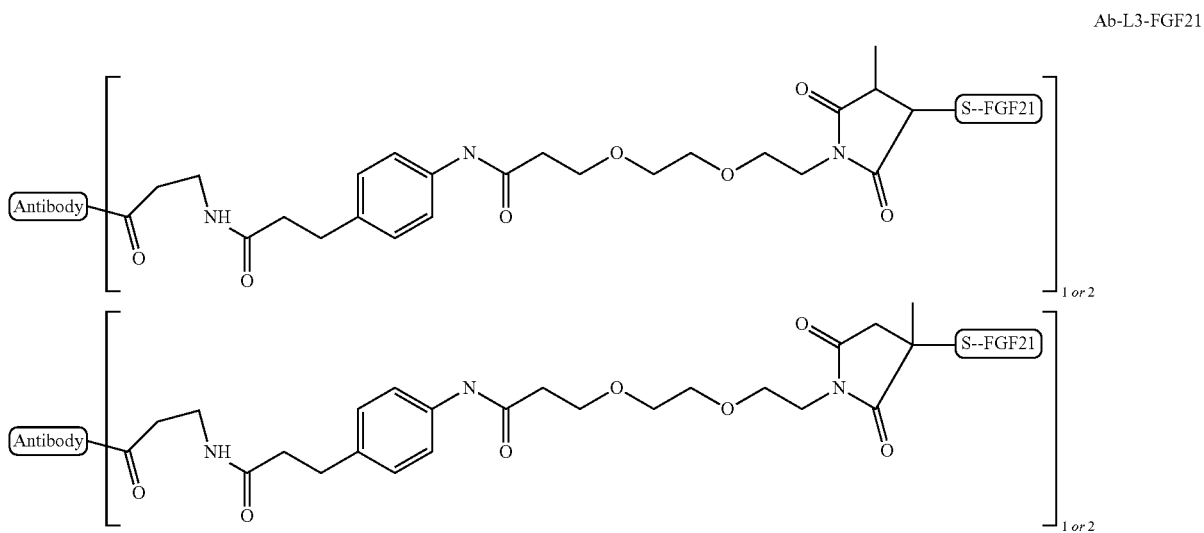
In some embodiments, the linker may be Linker-4 (L4):
L4
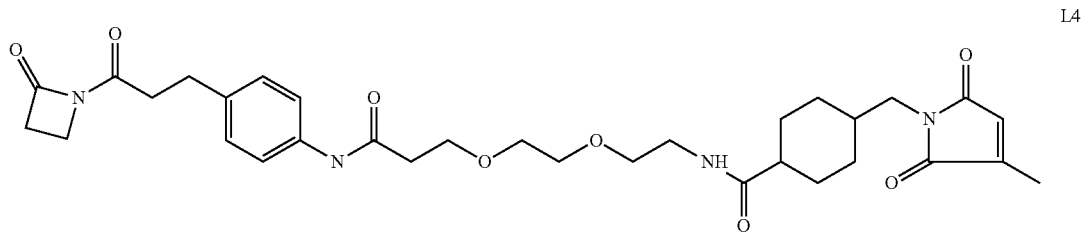 [SMILES: CC1=CC(=O)N(CC2CCC(C(=O)NCCOCCOCCC(=O)Nc3ccc(CCC(=O)N4CCC4=O)cc3)CC2)C1=O]
When conjugated to the antibody, the antibody-L4 complex may comprise the formula:
Ab-L4
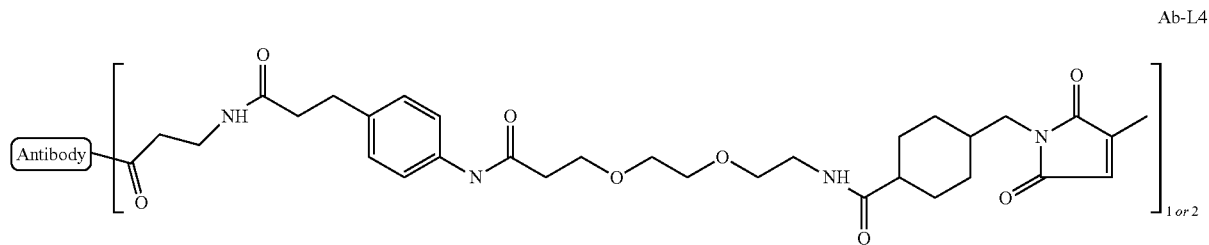
When conjugated to the FGF21 molecule, the L4-FGF21 complex may comprise the formula:
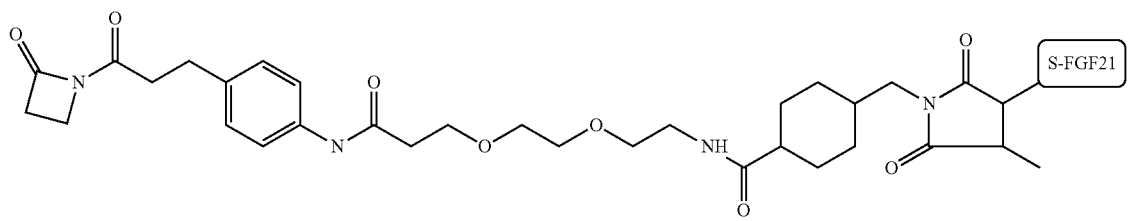

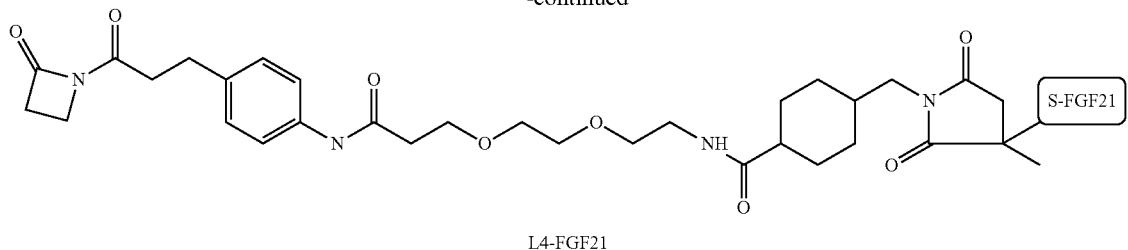
L4-FGF21
When L4 is conjugated to the antibody and the FGF21 molecule, the antibody-L4-FGF21 complex may comprise the formula:
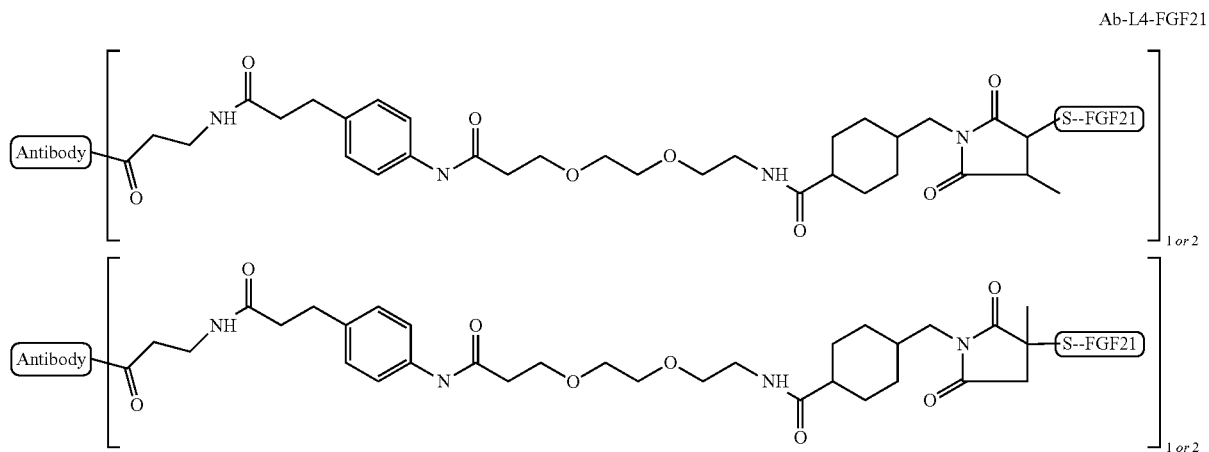
Ab-L4-FGF21
In some embodiments, the linker may be Linker-5 (L5):
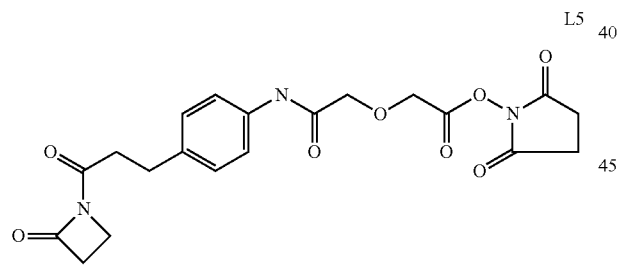
L5
When L5 is conjugated to the antibody, the antibody-L5 complex may comprise the formula:
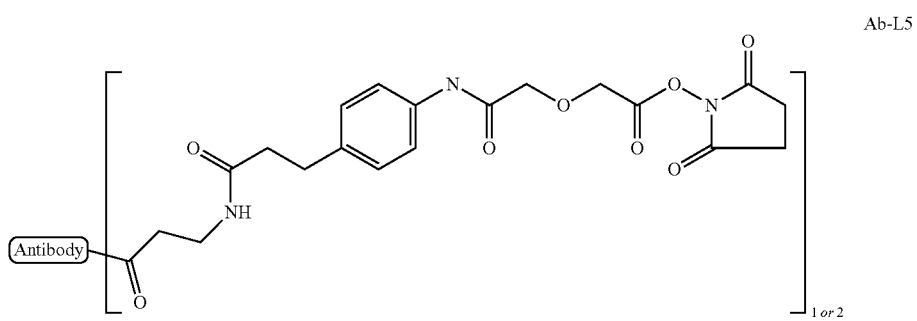
Ab-L5

When L5 is conjugated to the FGF21 molecule, the L5-FGF21 complex may comprise the formula:

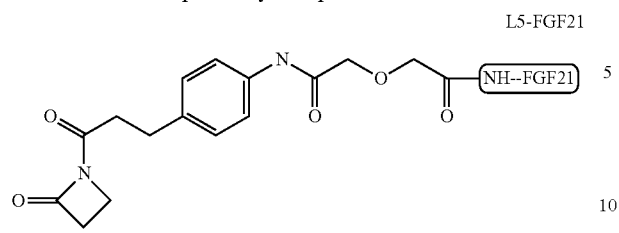

L5-FGF21

When L5 is conjugated to the antibody and FGF21 molecule, the antibody-L5-FGF21 complex may comprise the formula:

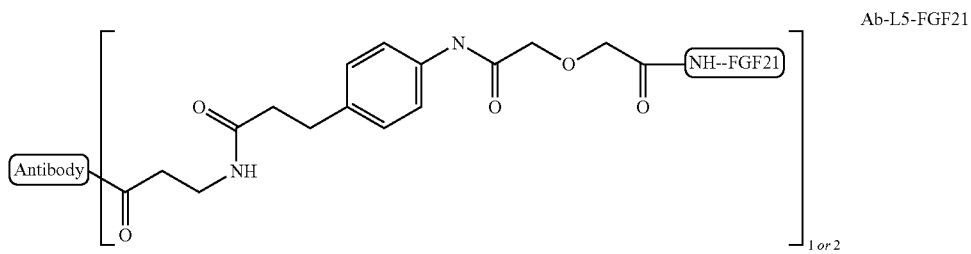

Ab-L5-FGF21

In some aspects, the linker may be Linker-6 (L6).

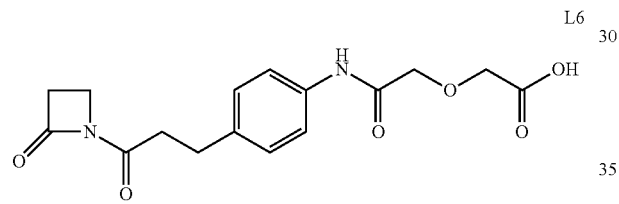

L6

When L6 is conjugated to the antibody, the antibody-L5 complex may comprise the formula:

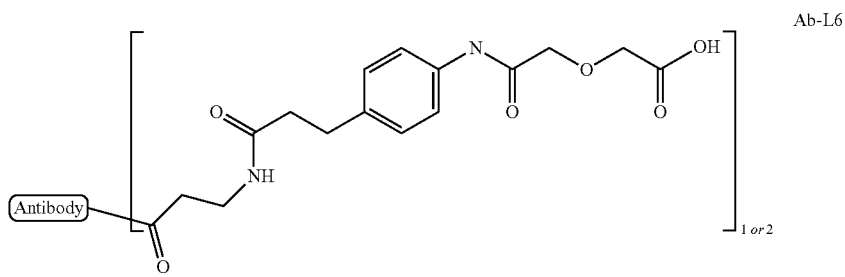

Ab-L6

When L6 is conjugated to the FGF21 molecule, the L6-FGF21 complex may comprise the same formula as that for L5-FGF21. Similarly, when L6 is conjugated to the antibody and the FGF21 molecule, the antibody-L6-FGF21 complex may comprise the same formula as that for Ab-L5-FGF21.

In some embodiments, the linker may be Linker-7 (L7):

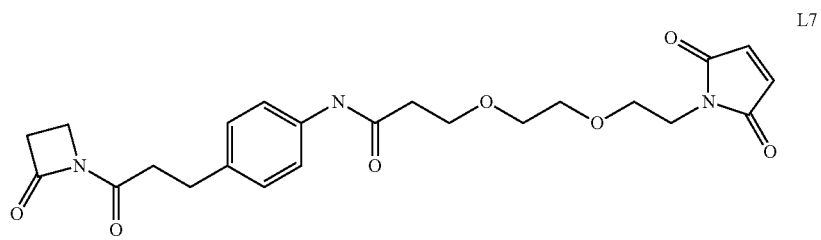 [SMILES: O=C(CCOCCOCCN1C(=O)C=CC1=O)Nc1ccc(CCC(=O)N2CCC2=O)cc1]

L7

When conjugated to the antibody, the antibody-L7 complex may comprise the formula:
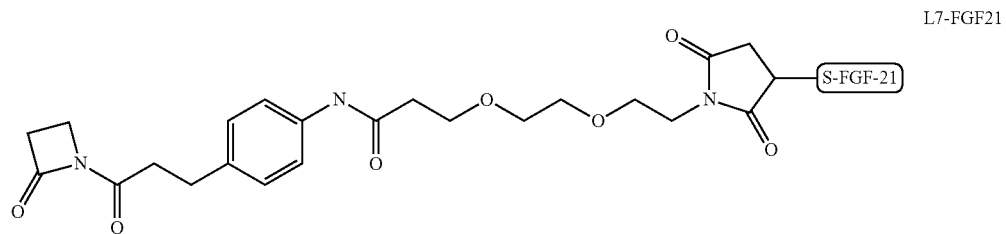 [SMILES: CC1CC(=O)N(CCOCCOCCC(=O)Nc2ccc(CCC(=O)N3CCC3=O)cc2)C1=O]
L7-FGF21
When conjugated to the FGF21 molecule, the L7-FGF21 complex may comprise the formula:
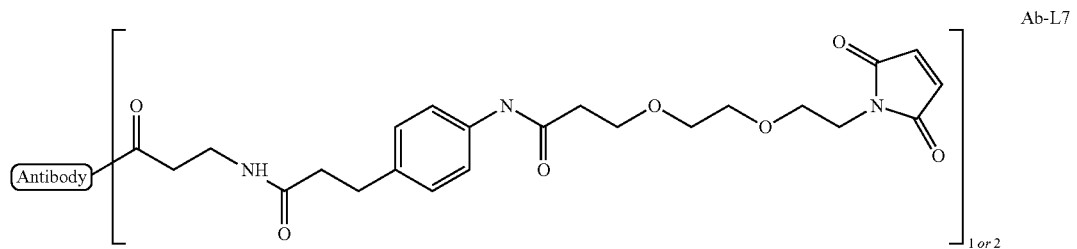
Ab-L7
When conjugated to the antibody and FGF21 molecule, the antibody-L7-FGF21 complex may comprise the formula:
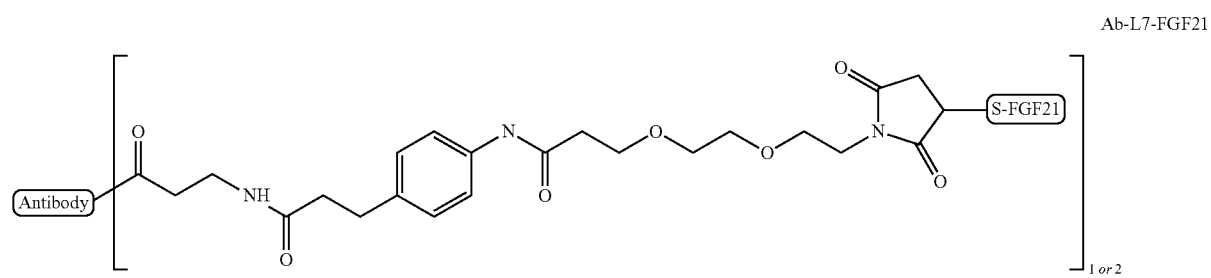
Ab-L7-FGF21
In some embodiments, the linker may be Linker-8 (L8):
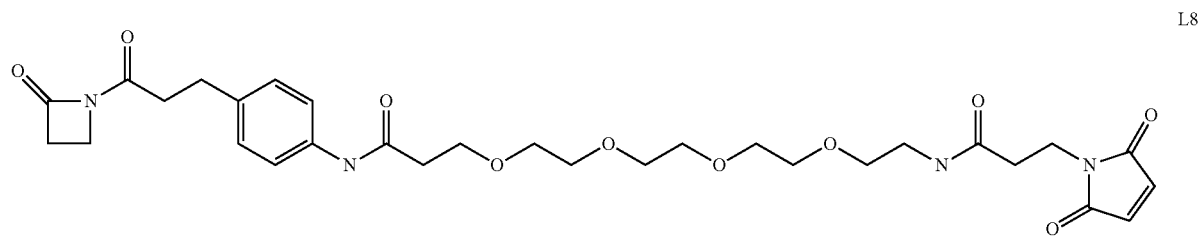 [SMILES: O=C(CCN1C(=O)C=CC1=O)NCCOCCOCCOCCOCCC(=O)Nc1ccc(CCC(=O)N2CCC2=O)cc1]
L8

When L8 is conjugated to the antibody, the antibody-L8 complex may comprise the formula:

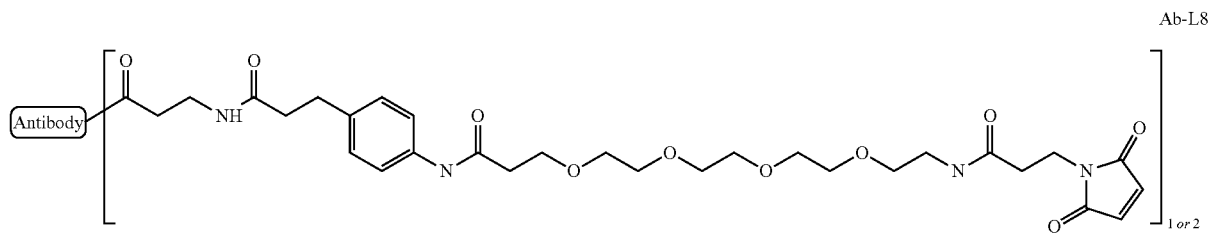

Ab-L8

When L8 conjugated to the FGF21 molecule, the L8-FGF21 complex may comprise the formula:

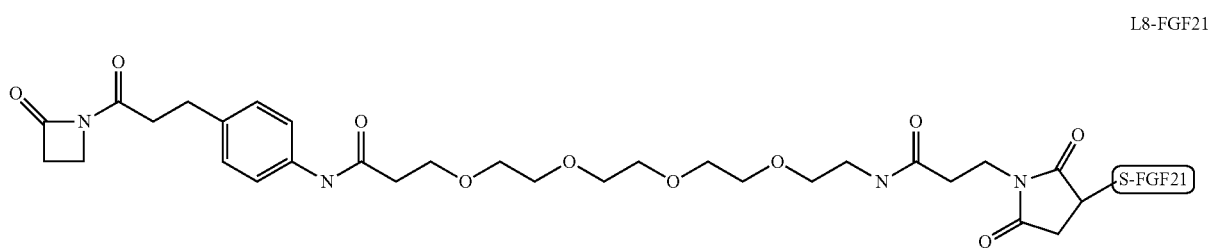 [SMILES: CC1CC(=O)N(CCC(=O)NCCOCCOCCOCCOCCC(=O)Nc2ccc(CCC(=O)N3CCC3=O)cc2)C1=O]

L8-FGF21

When L8 is conjugated to the antibody and the FGF21 molecule, the antibody-L8-FGF21 complex may comprise the formula:

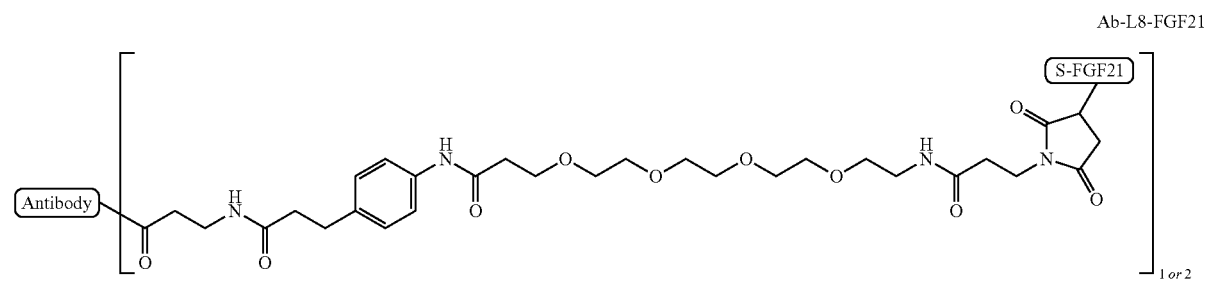

Ab-L8-FGF21

In some embodiments, the Ab-linker-FGF21 conjugate may be of the formula:

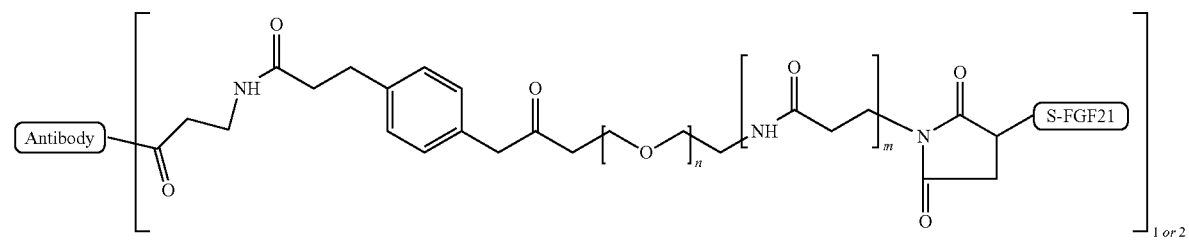

wherein the Antibody combining site is covalently linked to the linker, S-FGF21 is the covalent linkage to a thiol-bearing side chain on an FGF21 molecule, n=1, or 2, or 3, or 4, 5, 6, 7, 8, 9, or 10; n may be 1, 2, 3, 4, 5, or 6; n may be 1; n may be 2; n may be 3; n may be 4, and m is optional. M may be absent. M may be present.

In some embodiments, the Ab-linker-FGF21 conjugate may be of the formula:

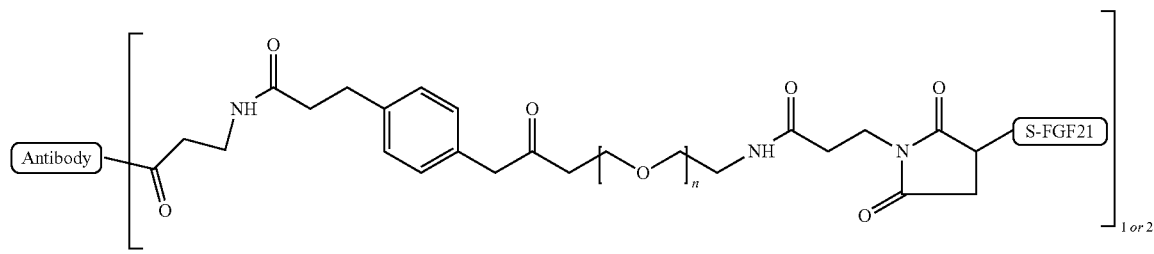

wherein the Antibody combining site is covalently linked to the linker, S-FGF21 is a covalent linkage to a thiol-bearing side chain on an FGF21 molecule, n=1, or 2, or 3, or 4, 5, 6, 7, 8, 9, or 10; n may be 1, 2, 3, 4, 5, or 6; n may be 1; n may be 2; n may be 3; n may be 4.

In some embodiments, the composition comprises the formula:

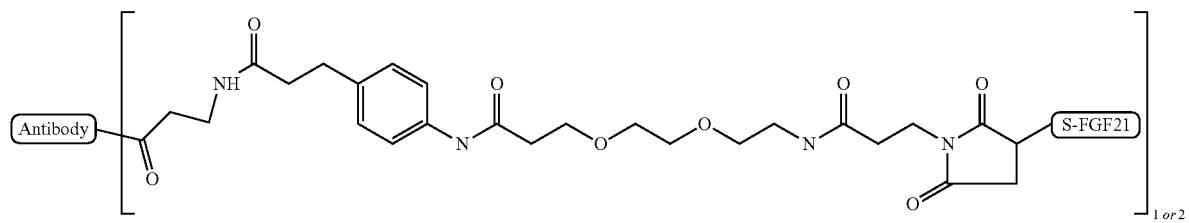

wherein Antibody is a covalent linkage to the combining site of an antibody, S-FGF21 is a covalent linkage to a thiol-bearing side chain on an FGF21 molecule. In some embodiments, the FGF21 molecule comprises SEQ ID NO:10. In some embodiments, the FGF21 molecule comprises SEQ ID NO:7.

In some aspects, the invention is directed towards the linkers and linker components as described herein, particularly, but not limited to, the X groups described herein. In some aspects, the invention is directed towards compositions comprising an antibody or antigen binding portion thereof, covalently conjugated to a linker or linker group as described herein. In some aspects, the linker or linker group may be further directly or indirectly conjugated to a peptide or protein. It will be apparent that the usefulness of the linkers and antibody linker conjugates is not limited by application with FGF21 molecules, and said Ab-linker conjugates may be conjugates with other peptides, proteins and therapeutic and targeting agents. For these purposes, the same structures as herein described depicting S-FGF21 and NH-FGF21 may be understood to apply to other proteins, peptides and therapeutic and targeting molecules; the FGF21 nomenclature of the represented structure being replaced with said protein, peptide or molecule.

In some aspects, the invention provides a linker of the formula:

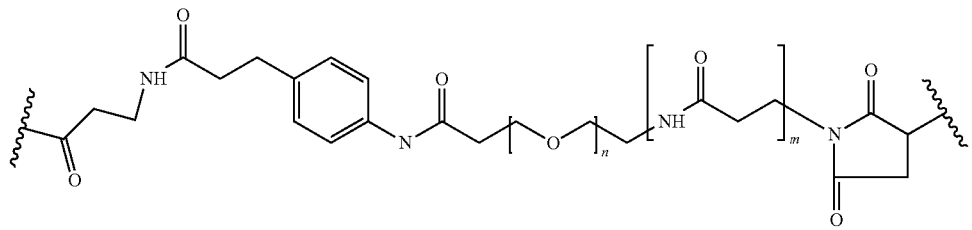

wherein n=1, or 2, or 3, or 4, 5, 6, 7, 8, 9, or 10; n may be 1, 2, 3, 4, 5, or 6; n may be 1; n may be 2; n may be 3; n may be 4. M may be absent. M may be present.

In some aspects, the invention provides a linker of the formula:

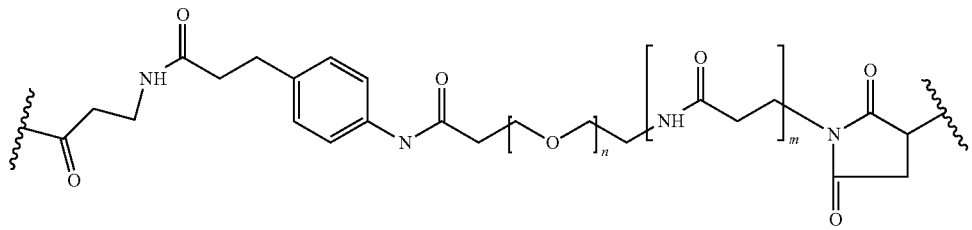

wherein n=1, or 2, or 3, or 4, 5, 6, 7, 8, 9, or 10; n may be 1, 2, 3, 4, 5, or 6; n may be 1; n may be 2; n may be 3; n may be 4. M may be absent. M may be present.

In some embodiments, the invention is directed towards a composition comprising a linker selected from the group consisting of L1, L2, L3, L4, L5, L6, L7 and L8, as well as other specific and general linker formulae herein described. IN some aspects, the invention is directed towards methods of making said linkers and antibody-linker, protein-linker, or antibody-linker-protein conjugates thereof.

In some embodiments, the invention relates to a composition comprising a FGF21 molecule covalently attached to the combining site of an antibody via a linker, wherein the linker is covalently attached to the side chain of a linking residue within FGF21 forming a conjugated protein-antibody complex, such that the subcutaneous half-life of the conjugated protein-antibody complex is at least about 20 hrs in murine models. In some embodiments, the SC half-life is at least about 25 hrs. In some embodiments, the SC half-life is at least about 30 hrs. In some embodiments, the SC half-life is at least about 33 hrs. In some embodiments, the SC half-life is at least about 35 hrs in rat models. In some embodiments, the SC half-life is at least about 36 hrs in rat models. In some embodiments, the SC half-life is at least about 40 hrs in primate models. In some embodiments, the SC half-life is at least about 45 hrs in primate models. In some embodiments, the invention provides a conjugated antibody-protein complex with an IV half-life of at least about 28 hrs in murine models. In some embodiments, the invention provides a conjugated antibody-protein complex with an IV half-life of at least about 55 hrs in rat models. In some embodiments, the invention provides a conjugated antibody-protein complex with an IV half-life of at least about 55 hrs in rat models. In some embodiments, the invention provides a conjugated antibody-protein complex with an IV half-life of at least about 60 hrs in rat models. In some embodiments, the invention provides a conjugated antibody-protein complex with an IV half-life of at least about 60 hrs in primate models. In some embodiments, the invention provides a conjugated antibody-protein complex with an IV half-life of at least about 65 hrs in primate models. In some embodiments, the invention provides a conjugated antibody-protein complex with an IV half-life following a single dose of at least about 30 hrs in humans. In some embodiments, the invention provides a conjugated antibody-protein complex with an IV half-life following a single dose of at least about 35 hrs in humans.

In some embodiments, the invention relates to a composition comprising a FGF21 molecule covalently attached to the combining site of an antibody via a linker, wherein the linker is covalently attached to the side chain of a linking residue within FGF21 forming a conjugated protein-antibody complex, such that the subcutaneous bioavailability of the conjugated protein-antibody complex is at least about 50% in murine models. In some embodiments, the SC bioavailability is at least about 55%. In some embodiments, the SC bioavailability is at least about 65%. In some embodiments, the SC bioavailability is at least about 50% in rat models. In some embodiments, the SC bioavailability is at least about 50% in primate models. In some embodiments, the SC bioavailability is at least about 60% in primate models. In some embodiments, the SC bioavailability is at least about 65% in primate models.

In some embodiments, the invention relates to a composition comprising a FGF21 molecule covalently attached to the combining site of an antibody via a linker, wherein the linker is covalently attached to the side chain of a linking residue within FGF21 forming a conjugated protein-antibody complex, such that the subcutaneous bioavailability of the conjugated protein-antibody complex is at least about 50% in murine models. In some embodiments, the SC bioavailability is at least about 55%. In some embodiments, the SC bioavailability is at least about 65%.

In some embodiments, the invention relates to a composition comprising a FGF21 molecule covalently attached to the combining site of an antibody via a linker, wherein the linker is covalently attached to the side chain of a linking residue within FGF21 forming a conjugated protein-antibody complex, such that the conjugated protein-antibody complex has a $EC_{50}$ potency in a Glut1 Taqman assay of less than about 5 nM. In some embodiments, the $EC_{50}$ potency in a Glut1 Taqman assay is less than about 4 nM. In some embodiments, the $EC_{50}$ potency in a Glut1 Taqman assay is less than about 3 nM.

In some embodiments, the conjugated protein-antibody complex combines two or more favourable advantages, such as SC half-life, IV half-life, glucose uptake, potency, bioavailability, ease of manufacture, conjugation efficiency, in vivo stability, in vitro stability, resistance to hydrolysis, and compatibility between antibody, linker and protein.

Antibodies

The contents of US2006205670 are incorporated herein by reference—in particular paragraphs [0153]-[0233], describing antibodies, useful fragments and variants and modifications thereof, combining sites and CDRs, antibody preparation, expression, humanization, amino acid modification, glycosylation, ADCC, CDC, increasing serum half life of antibodies, expression vectors, mammalian host systems, and folding, amongst other elements of antibody technology.

"Combining site", as used herein, (also known as the antibody binding site) refers to the region of the immunoglobulin or Ig domains that combine (or can combine) with the determinant of an appropriate antigen (or a structurally similar protein). The term generally includes the CDRs and the adjacent framework residues that are involved in antigen binding.

"Aldolase antibodies" as used herein, refers to antibodies containing combining site portions that, when unencumbered (for example by conjugation), catalyze an aldol addition reaction between an aliphatic ketone donor and an aldehyde acceptor. Aldolase antibodies are capable of being generated by immunization of an immune-responsive animal with an immunogen that includes a 1,3 diketone hapten of the formula:

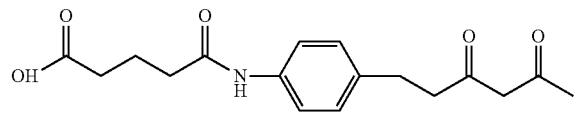 [SMILES: CC(=O)CC(=O)CCc1ccc(NC(=O)CCCC(=O)O)cc1]

coupled to a carrier protein, and further characterized by having a lysine with a reactive ε-amino group in the combining site of the antibody. Aldolase antibodies are further characterized by their catalytic activity being subject to inhibition with the 1,3-diketone hapten by formation of a complex between the 1,3-diketone hapten and the ε-amino group of the lysine of the catalytic antibody.

As discussed, in certain embodiments, certain antibodies that can be used in conjunction with compounds of the invention may require a reactive side chain in the antibody combining site. A reactive side chain may be present naturally or may be placed in an antibody by mutation. The reactive residue of the antibody combining site may be associated with the antibody, such as when the residue is encoded by nucleic acid present in the lymphoid cell first identified to make the antibody. Alternatively, the amino acid residue may arise by purposely mutating the DNA so as to encode the particular residue (e.g. WO 01/22922). The reactive residue may be a non-natural residue arising, for example, by biosynthetic incorporation using a unique codon, tRNA, and aminoacyl-tRNA as discussed herein. In another approach, the amino acid residue or its reactive functional groups (e.g., a nucleophilic amino group or sulfhydryl group) may be attached to an amino acid residue in the antibody combining site. Thus, covalent linkage with the antibody occurring "through an amino acid residue in a combining site of an antibody" as used herein means that linkage can be directly to an amino acid residue of an antibody combining site or through a chemical moiety that is linked to a side chain of an amino acid residue of an antibody combining site. In some embodiments, the amino acid is cysteine, and the reactive group of the side chain is a sulfhydryl group. In other embodiments, the amino acid residue is lysine, and the reactive group of the side chain is the ε-amino group. In some embodiments, the amino acid is Lys93 on the heavy chain according to Kabat numbering. In some embodiments, the amino acid is Lys-99 on HC h38C2 (SEQ ID NO:26).

Catalytic antibodies are one source of antibodies with suitable combining sites that comprise one or more reactive amino acid side chains. Such antibodies include aldolase antibodies, beta lactamase antibodies, esterase antibodies, and amidase antibodies.

One embodiment comprises an aldolase antibody such as the mouse monoclonal antibodies mAb 33F12 and mAb 38C2, as well as suitably chimeric and humanized versions of such antibodies (e.g. h38C2, SEQ ID NOs:25 and 26). Mouse mAb 38C2 (and h38C2) has a reactive lysine near to but outside HCDR3, and is the prototype of a new class of catalytic antibodies that were generated by reactive immunization and mechanistically mimic natural aldolase enzymes. See C. F. Barbas 3$^{rd}$ et al., Science 278:2085-2092 (1997). Other aldolase catalytic antibodies that may be used include the antibodies produced by the hybridoma 85A2, having ATCC accession number PTA-1015; hybridoma 85C7, having ATCC accession number PTA-1014; hybridoma 92F9, having ATCC accession number PTA-1017; hybridoma 93F3, having ATCC accession number PTA-823; hybridoma 84G3, having ATCC accession number PTA-824; hybridoma 84G11, having ATCC accession number PTA-1018; hybridoma 84H9, having ATCC accession number PTA-1019; hybridoma 85H6, having ATCC accession number PTA-825; hybridoma 90G8, having ATCC accession number PTA-1016. Through a reactive lysine, these antibodies catalyze aldol and retro-aldol reactions using the enamine mechanism of natural aldolases. Aldolase antibodies and methods of generating aldolase antibodies are disclosed in U.S. Pat. Nos. 6,210,938, 6,368,839, 6,326,176, 6,589,766, 5,985,626, and 5,733,75, which are incorporated herein by reference.

Compounds of the invention may also be formed by linking a compound of the invention to a reactive cysteine, such as those found in the combining sites of thioesterase and esterase catalytic antibodies. Suitable thioesterase catalytic antibodies are described by K. D. Janda et al., Proc. Natl. Acad. Sci. U.S.A. 91:2532-2536 (1994). Suitable esterase antibodies are described by P. Wirsching et al., Science 270: 1775-1782 (1995). Reactive amino acid-containing antibodies may be prepared by means well known in the art, including mutating an antibody combining site residue to encode for the reactive amino acid or chemically derivatizing an amino acid side chain in an antibody combining site with a linker that contains the reactive group.

The antibody may be a humanized antibody. Where compounds of the invention are covalently linked to the combining site of an antibody, and such antibodies are humanized, it is important that such antibodies be humanized with retention of high linking affinity for the Z group. Various forms of humanized murine aldolase antibodies are contemplated. One embodiment uses the humanized aldolase catalytic antibody h38c2 IgG1 or h38c2 Fab with human constant domains $C_K$ and $C_{\gamma}1$. C. Rader et al., J. Mol. Bio. 332:889-899 (2003) discloses the gene sequences and vectors that may be used to produce h38c2 Fab and h38c2 IgG1. Human germline $V_k$ gene DPK-9 and human $J_k$ gene JK4 were used as frameworks for the humanization of the kappa light chain variable domain of m38c2, and human germline gene DP-47 and human $J_H$ gene JH4 were used as frameworks for the humanization of the heavy chain variable domain of m38c2. FIG. 1 illustrates a sequence alignment between the variable light and heavy chains in m38c2, h38c2, and human germlines. h38c2 may utilize IgG1, IgG2, IgG3, or IgG4 constant domains, including any of the allotypes thereof. In certain embodiments of compounds of the invention wherein the antibody is h38c2 IgG1 with the G1m(f) allotype, Z binds to the side chain of the lysine residue at position 99 of the heavy chain. Another embodiment uses a chimeric antibody comprising the variable domains ($V_L$ and $V_H$) of h38c2 (SEQ ID NOS:27 and 28) and the constant domains from an IgG1, IgG2, IgG3, or IgG4. The antibody may be a full-length antibody, Fab, Fab', F(ab')$_2$, F$_v$, dsF$_v$, scF$_v$, V$_H$, V$_L$, diabody, or minibody comprising V$_H$ and V$_L$ domains from h38c2. The antibody may be an antibody comprising the V$_L$ and V$_H$ domains from h38c2 and a constant domain selected from the group consisting of IgG1, IgG2, IgG3, and IgG4. The antibody may be h38C2 IgG1 (SEQ ID NOS:25 and 26). The antibody may be a humanized version of a murine aldolase antibody comprising a constant region from a human IgG, IgA, IgM, IgD, or IgE antibody. In another embodiment, the antibody is a chimeric antibody comprising the V$_L$ and V$_H$ region from a murine aldolase antibody and a constant region from a human IgG, IgA, IgM, IgD, or IgE antibody. In some embodiments, the antibody comprises the $V_L$ and $V_H$ regions from m38C2 (SEQ ID NOS:29 and 30). In further embodiments, the antibody is a fully human version of a murine aldolase antibody comprising a polypeptide sequence from natural or native human IgG, IgA, IgM, IgD, or IgE antibody.

Various forms of humanized aldolase antibody fragments are also contemplated. One embodiment uses h38c2F(ab')$_2$. h38c2 F(ab')$_2$ may be produced by the proteolytic digestion of h38c2 IgG1. Another embodiment uses an h38c2 scFv comprising the $V_L$ and $V_H$ domains from h38c2 which are optionally connected by the intervening linker (Gly$_4$Ser)$_3$ (SEQ ID NO:31). As an alternative to humanization, human antibodies can be generated. For example, it is now possible to produce transgenic animals (e.g., mice) that are capable, upon immunization (or reactive immunization in the case of catalytic antibodies) of producing a full repertoire of human antibodies in the absence of endogenous immunoglobulin production.

Alternatively, phage display technology can be used to produce human antibodies and antibody fragments in vitro using immunoglobulin variable (V) domain gene repertoires from unimmunized donors. As indicated above, human antibodies may also be generated by in vitro activated B cells, e.g., U.S. Pat. Nos. 5,567,610 and 5,229,275.

Amino acid sequence modification(s) of the antibodies described herein are contemplated. For example, it may be desirable to improve the binding affinity and/or other biological properties of the antibody. Amino acid sequence variants of an antibody are prepared by introducing appropriate nucleotide changes into the antibody nucleic acid, or by peptide synthesis. Such modifications include, for example, deletions from, insertions into, and/or substitutions of residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites An antibody or antibody portion of the invention can be derivatized or linked to another molecule (e.g. another peptide or protein). In general, the antibodies or portion thereof is derivatized such that the ability of the linker to covalently conjugate to the antibody combining is not affected adversely by the derivatization or labelling. Accordingly, the antibodies and antibody portions of the invention are intended to include both intact and modified forms of the antibodies described herein. E.g. an antibody or antibody portion of the invention can be functionally linked (by chemical coupling, genetic fusion, noncovalent association or otherwise) to one or more other molecular entities, such as another antibody (e.g. a bispecific antibody or a diabody), a detection agent, a cytotoxic agent, a pharmaceutical agent, and/or a protein or peptide that can mediate associate of the antibody or antibody portion with another molecule (such as a streptavidin core region or a polyhistidine tag).

In other embodiments, the antibody or antigen binding portion thereof of the invention may be a fusion antibody or an antibody linked to another polypeptide. In some aspects, only the variable regions of the antibody are linked to the polypeptide. In some aspects, the antibody is covalently conjugated to a peptide in such a way so as to not interfere with the binding ability of the combining site.

The polypeptide may be a therapeutic agent, such as a targeting agent, peptide, protein agonist, protein antagonist, metabolic regulator, hormone, toxin, growth factor or other regulatory protein, or may be a diagnostic agent, such as an enzyme that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody.

One type of derivatized antibody is produced by crosslinking two or more antibodies (of the same type or of different types, e.g. to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate).

Another type of derivatized antibody is a labelled antibody. Useful detection agents with which an antibody or antibody portion of the invention may be derivatized include fluorescent compounds, including fluorescein, fluorescein isothiocyanate, rhodamine, 5-dimethylamine-1-napthalenesulfonyl chloride, phycoerythrin, lanthanide phosphors and the like. An antibody may also be labelled with enzymes that are useful for detection, such as horseradish peroxidase, galactosidase, luciferase, alkaline phosphatase, glucose oxidase and the like. When an antibody is labelled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody may also be labelled with biotin, and detected through indirect measurement of avidin or streptavidin binding. An antibody may be labelled with a magnetic agent, such as gadolinium. An antibody may also be labelled with a predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The antibody may also be derivatized with a chemical group such as polyethylene glycol (PEG), a methyl or ethyl group, or a carbohydrate group. These groups may be useful to improve the biological characteristics of the antibody, e.g. to increase serum half-life or to increase tissue binding.

Pharmaceutical Compositions

Another aspect of the invention provides pharmaceutical compositions comprising compositions and/or compounds of the invention. Agents comprising compositions of the invention may be formulated and administered systemically. Techniques for formulation and administration may be found in *Remington's Pharmaceutical Sciences*, 18$^{th}$ Ed., 1990, Mack Publishing Co., Easton, Pa.

For injection, compositions of the invention may be formulated in aqueous solutions, emulsions or suspensions, or nonaqueous solutions, suspensions, emulsions, dispersions or sterile powders or lyophilisates suitable for reconstitution into sterile injectable solutions or dispersions. Examples of suitable aqueous and nonaqueous diluents, solvents, and carriers include water, ethanol, polyols (such as propylene glycol, polyethylene glycol, glycerol, and the like), suitable mixtures thereof, and oils. Fluidity can be maintained or improved, for example, by the use of a coating such as lecithin, by the maintenance of the required particle size in the case of dispersions, and by the use of surfactants.

Compositions of the invention may be formulated in aqueous solutions containing physiologically compatible buffers such as citrate, acetate, histidine or phosphate. Where necessary, such formulations may also contain various tonicity adjusting agents, solubilizing agents and/or stabilizing agents (e.g., salts such as sodium chloride, sugars such as sucrose, mannitol, and trehalose, proteins such as albumin, amino acids such as glycine and histidine, surfactants such as polysorbates (Tweens), or cosolvents such as ethanol, polyethylene glycol and propylene glycol). Compositions of the invention may also comprise adjuvants, such as wetting agents, emulsifying and suspending agents, dispersing agents, and preserving agents. Compositions of the invention may also comprise suspending agents, such as agar-agar, aluminum metahydroxide, bentonite, ethoxylated isostearyl alcohols, microcrystalline cellulose, polyoxyethylene sorbitol and sorbitan esters, and tragacanth, or mixtures thereof.

Compositions of the invention may also comprise various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable compositions of the invention may be affected by the use of agents capable of delaying absorption, for example, aluminum monostearate and gelatin.

Compositions of the invention may contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as L-methionine ascorbic acid, sodium sulfite, or sodium hydrogen-sulfite), buffers (such as sodium acetate, lactate, borate, bicarbonate, Tris-HCl, citrates, phosphates, or other organic acids), bulking agents (such as mannitol or glycine), chelating agents (such as ethylenediamine tetraacetic acid (EDTA), DPTA), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants.

The formulation components may be present in concentrations that are acceptable to the site of administration. Buffers may be used to maintain the composition at physiological pH or at a slightly lower pH, typically within a pH range of from about 5 to about 8.

In some aspects, pharmaceutical compositions of the invention may be prepared wherein compounds of the invention are formulated for the controlled or sustained release of the compound. Examples include hyaluronic acid and the like, polymeric gels, beads, particles, injectable microspheres, liposomes, films, microcapsules, sustained release matrices, and implantable drug delivery devices.

In some aspects, pharmaceutical compositions of the invention are provided in single- or multi-chambered pre-filled syringes.

In some aspects, the invention provides for a kit comprising at least one compound or composition of the invention together with at least one additional ingredient suitable for use in a pharmaceutical composition. In some aspects, the invention provides for a kit comprising at least one compound or composition of the invention together with at least one means for delivery of said composition to a patient.

Compositions of the invention may be synthesized by covalently linking a FGF21 molecule to a linker and conjugating the linker to a combining site of a multivalent antibody. For example, a FGF21-linker conjugate, where the linker includes a diketone or AZD (β-lactam) reactive moiety, can be incubated with 0.5 equivalents of an aldolase antibody such as h38C2 IgG1 to produce a composition of the invention.

Methods of Use

For therapeutic use in humans, a human, humanized, or human chimeric antibody or antigen binding portion thereof is a preferred antibody form of the antibody portion of the compound or composition of the invention.

One aspect of the invention is a method for treating diabetes or a diabetes-related condition comprising administering a therapeutically effective amount of a composition of the invention to a subject suffering from diabetes or a diabetes-related condition.

Another aspect of the invention is a method for increasing insulin secretion in a subject comprising administering to the subject a therapeutically effective amount of a composition of the invention or a pharmaceutical derivative thereof.

Another aspect of the invention is a method for decreasing blood glucose levels in a subject comprising administering to the subject a therapeutically effective amount of a composition of the invention or a pharmaceutical derivative thereof.

Another aspect of the invention is a method for treating obesity in a subject comprising administering to the subject a therapeutically effective amount of a composition of the invention or a pharmaceutical derivative thereof.

Another aspect of the invention is a method for controlling or reducing weight levels in a subject comprising administering to the subject a therapeutically effective amount of a composition of the invention or a pharmaceutical derivative thereof.

Another aspect of the invention is a method for treating dislipidemia in a subject comprising administering to the subject a therapeutically effective amount of a composition of the invention or a pharmaceutical derivative thereof.

Another aspect of the invention is a method for treating hypertension in a subject comprising administering to the subject a therapeutically effective amount of a composition of the invention or a pharmaceutical derivative thereof.

Another aspect of the invention is a method for treating hepatosteaotosis in a subject comprising administering to the subject a therapeutically effective amount of a composition of the invention or a pharmaceutical derivative thereof.

Another aspect of the invention is a method for treating cardiovascular disease in a subject comprising administering to the subject a therapeutically effective amount of a composition of the invention or a pharmaceutical derivative thereof.

Another aspect of the invention is a method for reducing glucagon levels in a subject comprising administering to the subject a therapeutically effective amount of a composition of the invention or a pharmaceutical derivative thereof.

Another aspect of the invention is a method for reducing triglyceride levels in a subject comprising administering to the subject a therapeutically effective amount of a composition of the invention or a pharmaceutical derivative thereof.

Another aspect of the invention is a method for increasing non-esterified free fatty acid levels in a subject comprising administering to the subject a therapeutically effective amount of a composition of the invention or a pharmaceutical derivative thereof.

Another aspect of the invention is a method for reducing low density cholesterol levels in a subject comprising administering to the subject a therapeutically effective amount of a composition of the invention or a pharmaceutical derivative thereof.

Another aspect of the invention is a method for reducing C-reactive protein levels in a subject comprising administering to the subject a therapeutically effective amount of a composition of the invention or a pharmaceutical derivative thereof.

Another aspect of the invention is a method for reducing fructosamine levels in a subject comprising administering to the subject a therapeutically effective amount of a composition of the invention or a pharmaceutical derivative thereof.

Another aspect of the invention is a method for controlling glycemic control in a subject comprising administering to the subject a therapeutically effective amount of a composition of the invention or a pharmaceutical derivative thereof.

Another aspect of the invention is a method for increasing levels of adipsin in a subject comprising administering to the subject a therapeutically effective amount of a composition of the invention or a pharmaceutical derivative thereof.

Another aspect of the invention is a method for increasing levels HDL in a subject comprising administering to the subject a therapeutically effective amount of a composition of the invention or a pharmaceutical derivative thereof.

In some aspects, the invention provides for a method of treating diabetes related conditions, obesity, dislipidemia, hypertension, hepatosteaotosis, or cardiovascular disease; or controlling or reducing weight levels; or controlling glycemic control; or increasing insulin secretion, or levels of non-esterified free fatty acids, HDL or adipsin; or reducing levels of blood glucose, glucagon, triglyceride, fructosamine, low density cholesterol, or C-reactive protein; comprising administering a therapeutically effective amount of a compound or a pharmaceutical composition of the invention to a subject.

In some aspects, the invention provides for the use of a composition or a pharmaceutical composition of the invention in the preparation of a medicament for treating diabetes related conditions, obesity, dislipidemia, hypertension, hepatosteaotosis, or cardiovascular disease; or controlling or reducing weight levels; or controlling glycemic control; or increasing insulin secretion, HDL, or non-esterified free fatty acid levels; or reducing levels of blood glucose, glucagon, triglyceride, fructosamine, low density cholesterol, or C-reactive protein.

The term "therapeutically effective dose," as used herein, means that amount of compound, composition or pharmaceutical composition of the invention that elicits the biological or medicinal response in a tissue system, animal, or human being sought by a researcher, medical doctor, or other clinician, which includes alleviation of the symptoms of a disease or disorder being treated.

Methods of Administration and Dosages

Administration routes of composition of the invention may include parenteral delivery, including intramuscular, SC, or intramedullary injections, as well as intrathecal, direct intraventricular, IV, and intraperitoneal delivery. In some embodiments, administration is intravenous. The compositions of the invention may be administered through any of the parenteral routes either by direct injection of the formulation or by infusion of a mixture of the formulation of the composition of the invention with an infusion matrix such as normal saline, D5W, lactated Ringers solution or other commonly used infusion media.

In treating mammals, including humans, having diabetes or a diabetes-related condition (or in some aspects, one or more of the following conditions: diabetes, obesity, dislipidemia, hypertension, hepatosteaotosis, cardiovascular disease, high blood glucose, low insulin levels, or any of the conditions discussed herein or a condition associated with a symptom herein discussed), a therapeutically effective amount of a composition of the invention or a pharmaceutically acceptable derivative is administered. For example, a composition of the invention may be administered as a daily IV infusion from about 0.1 mg/kg body weight to about 15 mg/kg body weight. Accordingly, some embodiments provide a dose of about 0.5 mg/kg body weight. Other embodiments provide a dose of about 0.75 mg/kg body weight. Other embodiments provide a dose of about 1.0 mg/kg body weight. Other embodiments provide a dose of about 2.5 mg/kg body weight. Other embodiments provide a dose of about 5 mg/kg body weight. Other embodiments provide a dose of about 10.0 mg/kg body weight. Other embodiments provide a dose of about 15.0 mg/kg body weight. Doses of a composition of the invention or a pharmaceutically acceptable derivative should be administered in intervals of from about once per day to 2 times per week, or alternatively, from about once every week to once per month. In some embodiments, a dose is administered to achieve peak plasma concentrations of a composition of the invention according to the invention or a pharmaceutically acceptable derivative thereof from about 0.002 mg/ml to 30 mg/ml. This may be achieved by the sterile injection of a solution of the administered ingredients in an appropriate formulation (any suitable formulation solutions known to those skilled in the art of chemistry may be used). Desirable blood levels may be maintained by a continuous infusion of composition of the invention according to the invention as ascertained by plasma levels measured by a validated analytical methodology.

One method for administering a composition of the invention to an individual comprises administering a FGF21-linker conjugate to the individual and allowing it to form a covalent compound with a combining site of an appropriate antibody in vivo. The antibody portion of a composition of the invention that forms in vivo may be administered to the individual before, at the same time, or after administration of the FGF21-linker conjugate. Alternatively, or in addition, an antibody may be present in the circulation of the individual following immunization with an appropriate immunogen. For example, catalytic antibodies may be generated by immunizing with a reactive intermediate of the substrate conjugated to a carrier protein. In particular, aldolase catalytic antibodies may be generated by administering with keyhole limpet hemocyanin linked to a diketone moiety.

The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g. orally, through injection by SC, IV, intraperitoneal, intracerebral (intraparenchymal), intracerebroventricular, intramuscular, intraocular, intraarterial, intraportal, or intralesional routes; by sustained release systems; or by implantation devices. Where desired, the compositions can be administered by bolus injection or continuously by infusion, or by implantation device.

Alternatively or additionally, the composition can be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

Combination Therapies

In another aspect of the invention, a composition of the invention may be used in combination with other therapeutic agents used to treat diabetes or diabetes-related conditions, or to increase insulin secretion or decrease blood glucose levels, or to treat any of the conditions discussed herein. In one embodiment, a composition of the invention may be administered in combination with insulin, such as for example synthetic human insulin, including rapid acting, short-acting, intermediate-acting, or long-lasting insulin. In other embodiments, a composition of the invention may be administered in combination with compounds belonging to the α-glucosidase inhibitor, sulfonylurea, meglitinide, biguanide, or thiazolidinedione (TZD) families. Compositions of the invention may also be administered in combination with metabolism-modifying proteins or peptides such as glucokinase (GK), glucokinase regulatory protein (GKRP), uncoupling proteins 2 and 3 (UCP2 and UCP3), glucagon, glucagon like peptide 1 and 2 (Glp1 and Glp2), an exendin, (such as exendin-4), gastric inhibitory polypeptide (GIP), Glp2 peroxisome proliferator-activated receptor α (PPARα), leptin receptor (OB-Rb), DPP-IV inhibitors, sulfonylureas, or other incretin peptides. One of ordinary skill in the art would know of a wide variety of agents that are currently used in the treatment of diabetes or diabetes-related conditions.

In order to evaluate potential therapeutic efficacy of a composition of the invention or a pharmaceutically acceptable derivative thereof in combination with other therapeutic agents used to treat diabetes or diabetes-related conditions, increase insulin secretion, or decrease blood glucose levels, these combinations may be tested using methods known in the art. For example, the ability of a combination of a composition of the invention and another therapeutic agent to increase insulin secretion may be measured using an in vitro glucose-stimulated insulin secretion assay. In such an assay, pancreatic β cells are treated with various concentrations of glucose for a set period of time, and insulin levels are measured using methods known in the art, such as for example a radioimmunoassay. The effect of compositions of the invention and other therapeutic agents on insulin secretion may also be measured in vivo, by administering the agents directly to a subject and measuring insulin levels in bodily fluid samples at various time points. Methods for administering known therapeutic agents to a subject for use in combination therapies will be well known to clinical health care providers.

Effective dosages of composition of the invention to be administered may be determined through procedures well known to those in the art which address such parameters as biological half-life, bioavailability, and toxicity. Effective amounts of therapeutic agents to be used in combination with composition of the invention or pharmaceutically acceptable derivatives thereof are based on the recommended doses known to those skilled in the art for these agents. These recommended or known levels will preferably be lowered by 10% to 50% of the cited dosage after testing the effectiveness of these dosages in combination with a composition of the invention or a pharmaceutically acceptable derivative. It should be noted that the attending physician would know how and when to terminate, interrupt, or adjust therapy to lower dosage due to toxicity, bone marrow, liver or kidney dysfunctions or adverse drug-drug interaction. The attending physician would also know to adjust treatment to higher levels if the clinical response is inadequate (precluding toxicity).

A therapeutically effective dose refers to that amount of the compound sufficient to result in amelioration of symptoms or a prolongation of survival in a patient. The effective in vitro concentration of a composition of the invention may be determined by measuring the $EC_{50}$. Toxicity and therapeutic efficacy of such agents in vivo can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e. the concentration of the test compound which achieves a half-maximal inhibition of RT production from infected cells compared to untreated control as determined in cell culture). Such information can be used to more accurately determine useful doses in humans. Levels in plasma may be measured, for example, by high performance liquid chromatography (HPLC).

In those embodiments wherein compositions of the invention are administered in combination with other therapeutic agents, the combined effect of the agents can be calculated by the multiple drug analysis method of Chou and Talalay (T. C. Chou and P. Talalay, Adv. Enzyme Regul. 22:27-55 (1984)) using the equation:

$$CI = \frac{D_1}{(Dx)_1} + \frac{D_2}{(Dx)_2} + \frac{\alpha D_1 D_2}{(Dx)_1 (Dx)_2}$$

where CI is the combination index, $(Dx)_1$ is the dose of drug 1 required to produce x percent effect alone, $D_1$ is the dose of drug 1 required to produce the same x percent effect in combination with $D_2$. The values of $(Dx)_2$ and $(D)_2$ are similarly derived from drug 2. The value of α is determined from the plot of the dose effect curve using the median effect equation:

$$\frac{fa}{fu} = \left(\frac{D}{Dm}\right)^m$$

where fa is the fraction affected by dose D, fu is the uninfected fraction, Dm is the dose required for 50% effect and m is the slope of the dose-effect curve. For mutually exclusive drugs (i.e., similar modes of action), both drugs alone and their parallel lines in the median effect plot. Mutually nonexclusive drugs (i.e., independent mode of action) will give parallel lines in the median effect plot, but in mixture will give a concave upward curve. If the agents are mutually exclusive α is 0, and if they are mutually non-exclusive, α is 1. Values obtained assuming mutual non-exclusiveness will always be slightly greater than mutually exclusive drugs. CI values of <1 indicate synergy, values>1 indicate antagonism and values equal to 1 indicate additive effects. The combined drug effects may also be calculated using the CalcuSyn software package from Biosoft (Cambridge, UK).

The compounds according to the invention may be solvated, especially hydrated. Hydration may occur during manufacturing of the compounds or compositions comprising the compounds, or the hydration may occur over time due to the hygroscopic nature of the compounds. The compounds of the invention may be lyophilized.

The invention also provides for stereoisomers, tautomers, solvates, prodrugs, and pharmaceutically acceptable salts of compounds of the invention. The invention also provides for compounds according to any of the sequences disclosed herein.

Sequences

| SEQ ID NO: | Description | Sequence |
|---|---|---|
| 1 | FGF21 genus x1 = H or absent (H/Δ), x146 = L/P. | xPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAXPEPP GILAPQPPDV GSSDPLSMVG PSQGRSPSYAS |
| 2 | FGF21ΔH: | H1 absent (ΔH1), L146. |
| 3 | FGF21 Cys mutant genus 1: | x1 = H/Δ, x79 = D/C, x125 = H/C, x129 = A/C, x146 = P/L |
| 4 | FGF21 Cys mutant genus 2 | x1 = H/Δ, x125 = C/H, x129 = A/C, x146 = L/P |
| 5 | FGF21 H125C genus: | x1 = H/Δ, H125C, x146 = L/P |
| 6 | FGF21ΔH-H125C-L146: | ΔH1 H125C L146 |
| 7 | FGF21ΔH-H125C: | ΔH1 H125C P146 |
| 8 | FGF21 A129C genus: | x1 = H/Δ, A129C, x146 = L/P |
| 9 | FGF21ΔH-A129C-L146: | ΔH1, A129C, L146 |
| 10 | FGF21ΔH-A129C: | ΔH1, A129C, P146 |
| 11 | FGF21 D79C genus: | x1 = H/Δ, D79C, x146 = P/L |
| 12 | FGF21ΔH-D79C: | ΔH1, D79C, P146 |
| 13 | FGF21ΔH-D79C-L146: | ΔH1, D79c, L146 |
| 14 | FGF21ΔH-L86C: | ΔH1, L86C, L146 |
| 15 | FGF21ΔH-T40C: | ΔH1, T40C, L146 |
| 16 | FGF21ΔH-H1C: | H1C, L146 |
| 17 | FGF21 Lys mutant genus: | x1 = H/Δ, x56, x59, x122 = K/R, R69, x146 = L/P |
| 18 | FGF21ΔH-K56: | ΔH1-K56-K59R-K69R-K122R-L146 |
| 19 | FGF21ΔH-K59 | ΔH1-K56R-K69R-K122R-L146 |
| 20 | FGF21ΔH-K69: | ΔH1-K56R-K59R-K122R-L146 |
| 21 | FGF21ΔH-K122: | ΔH1-K56R-K59R-K69R-L146 |
| 22 | FGF21ΔH-Knull-P2: | ΔH1-K56R-K59R-K69R-K122R-L146 |
| 23 | FGF21ΔH-Knull-H1K: | ΔH1-H1K-K56R-K59R-K69R-K122R-L146 |
| 24 | FGF21ΔH-Knull-S181K: | ΔH1-K56R-K59R-K69R-K122R-L146-S181K |
| 25 | h38C2 light chain | ELQMTQSPSS LSASVGDRVT ITCRSSQSLL HTYGSPYLNW YLQKPGQSPK LLIYKVSNRF SGVPSRFSGS GSGTDFTLTI SSLQPEDFAV YFCSQGTHLP YTFGGGTKVE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 26 | h38C2 heavy chain | EVQLVESGGG LVQPGGSLRL SCAASGFTFS NYWMSWVRQS PEKGLEWVSE IRLRSDNYAT HYAESVKGRF TISRDNSKNT LYLQMNSLRA EDTGIYYCKT YFYSFSYWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKRVEPKS CDKTHTCPPC PAPELLGGPS VFLFPPKPKD TLMISRTPEV TCVVVDVSHE DPEVKFNWYV DGVEVHNAKT KPREEQYNST |

-continued

| SEQ ID NO: | Description | Sequence |
|---|---|---|
| | | YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 27 | VL h38C2 | |
| 28 | VH h38C2 | |
| 29 | VL m38C2 | |
| 30 | VH m38C2 | |
| 31 | (Gly$_4$ Ser)$_3$ | |
| 32 | FGF21 28 aa N-terminal leader sequence | |
| 33 | FGF21 209 residue sequence, L174 (L146) isoform | |

SEQ ID NO:1 shows the 181-residue expressed protein where H$^1$ is optional and residue 146 may be L or P. Residue positions tested for conjugation are underlined and in bold. The numbering for SEQ ID NO:1 is used throughout.

The amino acid sequence of the light and heavy chain (SEQ ID NOs:25 and 26, respectively) of one embodiment of a humanized 38c2 IgG1 are also shown. The variable regions (VC and VH) are underlined and complementarity determining regions (CDRs) presented in bold. Lysine 99, whose side chain covalently combines with the linkers described herein, is adjacent HC CDR3.

BRIEF DESCRIPTION OF THE DRAWINGS

FIG. 1. Amino acid sequence alignment of the variable domains of m38c2, h38c2, and human germlines. Framework regions (FR) and CDRs are defined according to Kabat et al. Asterisks mark differences between m38c2 and h38c2 or between h38c2 and the human germlines.

FIGS. 4A and 4B. Glucose area under the curve (AUC) during oral glucose tolerance test (OGTT) in ob/ob mice given a single SC dose (Mean Glucose AUC (% of vehicle control) in square brackets):Vehicle [100], FGF21ΔH (1 mg/kg [74]), FGF21ΔH (0.6 mg/kg [103]) (not shown in FIG. 4B for clarity), Ab-FGF21ΔH-H125C (3 mg/kg [66] and 1 mg/kg [87]) (conjugated with L1), Ab-FGF21ΔH-K59 (3 mg/kg [105]) (conjugated with L5), Ab-FGF21ΔH-Knull-H1K (3 mg/kg [100]) (conjugated with L5), Lean control [56]. *P<0.05, **P<0.01 vs PBS by one-way ANOVA.

FIGS. 9A-E and 9H-9P. Values represent mean±SEM, n=5 for AB-L1-FGF21ΔH-A129C 1.5 mg/kg and FGF21ΔH (control protein), n=6 for AB-L1-FGF21ΔH-A129C 0.15 mg/kg and vehicle group. For AB-L1-FGF21ΔH-A129C treated groups significance at each timepoint is calculated vs. vehicle. For the FGF21ΔH group significance at each timepoint is calculated vs. baseline. Significance values are a=p<0.05, b=p<0.01, c=p<0.005 and d=p<0.001. Y axis shows changes from the baseline.

FIG. 9A. Effect of AB-L1-FGF21ΔH-A129C on body weight.

FIG. 9B. Effect of AB-L1-FGF21ΔH-A129C on fasted plasma glucose.

FIG. 9C. Effect of AB-L1-FGF21ΔH-A129C on fasted plasma insulin.

FIG. 9D. Effect of AB-L1-FGF21ΔH-A129C on fasted plasma fructosamine.

FIG. 9E. Effect of AB-L1-FGF21ΔH-A129C on fasted plasma glucagon.

FIG. 9i. Effect of AB-L1-FGF21ΔH-A129C on fasted plasma triglycerides.

FIG. 9J. Effect of AB-L1-FGF21ΔH-A129C on fasted plasma free fatty acids.

FIG. 9K. Effect of AB-L1-FGF21ΔH-A129C on fasted plasma low-density lipoprotein cholesterol.

FIG. 9L. Effect of AB-L1-FGF21ΔH-A129C on fasted plasma total ketone bodies.

FIG. 9M. Effect of AB-L1-FGF21ΔH-A129C on fasted plasma adiponectin.

FIG. 9N. Effect of AB-L1-FGF21ΔH-A129C on fasted plasma C-reactive protein.

FIG. 9o. Effect of AB-L1-FGF21ΔH-A129C on fasted plasma leptin.

FIG. 9P. Effect of AB-L1-FGF21ΔH-A129C on fasted plasma adipsin.

EXAMPLES

Figure 2A:
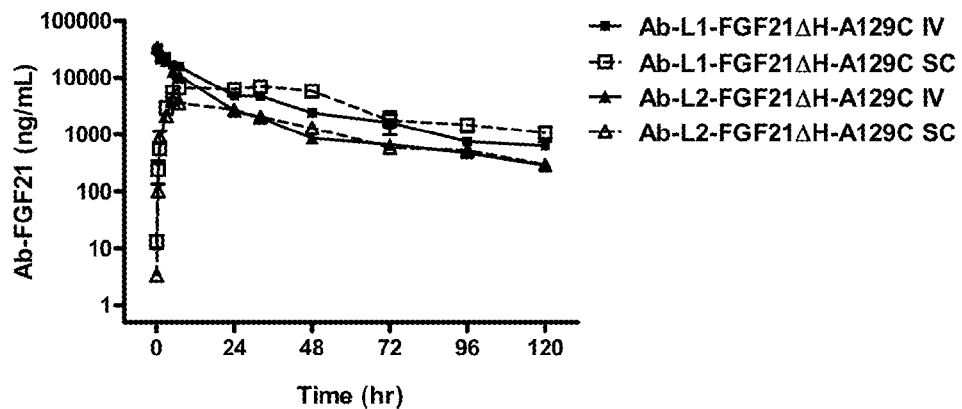
FIGS. 2A, 2B, and 2C. Single dose mouse pharmacokinetic studies with Ab-FGF21ΔH-A129C conjugated with Linker-1 (L-1) in comparison with L-2, L-3, or L-4. Young adult male Swiss-Webster mice were dosed either IV or SC at 3 mg/kg. In all cases, the conjugate with L-1 performed better with respect to half-life (~33 hrs SC and IV for L-1 conjugate, 13-23 hrs SC and 22-37 hrs IV for L-2, -3, and -4 conjugates) and/or SC bioavailability (~100% for L-1 conjugate, 48-53% for L-2, -3, or -4 conjugates).

The versatility of the invention is illustrated by the following Examples, which illustrate typical embodiments of the invention and are not limiting of the claims or specification in any way.

Example 1

Identifying Optimal Tether Site on FGF-21

A study was undertaken to identify the optimal site for conjugation of FGF21 via a linker to a catalytic antibody combining site. Two conjugation strategies were considered: conjugation through a surface lysine side-chain, and conjugation through a surface cysteine side-chain. Generally, globular proteins do not have unpaired cysteine residues on their surface, and thus incorporation of a single cysteine in the protein surface can be used to engineer in a single site for specific conjugation. However, the mutation of surface residues with cysteine can often cause problems such as intermolecular dimerization, mis-pairing of native disulphide bonds, and interference with receptor binding. For these reasons, protein conjugation is most commonly affected through lysine residues.

Homology Modelling of FGF21 Receptor and its Activation Mechanism

FGF21 binds to both FGFR1c and FGFR4, but the receptor complex can be activated only through FGFR1c. Although FGFR1b and FGFR1c share 87% identity (FGFR1b is identical to FGFR1c except for the 111b/c alternative splicing region), FGF21 specifically recognizes only FGFR1c. Here, homology modelling of the complex structure of FGF21-FGFR1c was performed by using the FGFR2-FGFR1c crystal structure as a template. MOE software was used for homology modelling and structural analyses. The activation of the receptor requires another cell-surface receptor, βKlotho. βKlotho has two domains which are very similar (~35% identical) to human cytosolic 6-glucosidase. The human βKlotho structure was modelled by using human cytosolic β-glucosidase, and the structure in the modelled structure of FGF21-FGFR1c aligned. This modelled complex structure provided rational guidelines for the optimum lysine conjugation sites and optimum cysteine residue incorporation in FGF21, which should not interrupt the binding interfaces between FGF21 and FGFR1c and between FGF21 and βKlotho.

The following criteria were used for conjugation site selection: (1) residues should be exposed to the solvent in the structure as much as possible; (2) residues should be far from the disulphide bond; (3) residues should be far from the receptor and β-Klotho binding surfaces.

Exposure to solvent can be assessed based on the accessible surface area (ASA). Calculation of ASA from the modelled structure of FGF21 was done with CCP4 software (The CCP4 Suite: Programs for Protein Crystallography". (1994) Acta Cryst. D50, 760-763) and an in-house program. Briefly the program in CCP4 calculates a value in square angstroms per residue in its log file. In order to calculate the fraction of ASA (fASA), an in-house program was used to normalize ASA per residue. Table 1 shows residues of ASA as well as fASA. Residues whose side chain is predicted to be obscured the surface are not included. Column 1 is the amino acid name, 2 is the residue number, 3 is ASA (as square angstrom), 4 is the fraction exposed. The fASA value defines the accessibility of solvent to the amino acid residue in a given polypeptide. A fASA value close to zero indicates that the residue is predicted to be inaccessible to solvent, suggesting that it is more unlikely to be accessible to the linkers for conjugation. An absolute minimum fASA value of 0.3 was used, with surface area values>1.00 suggestive of particularly likely candidate conjugation sites.

Based on the ASA analysis, K122 (surface area of 164.4) and K59 (surface area of 117.2) were considered the most promising candidate sites for conjugation. K69 (surface area 91) and K56 (surface area 73) were also conjugated for comparative purposes.

TABLE 1

Comparison of surface residues of FGF21

| Amino Acid | Residue Number | Surface Area | Fraction Exposed |
|---|---|---|---|
| GLY | 14 | 105.2 | 1.25387 |
| GLN | 15 | 158.5 | 0.83774 |
| VAL | 16 | 81.5 | 0.50216 |
| ARG | 17 | 91.6 | 0.36743 |
| ARG | 19 | 78.6 | 0.31528 |
| ALA | 26 | 93.9 | 0.8067 |
| GLN | 27 | 126.5 | 0.66861 |
| GLN | 28 | 169.4 | 0.89535 |
| THR | 29 | 64.2 | 0.43349 |
| GLU | 30 | 103.9 | 0.55502 |
| GLU | 37 | 117.1 | 0.62553 |
| ASP | 38 | 90.5 | 0.58237 |
| THR | 40 | 49.8 | 0.33626 |
| GLY | 43 | 38.1 | 0.45411 |
| ALA | 45 | 93.6 | 0.80412 |
| ASP | 46 | 95 | 0.61133 |
| PRO | 49 | 82.4 | 0.56906 |
| GLN | 54 | 66.8 | 0.35307 |
| LYS | 56 | 73 | 0.35181 |
| ALA | 57 | 46.6 | 0.40034 |
| LEU | 58 | 82.7 | 0.41768 |
| LYS | 59 | 117.2 | 0.56482 |
| PRO | 60 | 153.8 | 1.06215 |
| GLY | 61 | 27.9 | 0.33254 |
| VAL | 68 | 58.8 | 0.36229 |

TABLE 1-continued

Comparison of surface residues of FGF21

| Amino Acid | Residue Number | Surface Area | Fraction Exposed |
|---|---|---|---|
| LYS | 69 | 91 | 0.43855 |
| SER | 71 | 69 | 0.54893 |
| ARG | 77 | 129.4 | 0.51905 |
| PRO | 78 | 98.9 | 0.68301 |
| ASP | 79 | 109.8 | 0.70656 |
| TYR | 83 | 84.4 | 0.35418 |
| LEU | 86 | 119.4 | 0.60303 |
| HIS | 87 | 104.8 | 0.52796 |
| PHE | 88 | 123 | 0.55083 |
| ASP | 89 | 50.7 | 0.32626 |
| PRO | 90 | 107.5 | 0.7424 |
| GLU | 91 | 121.5 | 0.64904 |
| ARG | 96 | 92.6 | 0.37144 |
| LEU | 98 | 114 | 0.57576 |
| LEU | 99 | 113.2 | 0.57172 |
| GLU | 101 | 182.1 | 0.97276 |
| ASP | 102 | 94.6 | 0.60875 |
| GLY | 103 | 56.1 | 0.66865 |
| GLN | 108 | 72.6 | 0.38372 |
| GLU | 110 | 132.4 | 0.70727 |
| ALA | 111 | 62.7 | 0.53866 |
| GLY | 113 | 56.8 | 0.677 |
| LYS | 122 | 164.4 | 0.79229 |
| PRO | 124 | 67.4 | 0.46547 |
| HIS | 125 | 168.4 | 0.84836 |
| ARG | 126 | 131.4 | 0.52708 |
| PRO | 128 | 91.3 | 0.63053 |
| ALA | 129 | 78.8 | 0.67698 |
| ARG | 131 | 225.5 | 0.90453 |
| GLY | 132 | 65.8 | 0.78427 |
| PRO | 133 | 84.9 | 0.58633 |
| ARG | 135 | 106.2 | 0.42599 |
| GLY | 141 | 30.4 | 0.36234 |
| LEU | 142 | 69.1 | 0.34899 |
| PRO | 143 | 71.4 | 0.49309 |
| ALA | 145 | 86.4 | 0.74227 |
| LEU | 146 | 123.3 | 0.62273 |
| PRO | 147 | 131.1 | 0.90539 |
| GLU | 148 | 67.3 | 0.35951 |
| PRO | 149 | 170 | 1.17403 |

Example 2

Generation of FGF21 Proteins and Mutants

FGF21 cDNA was purchased from ATCC. Mammalian and bacterial expression vectors were constructed by using pcDNA3.1 (Invitrogen®) and pET21b (EMD), respectively. For the mutational variants of FGF21, mutations were introduced into the expression vectors using a QuikChange® site-directed mutagenesis kit (Stratagene®). The presence of the desired mutations was verified by DNA sequencing.

For mammalian expression, HEK293F cells (Invitrogen®) were transfected with the mammalian expression vector of FGF21 using 293fectin reagent (Invitrogen®) and grown in serum-free medium. Sterile-filtered, conditioned media were dialyzed against buffer A (20 mM Tris-HC1, pH 7.5) and loaded onto a HiTrap Q column (GE Healthcare®) preequilibrated with buffer A. FGF21 protein was eluted with a linear gradient from buffer A to buffer B (20 mM Tris-HC1, pH 7.5, and 100 mM NaCl). The pooled fraction was concentrated and loaded onto Sephadex 300 with phosphate buffer saline (PBS, pH 7.4). The resulting protein solution was concentrated and stored below −80° C. The purity was confirmed by SDS-PAGE and RP-HPLC.

For production of FGF21ΔH from *E. coli*, the bacterial expression vector was transformed into the host strain BL21-

(DE3)-RIL (Stratagene®). The transformed cells were grown in 1 liter of LB medium at 37° C., and expression was initiated by addition of 1 mM isopropyl β-D-thiogalactopyranoside. After 4 hr, cells were harvested and frozen at −20° C. The frozen cell paste was suspended in lysis buffer (50 mM Tris, 10 mM EDTA, pH 7.5), and passed through the microfluidizer 4 times. After 30 min centrifugation at 17,000×g, 4° C., the inclusion body (IB) containing pellet was resuspended in 50 mM Tris, pH 7.5. The washed IB slurry was centrifuged (30 min, 17,000×g, 4° C.). The IB pellet was stored at −80° C. The frozen IB pellet was solubilized with 7 M urea, 5 mM DTT and 50 mM bis-tris propane, pH 10.5 at 1 to 10 mg/ml FGF21 and stirred for 1 hr to dissolve and reduce protein. The solubilized IB was then diluted 10 times into 50 mM Bis-Tris propane, pH 8.0. Final protein concentration was 0.1 to 1 mg/mL. The solution was stirred for ~2 days and dialyzed against 4 liters of 20 mM Tris-HCl, pH7.5. The protein solution was centrifuged at 14,000×g for 30 min. The supernatant was loaded to HiTrap Q HP (GE Healthcare®) and equilibrated with buffer A (see above). Unbound bacterial proteins were washed with buffer A and FGF21 protein was eluted with a linear gradient of buffer B. The FGF21 fraction was then loaded onto a HiTrap chelating HP column (GE Healthcare®) pre-equilibrated with PBS buffer. FGF21 protein was eluted with a linear gradient from PBS to PBS buffer plus 100 mM imidazole (pH was adjusted to 7.4). The fractions were collected and concentrated (up to 50 mg/mL) and the protein solution applied to a size exclusion column (Hiload 26/60, superdex 300) equilibrated with PBS (Gibco®, pH7.4). Purified protein was sterilized by 0.22 μm filter and stored at −80°. Typical yield of FGF21ΔH from 8 L culture media was 600~700 mg. Typical purity was >95%. Typical endotoxin level was ~1 EU/mg. The cysteine and lysine-to-arginine mutants of FGF21 were produced and purified in a similar manner to FGF21ΔH. A typical yield of purified protein was 350~400 mg. Free cysteine was confirmed by using Ellman's reagent.

Example 3

Synthesis of Linker 1

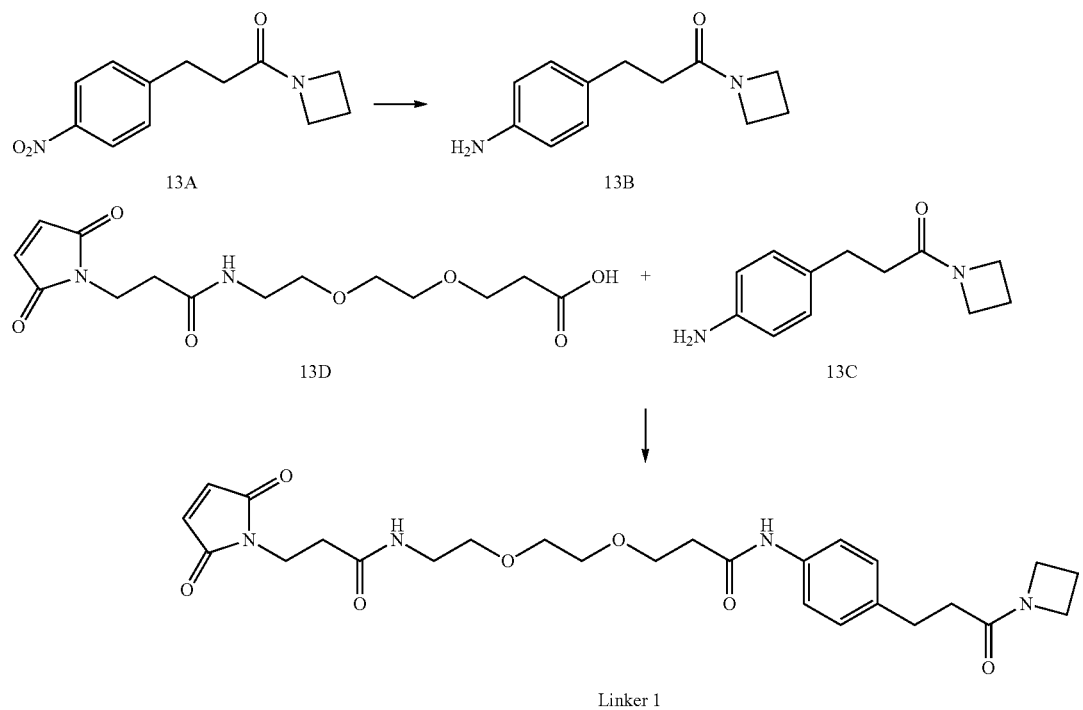

Linker 1

Synthesis of Linker 1: Palladium on carbon (e.g. about 1.0 g, about 0.47 mmol) was added in one portion followed by hydrochloric acid (e.g. about 2.5 mL, about 30.2 mmol) dropwise to a suspension of 13A (e.g. about 5 g, about 20.1 mmol) in methanol (e.g. about 200 mL) at about 35° C. under an atmosphere of nitrogen. Hydrogen was slowly bubbled in to the solution at about 35° C. and the solution was stirred for approximately about 2 hrs at that temperature. The solid was filtered through a bed of celite, and collected. The filtrate was concentrated under reduced pressure and the solid was dried under vacuum to give 13B as hydrochloride salt. Compound 13B was mixed with dichloromethane (e.g. about 200 mL) and saturated solution of sodium bicarbonate (for example, about 250 mL), and the dichloromethane layer was separated. The dichloromethane layer was washed with saturated sodium chloride (e.g. about 250 mL) and dried on sodium sulphate. The organic layer was filtered, concentrated under reduced pressure and purified using flash chromatography (SiO$_2$, about 60% ethyl acetate in hexanes) to give a yield of about 68% (e.g. about 2.94 g) of 13C. A solution of 13C (e.g. about 4.65 g, about 21.3 mmol), 13D (e.g. about 7.00 g, about 21.3 mmol) N-(3-dimethylaminopropyl)-N'-ethylcarbodiimide hydrochloride (e.g. about 3.3 g, about 21.3 mmol), and N,N-diisopropylethylamine (e.g. about 2.75 g, about 21.3 mmol) in dichloromethane (e.g. about 200 mL) at about 0° C. under nitrogen was stirred for 5 mins and at room temperature for about 4 hrs. The organic layer was washed with dilute sodium bicarbonate solution, and, saturated sodium chloride solution, concentrated under vacuum, and purified using flash chromatography (SiO₂, acetonitrile) to afford Linker 1 (e.g. about 8.25 g a yield of about 73%).
Example 4
Synthesis of Linker 2
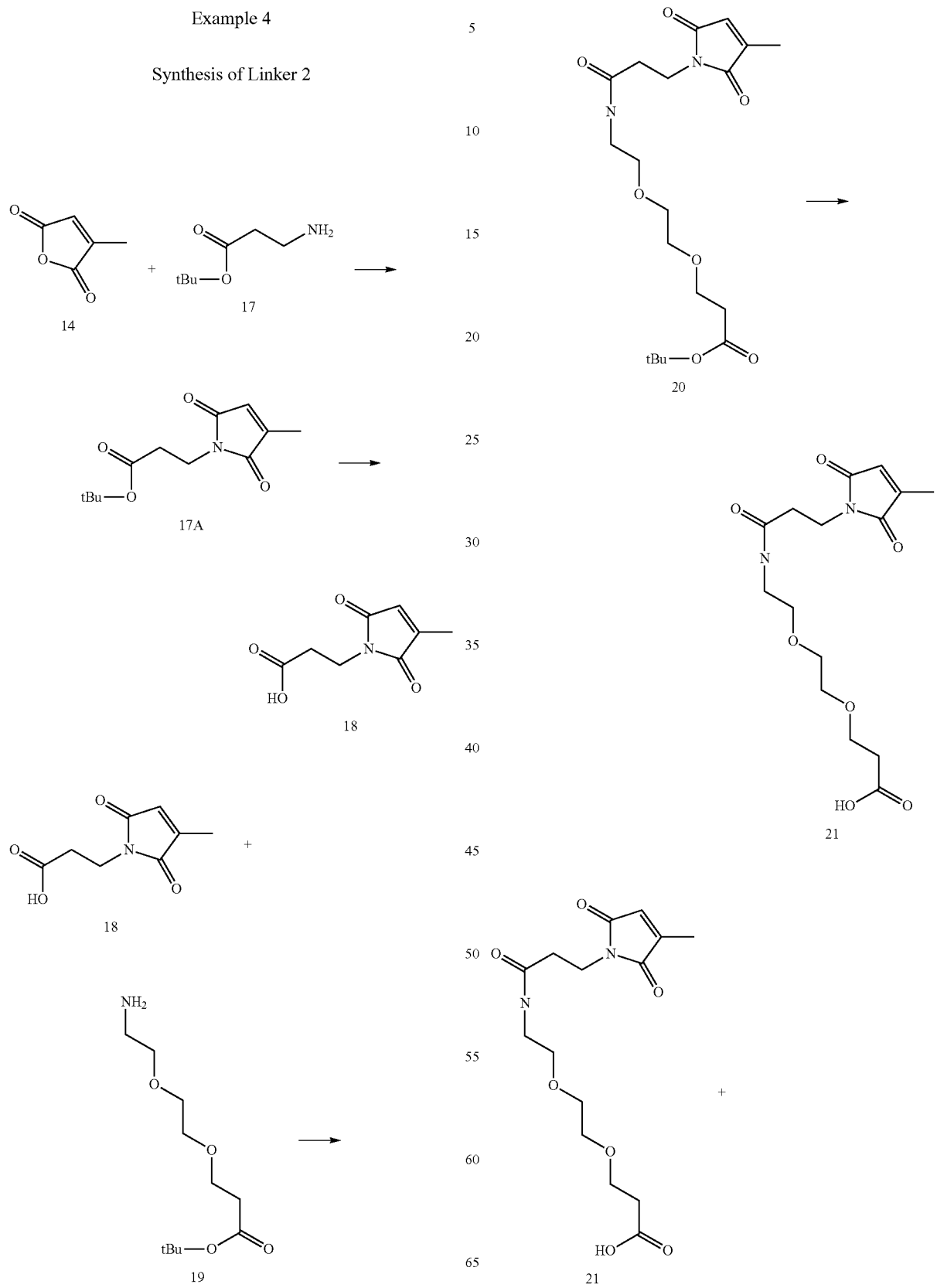

-continued

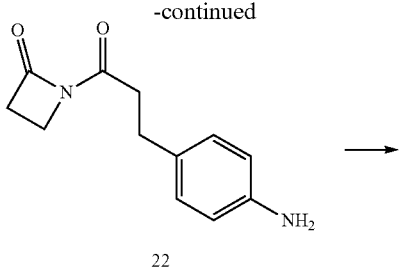
22

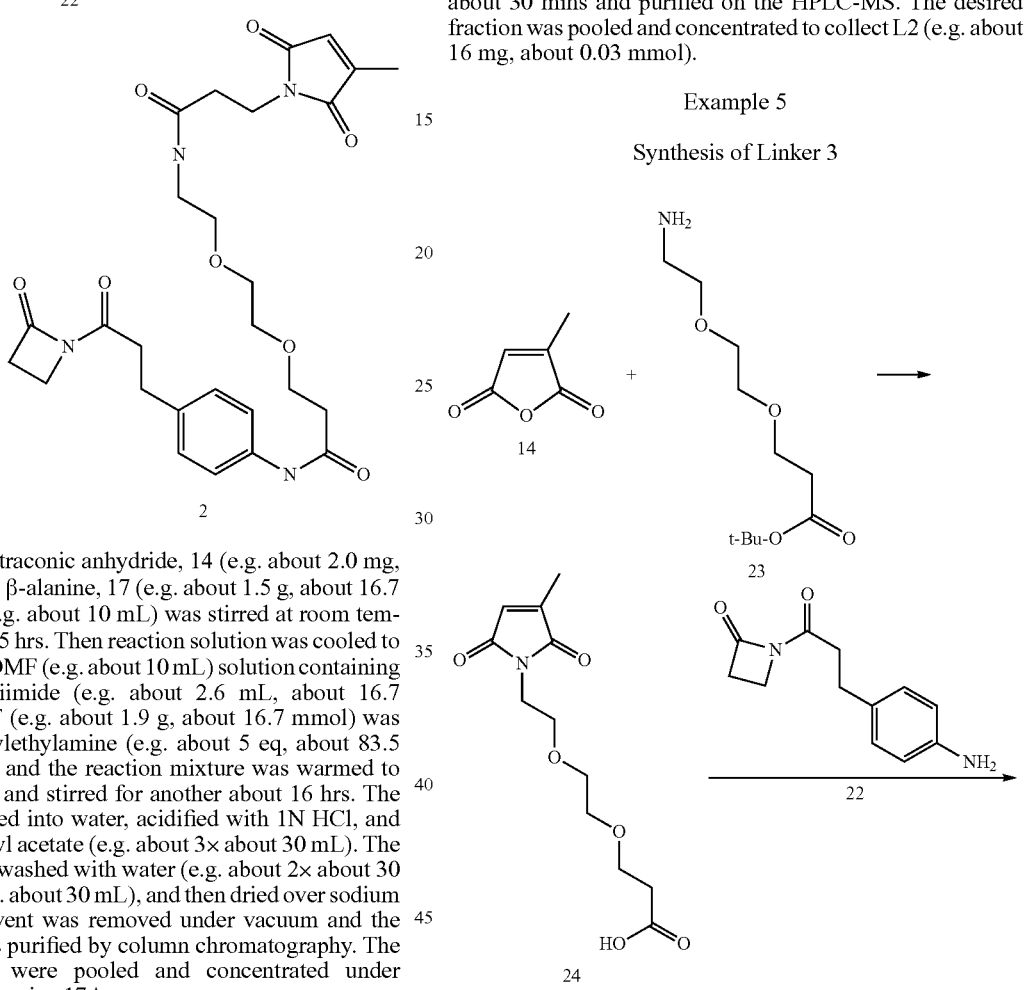

A solution of citraconic anhydride, 14 (e.g. about 2.0 mg, about 16.7 mmol), β-alanine, 17 (e.g. about 1.5 g, about 16.7 mmol) in DMF (e.g. about 10 mL) was stirred at room temperature for about 5 hrs. Then reaction solution was cooled to about 0° C. and a DMF (e.g. about 10 mL) solution containing diisopropylcarbodiimide (e.g. about 2.6 mL, about 16.7 mmol) and HOBT (e.g. about 1.9 g, about 16.7 mmol) was added. Diisopropylethylamine (e.g. about 5 eq, about 83.5 mmol) was added and the reaction mixture was warmed to room temperature and stirred for another about 16 hrs. The reaction was poured into water, acidified with 1N HCl, and extracted with ethyl acetate (e.g. about 3× about 30 mL). The organic layer was washed with water (e.g. about 2× about 30 mL) and brine (e.g. about 30 mL), and then dried over sodium sulphate. The solvent was removed under vacuum and the crude mixture was purified by column chromatography. The desired fractions were pooled and concentrated under reduced pressure to give 17A.

Compound 17A (e.g. about 0.5 g, about 2.09 mmol) was stirred in about 15% trifluoroacetic acid in dichloromethane at room temperature for about 2 hrs and concentrated to dryness under reduced pressure. The free acid 18 was added to N-hydroxysuccinimide (e.g. about 0.25 g, about 2.09 mmol) in tetrahydrofuran (e.g. about 20 mL), followed by diisopropylcarbodiimide (e.g. about 0.33 ml, about 2.09 mmol) and was stirred for about 4 hrs at room temperature. Diisopropyl urea was filtered off. The filtrate was evaporated to dryness. Petroleum ether (e.g. about 30 mL) was added to the residue, triturated, shaken and the petroleum ether layer was decanted. This procedure was repeated one more time with petroleum ether and the product 18 dried under vacuum.

Amine-peg2-tbutyl ester, 19 (e.g. about 0.5 g, 2.09 mmol) was added to a THF solution of the activated 18 followed by excess DIPEA (e.g. about 3 equivalents). The solution was stirred at room temperature for a minimum of 1 hr and purified by HPLC-MS collecting Mass of 343 and 399. The fractions containing the desired product were pooled and lyophilized to collect 20. The residue was dissolved in about 15% trifluoroacetic acid in dichloromethane and few drops of water and stirred at room temperature for about 2 hrs. The reaction was concentrated to approximately 1 ml and treated with water precipitate the product. The crude material was purified using HPLC-MS to yield 21 (M+343).

A solution of acid 21 (e.g. about 60 mg, about 0.18 mmol), HBTU (e.g. about 137 mg, about 0.36 mmol), and aniline hydrochloride 22 (e.g. about 45 mg, about 0.18 mmol), diisopropylethylamine (e.g. about 0.14 ml, about 0.90 mmol) in DMF (e.g. about 2 mL) was stirred at room temperature for about 30 mins and purified on the HPLC-MS. The desired fraction was pooled and concentrated to collect L2 (e.g. about 16 mg, about 0.03 mmol).

Example 5

Synthesis of Linker 3

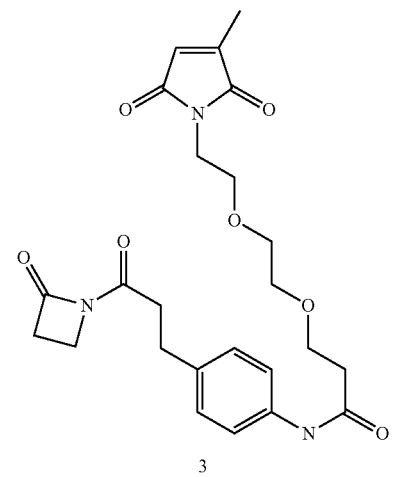

A solution of citraconic anhydride, 14 (e.g. about 0.5 g, about 16.4 mmol), amine-peg2-tbutyl ester 23 (e.g. about 1.0 g, about 4.2 mmol) in DMF (e.g. about 10 mL) was stirred at room temperature for about 2 hrs. Diisopropylcarbodiimide (e.g. about 0.8 mL, about 5.2 mmol) and HOBT (e.g. about 0.7 g, about 6.1 mmol) were added and the reaction was heated at about 80° C. for about 2 hrs. The reaction was allowed to cool to room temperature overnight and the urea filtered. The filtrate was poured into water and extracted with DCM. The organic layer was washed with brine and concentrated to oil. The crude product was dissolved in about 50% 6N HCl in acetonitrile to deprotect the acid. The product was dissolved in DMF, filtered, and purified using HPLC-MS to collect 24 (e.g. about 208 mg, about 0.7 mmol).

A solution of maleimide, 24 (e.g. about 0.16 g, about 0.6 mmol) and aniline hydrochloride 22 (e.g. about 150 mg, about 0.6 mmol) in DMF was added excess HBTU and DIEA (e.g. about over 3 equivalents of each). The crude material was purified via about 2 injections on an HPLC-MS. The desired fractions containing the purest material were pooled and lyophilized to collect L3 (e.g. about 17.3 mg, about 36.7 mmol).

Example 6

Synthesis of Linker 4

A solution of citraconic anhydride (14, e.g. about 510 mg, about 4.55 mmol) and trans-4-aminomethyl cyclohexane carboxylic acid (13, e.g. about 716 mg, about 4.55 mmol) in dimethylformamide (e.g. about DMF, about 5 mL) under nitrogen ($N_2$) was stirred at room temperature for about 6 hrs. The reaction solution was cooled to about 0° C., DIPEA (e.g. about 1.98 mL, about 11.4 mmol) followed by pentafluorophenyl trifluoroacetate (e.g. about 1.96 mL, about 11.4 mmol) in DMF (e.g. about 3 mL) were added. The reaction mixture was warmed to room temperature and stirred for another about 16 hrs under $N_2$. The solid was filtered, and the filtrate was poured into about 30 mL of water, extracted with dichloromethane (e.g. about 2× about 30 mL) and the dichloromethane layer was dried over $Na_2SO_4$. The solvent was removed under vacuum and the crude mixture was purified by column chromatography to yield about 550 mg of the pentafluorophenyl ester intermediate (15, e.g. about 29% yield).

N-Methyl morpholine (e.g. about 290 µL, about 2.64 mmol) was added to the solution of the pentafluorophenyl ester intermediate (15, e.g. about 550 mg, about 1.32 mmol) and 3-[2-(2-amino-ethoxy)-ethoxy]-propionic acid tert-butyl ester (e.g. about 295 mg, about 1.32 mmol) in terahydrofuran (THF, e.g. about 5 mL) and stirred at room temperature for about 2 hrs. The solvent was removed under vacuum and the residue was dissolved in DMF and purified by preparative HPLC. The tert-butyl ester intermediate obtained was treated

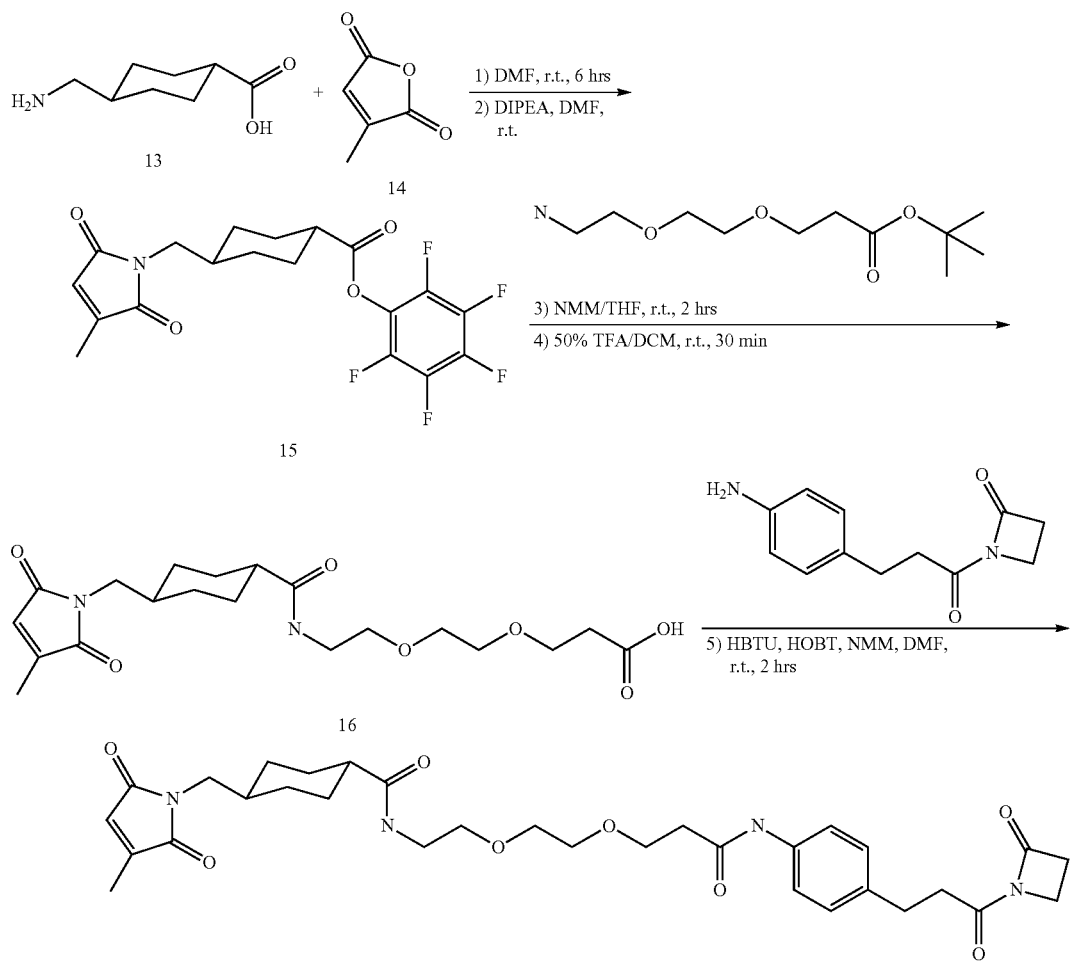

with about 50% trifluoroacetic acid in dichloromethane (e.g. about 4 mL) for about 30 mins. The solvent was removed under vacuum and the residue was purified by preparative HPLC to afford about 300 mg of the acid intermediate 16 as white solid (e.g. about 55% yield; MS: 411.2 (M+H$^+$)).

A solution of the above acid intermediate (16, e.g. about 33 mg, about 0.08 mmol), 1-[3-(4-amino-phenyl)-propionyl]-azetidin-2-one (e.g. about 18 mg, about 0.08 mmol), HOBT (e.g. about 25 mg, about 0.16 mmol) and HBTU (e.g. about 61 mg, about 0.16 mmol), and N-methyl morpholine (e.g. about 44 μL, about 0.4 mmol) in DMF (e.g. about 1 mL) was stirred at room temperature for about 2 hrs. The crude mixture was purified by preparative HPLC to afford L4 as colourless oil (e.g. about 22 mg, 45% yield; MS: 611.4 (MH$^+$)).

Example 7

Synthesis of Linker 5

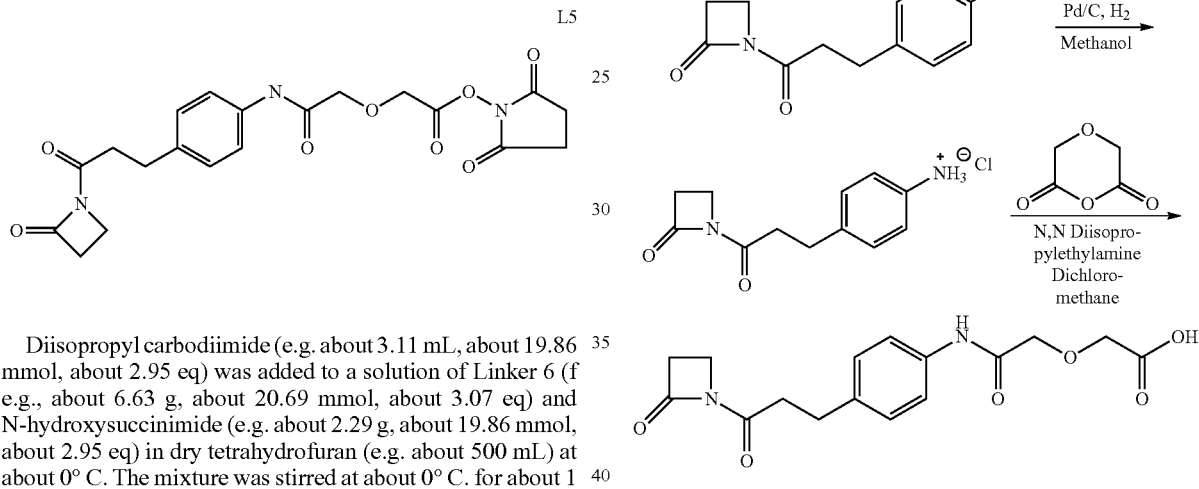

Diisopropyl carbodiimide (e.g. about 3.11 mL, about 19.86 mmol, about 2.95 eq) was added to a solution of Linker 6 (f e.g., about 6.63 g, about 20.69 mmol, about 3.07 eq) and N-hydroxysuccinimide (e.g. about 2.29 g, about 19.86 mmol, about 2.95 eq) in dry tetrahydrofuran (e.g. about 500 mL) at about 0° C. The mixture was stirred at about 0° C. for about 1 hr and then stirred at room temperature overnight. The solvent was removed in vacuo and the residue was washed with petroleum ether (e.g. about 2× about 200 mL) and the powder was dried under vacuo for about 2 hrs, and used in the subsequent steps.

Example 8

Synthesis of Linker 6

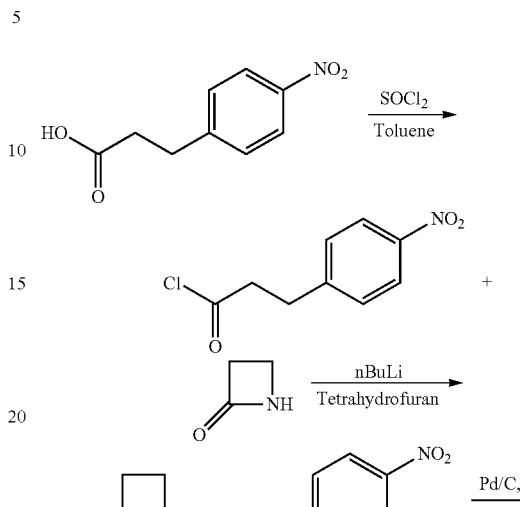

Example 9

Synthesis of Linker 7

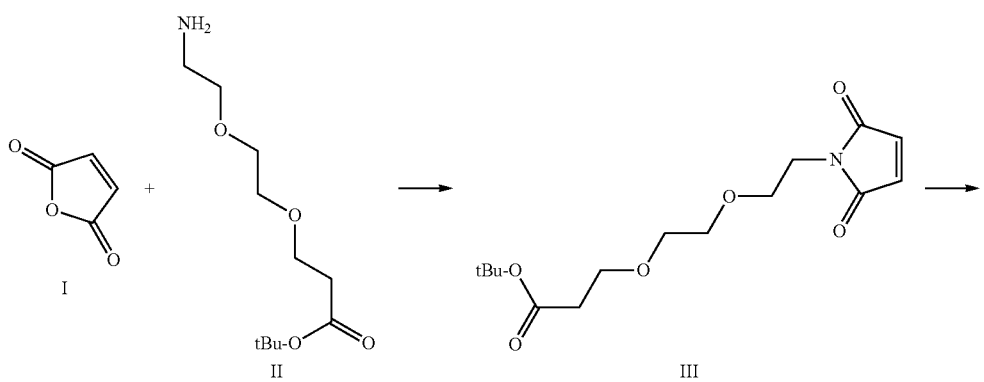

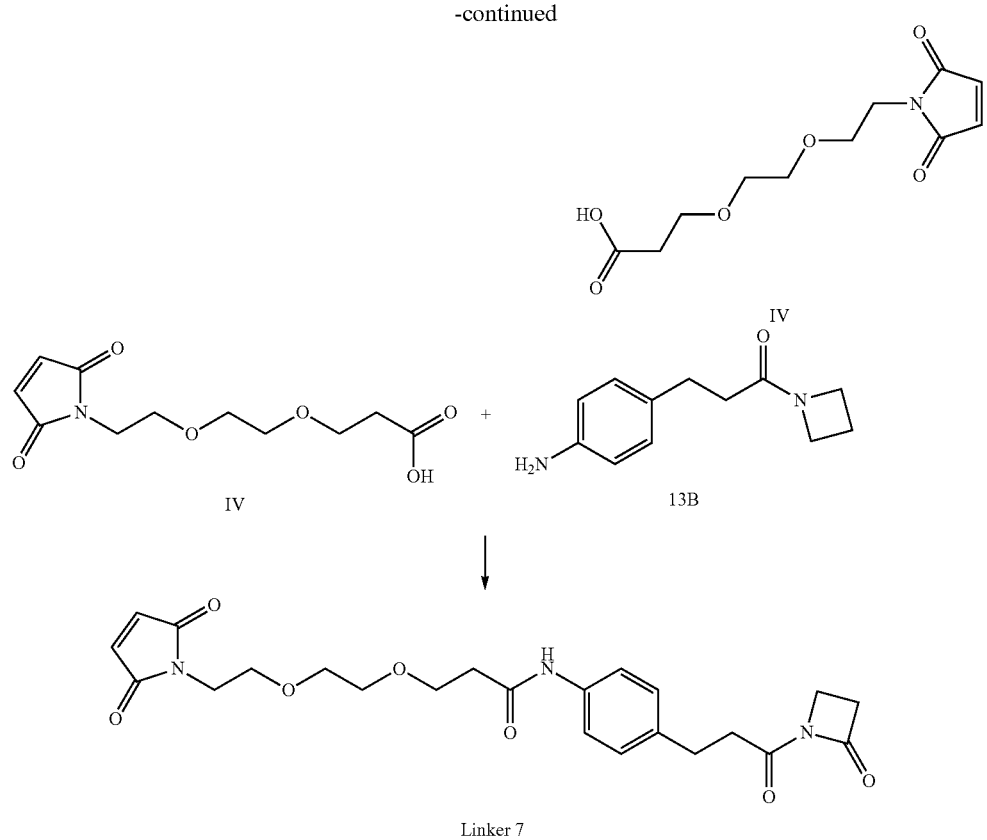

Linker 7

A solution of I (e.g. about 438 mg, about 4.47 mmol) and II (e.g. about 1.04 g, about 4.47 mmol) in dimethyl formamide (e.g. about 25 mL) was stirred under an atmosphere of nitrogen for about 2.5 hrs. The reaction was cooled to about 0° C. using an ice bath. 1-Hydroxypyrrolidine-2,5-dione (e.g. about 647 mg, about 5.62 mmol), and N-(3-dimethylaminopropyl)-N'-ethylcarbodiimide hydrochloride (e.g. about 1.71 g, about 8.92 mmol) were added and stirred at about room temperature overnight. The organic layer was diluted with dichloromethane, washed with water, concentrated under reduced pressure and purified using flash chromatography (SiO2, about 75% ethyl acetate in hexanes to about 5% methanol in dichloromethane to afford III (e.g. about 767 mg). A solution of III (e.g. about 573 mg, about 1.83 mmol) in dichloromethane (e.g. about 15 mL) and trifluoroacetic acid (e.g. about 1.16 mL) was stirred for about 9.5 hrs at about room temperature. The material was concentrated under reduced pressure and dried on a vacuum pump overnight to afford IV. The crude IV was dissolved in dichloromethane (e.g. about 15 mL), and dimethyl formamide (about 2 drops) and stirred with oxalyl chloride (e.g. about 465 mg, about 3.66 mmol) for about 2 hrs. The solvent was removed under reduced pressure and the oil was dried under vacuum for 1 hr. The oil was dissolved in dichloromethane (e.g. about 15 mL) and stirred with 13B (e.g. about 464 mg, about 1.83 mmol) and diisopropyl ethylamine (e.g. about 2.9 mL, about 16.5 mmol) under nitrogen for about 30 mins. The organic layer was washed with saturated sodium bicarbonate solution, saturated sodium chloride solution, concentrated under reduced pressure and purified using flash chromatography (SiO$_2$, about 85% ethyl acetate in hexanes to about 100% ethyl acetate) to afford Linker 7 (e.g. about 323 mg, about 39%).

Example 10

Synthesis of Linker 8

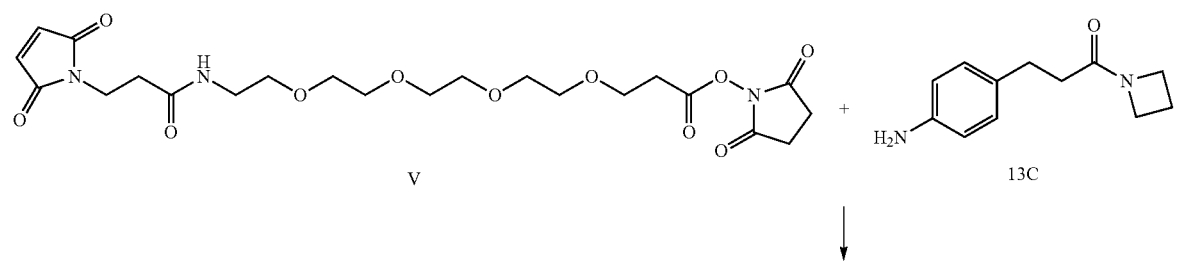

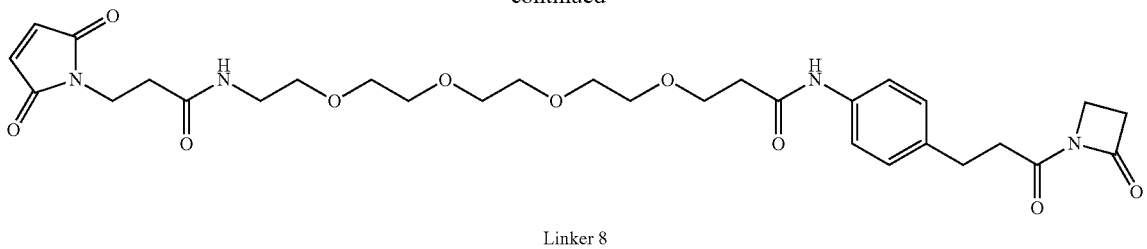

Linker 8

A solution of V (e.g. about 980 mg, about 1.91 mmol), 13C (e.g. about 484 mg, about 1.91 mmol), diisopropylethylamine (e.g. about 2 mL, about 11.5 mmol) in dichloromethane was stirred for about 6 hrs at about room temperature. Another about 1 eq of 13C (e.g. about 484 mg, about 1.91 mmol) and about 3 eq of diisopropylethylamine (e.g. about 1 mL, about 5.73 mmol) were added and stirred at about room temperature overnight. The reaction mixture was washed with saturated sodium bicarbonate solution, saturated sodium chloride solution, dried (sodium sulphate), filtered, concentrated under reduced pressure and purified using flash chromatography (about 100% ethyl acetate to about 5% methanol in ethyl acetate to about 10% methanol in ethyl acetate) to afford Linker 8 (e.g. about 285 mg, about 24%)

Example 11

Conjugation of Protein and Linker

FGF21 mutant proteins were reacted with the relevant linker at 1:10 molar ratio at room temperature for 2 hrs. All linker-attached FGF21 proteins were then purified using PD-10 column and buffer exchanged into 20 mM Tris-HCl, 20 mM NaCl, pH 7.0.

Example 12

Conjugating Protein-Linker Complex with Antibody

All linker-attached FGF21 proteins were fused with h38C2 IgG1 (SEQ ID NOS: 25 and 26) (20 mM Tris-HCl, 20 mM NaCl, pH 7.0) at 6:1 molar ratio at room temperature for overnight. Protein-linker-antibody complexes were purified by SEC. Conjugation efficiency was confirmed by LCMS analysis.

Example 13

Protein Production Assay

All FGF21 proteins were expressed in *E. coli*. Bacterially expressed FGF21 proteins were found in inclusion bodies. After lysing the cells and removal of the supernatant, the pellets were dissolved in 7 M urea, 50 mM Bis-Tris propane, pH 10.5 at 4° C. The solubilized inclusion bodies were diluted into 50 mM Bis-Tris propane, 10 mM oxidized glutathione, ph 9.0 and stirred for 2 hrs, followed by dialysis against 20 mM Tris-HCl, ph 7.5 at 4° C. overnight. The soluble fractions were purified by HiTrap Q column. Proteins were characterized by SDS-PAGE analysis. Expression levels of the lysine mutants were 10-50 mg/L.

Example 14

Glut1 Taqman Assay

Differentiated 3T3-L1 adipocytes were used to measure the Glut1 mRNA expression by qPCR method. Overnight serum starved day 10-14 differentiated 3T3-L1 adipocytes were treated with compounds for 6 hrs. Total RNA was extracted from these cells, and Glut1 and GAPDH mRNA expression was measured using a Quantitect Probe RT-PCR kit and running a quantitative real time PCR reaction in a Taqman machine (Applied Biosystems®). The bioactivity of the compounds was determined by a fold change in Glut1 mRNA levels normalized by the GAPDH mRNA levels from each sample. $EC_{50}$ values as measurements of the potency of the compounds were obtained from the dose response curves in the assay.

Example 15

Glucose Uptake Assay

Differentiated 3T3-L1 adipocytes were treated with compounds in the absence of serum for 24 hrs. Cells were then incubated with $^{14}C$-2-deoxyglucose for 1 hr and glucose uptake into the cells was quantitated in Wallac 1450 Micro-Beta (Trilux) instrument. Glucose uptake was expressed in counts per min (CPM). $EC_{50}$ values as measurements of the potency of the compounds were obtained from the dose response curves in the assay.

Example 16

Mouse Pharmacokinetics

The PK of FGF21 antibody conjugates were examined in mice after IV or SC administration. Antibody conjugates were injected into young adult male Swiss-Webster mice (20-25 g), and blood samples were obtained at time points from 5 mins to 120 hrs after dosing. Antibody conjugates concentrations in serum were determined using an ELISA which captured the FGF21 portion of the antibody conjugates through a monoclonal anti-hFGF21 antibody bound to a 96-well plate. FGF21 antibody conjugates bound to the plate were detected through an anti-hFc monoclonal antibody, and concentrations were determined using a standard curve of the PK dosing solution diluted into serum-containing assay buffer. SC bioavailability was calculated as the ratio of the area-under the curve (AUC) of the SC serum concentration profile divided by the AUC of the IV serum concentration profile.

Example 17

Mouse Efficacy

The efficacy of FGF21 antibodies conjugates was evaluated in two murine obese insulin resistant models—ob/ob mice and high-fat diet-induced obese mice. For both models, male mice (6-8 weeks of age for ob/ob, 12-14 weeks of age for DIO with high-fat diet initiated at 6 weeks of age) were housed 2-4/cage and FGF21 antibody conjugates were administered by SC injection. Body weight was measured daily in the morning. Glucose tolerance was assessed by oral glucose tolerance test. Briefly, mice were fasted for 4-5 hrs in the morning of the day of testing. A basal blood sample was obtained and blood glucose levels were determined using a portable glucometer. Following basal sample, glucose was administered by oral gavage, and blood samples were drawn from 15 to 120 mins thereafter. Glucose tolerance was calculated as the AUC from the basal to the 120 min time point.

Example 18

K56 Ab-L5-FGF21ΔH-K56 Activity

FGF21ΔH-K56-K59R-K69R-K122R (SEQ ID NO:18) was generated and purified as described above. FGF21ΔH-K56-K59R-K69R-K122R was found to be potent in the Glut1 Taqman assay ($EC_{50}$=0.9 nM; n=2). Glucose uptake was shown to be 5.5 nM. FGF21ΔH-K56-K59R-K69R-K122R was combined with L5 at K56 and conjugated with h38C2 as described to form Ab-L5-FGF21ΔH-K56. Ab-L5-FGF21ΔH-K56 retained potency in Glut1 Taqman assay ($EC_{50}$=1.9 nM; n=1), and showed an IV half-life of 17 hrs, and a SC half-life of 13 hrs. Bioavailability was 66%.

Example 19

K59 Ab-L5-FGF21ΔH-K59 Activity

FGF21ΔH-K56R-K59-K69R-K122R (SEQ ID NO:19) was generated and purified as described. FGF21ΔH-K56R-K59-K69R-K122R was potent in the Glut1 Taqman assay ($EC_{50}$=0.6 nM; n=1). Glucose uptake was 0.9 nM. FGF21ΔH-K56R-K59-K69R-K122R was combined with L5 at K59 and conjugated with h38C2 to form Ab-L5-FGF21ΔH-K59. Ab-L5-FGF21ΔH-K59 retained in vitro potency in the Glut1 Taqman assay ($EC_{50}$=6.5 nM; n=2) and showed an IV half-life of 13 hrs.

Example 20

K69 Ab-L5-FGF21ΔH-K69 Activity

FGF21ΔH-K56R-K59R-K69-K122R (SEQ ID NO:20) was generated and purified as described. FGF21ΔH-K56R-K59R-K69-K122R was found to be potent in both a Glut 1 Taqman assay ($EC_{50}$=1.3 nM; n=1) and a glucose uptake assay ($EC_{50}$=5.2 nM). FGF21ΔH-K56R-K59R-K69-K122R was combined with L5 at K69, and conjugated with h38C2 to form Ab-L5-FGF21ΔH-K69.

Example 21

K122 Ab-L5-FGF21ΔH-K122 Activity

FGF21ΔH-K56-K59R-K69R-K122 (SEQ ID NO:21) was generated and purified as described. FGF21ΔH-K56R-K59R-K69R-K122 was potent in both Glut 1 Taqman assay ($EC_{50}$=2.6 nM; n=2) and glucose uptake assay ($EC_{50}$=1.7 nM). FGF21ΔH-K56-K59R-K69R-K122 was combined with L5 at K122, and conjugated with h38C2 to form Ab-L5-FGF21ΔH-K122. Ab-L5-FGF21ΔH-K122 retained in vitro potency ($EC_{50}$=1.6 nM in Glut1 Taqman assay; n=2) and showed an IV half-life of 16 hrs, and a SC half-life of 14 hrs. Bioavailability was 40%.

Example 22

K-null-P2 Ab-L5-FGF21ΔH-Knull-P2 Activity

FGF21ΔH-Knull-P2 (SEQ ID NO:22) was generated and purified as described. FGF21ΔH-Knull-P2 was potent in Glut 1 Taqman assay ($EC_{50}$=1.2 nM; n=2). FGF21ΔH-Knull-P2 was combined at the N' terminus of $P^2$ with L5, and conjugated with h38C2 to form Ab-L5-FGF21ΔH-Knull-P2. Ab-L5-FGF21ΔH-Knull-P2 displayed reduced in vitro potency ($EC_{50}$=16.6 nM in Glut1 Taqman assay; n=1) and an IV half-life of 17 hrs.

Example 23

Knull-H1K Ab-L5-FGF21ΔH-Knull-H1K Activity

FGF21ΔH-Knull-H1K (SEQ ID NO:23) was generated and purified as described. FGF21ΔH-Knull-H1K was potent in Glut 1 Taqman assay ($EC_{50}$=6.4 nM; n=2). FGF21ΔH-Knull-H1K was combined with L5 at H1K and conjugated with h38C2 to form Ab-L5-FGF21AK-Knull-H1K. FGF21ΔH-Knull-H1K retained in vitro potency ($EC_{50}$=4.3 nM in Glut1 Taqman assay; n=2), and showed an IV half-life of 16 hrs, a SC half-life of 11 hrs and SC bioavailability of 51%.

Example 24

K-null-S181K Ab-L5-FGF21ΔH-Knull-S181K activity

FGF21ΔH-Knull-S181K (SEQ ID NO:24) was generated and purified as described. FGF21ΔH-Knull-S181K was potent in Glut 1 Taqman assay ($EC_{50}$=7.5 nM; n=2). FGF21ΔH-Knull-S181K was combined with L5 at 5181K and conjugated with h38C2 to form Ab-L5-FGF21ΔH-Knull-S181K. Ab-L5-FGF21ΔH-Knull-S181K showed a loss of in vitro potency ($EC_{50}$=>500 nM in Glut1 Taqman assay; n=2).

Example 25

Summary of Results of Activity of Lysine Mutants

All lysine mutant proteins were active in Glut1 Taqman assay. When conjugated, the majority of the conjugates (K56, K59, K122, Knull-H1K) retained activity in Taqman assay, with $EC_{K_5}$ values similar to that of the native FGF21 protein. The Knull-P2 conjugate showed some reduction in initial potency, and Knull-S181K conjugate showed loss of activity in the Taqman assay.

Example 26

Identifying Optimal Tether Sites on FGF21 Using Cysteine-Maleimide Conjugation One of the challenges when introducing a cysteine substitution mutation as a linking residue is that the cysteine residue may find itself in contact with other residues, and/or form a salt bridge or hydrogen bond. Although it can be difficult to predict the atom-level distances using modelled structures, a number of residues were selected based on potential for being distally located from the FGFR1c and βKlotho binding sites: His1, Thr40, Asp79, Leu86, His125 and Ala129. All six residues are distinct to each other in terms of structural elements (turn and loop), accessible surface area (ASA), and shape of environment (convex and concave), and all were modelled on the opposite side of the protein to the FGFR1c interactions (Table 2). In particular, His1, Asp79, Leu86 and His125 were identified as being potentially attractive conjugation sites due to the high ASA values associated with these sites.

TABLE 2

Comparison of candidate residues for cysteine substitution

| Residues | Structure | Shape | % ASA | ASA | βKlotho site |
|---|---|---|---|---|---|
| His1 | disorder | N/A | N/A | | |
| Thr40 | β-strand | concave | 34 | 49.8 | less far |
| Asp79 | β-turn | convex | 71 | 109.8 | far |
| Leu86 | β-strand | convex | 60 | 119.4 | less far |
| His125 | disorder | convex | 85 | 169.4 | far |
| Ala129 | disorder | concave | 68 | 78.8 | far |

Example 27

H1C FGF21ΔH-H1C

FGF21ΔH-H1C (SEQ ID NO:16) was generated and expressed. However, FGF21ΔH-H1C mutants lacked the N' cysteine group, and therefore investigation of this mutant was discontinued.

Example 28

T40C FGF21ΔH-T40C

Generation of FGF21ΔH-T40O (SEQ ID NO:15) presented significant challenges. The cysteine mutation of threonine at position 40 caused multiple species of FGF21ΔH-T40O in RP-HPLC after refolding. Further attempts were made to improve the refolding process by changing the concentration of protein and pH, with and without addition of glutathione. The refolding process was monitored by RP-HPLC. Addition of glutathione resulted in efficient refolding of T40O; however, it was found that glutathione was attached on FGF21, most likely through the introduced cysteine at position 40. The glutathione adduct showed the same biological activity as wild type FGF21EH, indicating that the position 40 is not involved in the receptor activation by FGF21.

Example 29

D79C Ab-L1-FGF21ΔH-D79C Activity

FGF21ΔH-D79C (SEQ ID NO: 13) was generated and purified as described. FGF21ΔH-D79C was potent in Glut 1 Taqman assay ($EC_{50}$=2.1 nM; n=4). FGF21ΔH-D79C was combined with L1 at D79C and conjugated with h38C2 to form Ab-L1-FGF21ΔH-D79C. Ab-L1-FGF21ΔH-D79C retained in vitro potency ($EC_{50}$=3.7 nM in Glut1 Taqman assay; n=3), and showed an IV half-life of 17 and 19 hrs (n=2), a SC half-life of 20 and 20 hrs (n=2) and SC bioavailability of 55% and 70 (n=2).

Example 30

Stability Assay of FGF21ΔH-D79C

FGF21ΔH-D79C mutant protein was produced in E. coli and purified as described above. FGF21ΔH-D79C was expressed from 1 L of culture. A 150 mg inclusion body was obtained and 85 mg purified protein was obtained, representing a 60% yield. To test the stability of FGF21ΔH-D79C as well as FGF21ΔH (SEQ ID NO:2), freshly thawed samples were kept at 4° C. over seven days, and examined for their integrity by RP-HPLC, SEC_HPLC, Ellman assay and SDS-PAGE on day 0, 3 and 7. It was found that FGF21ΔH-D79C is stable at neutral pH 7.4: only slight amounts of FGF21ΔH-D79C appeared oxidized and dimerized even after seven-day incubation at 4° C., while more than half of FGF21ΔH-D79C was oxidized at lower pH 6.0 after three-day incubation at 4° C. PBS (pH7.4) and 20 mM Tris-HCl 50 mM NaCl (pH7.5) made no significant difference of stability of FGF21ΔH-D79C.

It is not apparent why the free cysteine of FGF21ΔH-D79C was more stable at pH 7.4 than at pH 6.0. The calculated isoelectric point (pI) of WT FGF21 was 5.43 (e.e., FGF21-H1-L146); the pI of FGF21ΔH 5 was 5.27; and the pI of FGF21ΔH-D79C was 5.47. It is possible that the solubility of FGF21ΔH-D79C may be reduced at pH6.0. The stability of FGF21ΔH-D79C was examined upon multiple freeze/thaw cycles. The proteins were repeated to freeze (−80 C) and thaw (4° C.) 9 times. Neither sample showed any difference between cycle 1 and cycles 9 in RP-HPLC, SEC and Ellman assay. In conclusion, FGF21ΔH-D79C appeared to be significantly less stable at 4° C. than at −80° C.

Example 31

L86C FGF21ΔH-L86C

FGF21ΔH-L86C (SEQ ID NO:14) was generated and purified as described. Although most hydrophobic residues are buried in protein cores, some residues are exposed to solvent which may cause insolubility of the protein. Leu86 is a hydrophobic residue, and appears solvent exposed in the modelled structure of FGF21. It was postulated that the mutation L86C may provide solubility benefits.

The L86C mutation resulted in inefficient refolding and low protein yield. Addition of glutathione resulted in efficient refolding of L86C; however, it was found that more than one glutathione was attached on one FGF21 molecule, most likely through the introduced C86 as well as native cysteine residues. The glutathione adduct showed approximately 10-fold reduction of biological activity, and therefore investigation of FGF21ΔH-L86C was discontinued.

Example 32

H125C Ab-L1-FGF21ΔH-H125C Activity

FGF21ΔH-H125C (SEQ ID NO: 6) was generated and purified as described. FGF21ΔH-H125C was potent in Glut 1 Taqman assay ($EC_{50}$=1.2 nM; n=3). FGF21ΔH-H125C was combined with L1 and conjugated with h38C2 at H125C to form Ab-L1-FGF21ΔH-H125C. When conjugated, Ab-L1-FGF21ΔH-H125C retained in vitro potency ($EC_{50}$=3.2 nM in Glut1 Taqman assay; n=4), and showed an IV half-life of 37 hrs, a SC half-life of 32 hrs and SC bioavailability of 67%.

Example 33

A129C Ab-L1-FGF21ΔH-A129C Activity

FGF21ΔH-A129C (SEQ ID NO: 9) was generated and purified as described. FGF21ΔH-A129C was potent in Glut 1 Taqman assay ($EC_{50}$=1.4 nM; n=6). FGF21ΔH-A129C was combined with L1 at A129C and conjugated with h38C2 to form Ab-L1-FGF21ΔH-A129C. Ab-L1-FGF21ΔH-A129C retained in vitro potency ($EC_{50}$=2.7 nM in Glut1 Taqman assay; n=7), and showed an IV half-life of 33 hrs, a SC half-life of 37 hrs and SC bioavailability of 69% (in mice). Ab-L1-FGF21ΔH-A129C showed an IV half-life in rat of 60 hrs, a SC half-life in rat of 39 hrs, and SC bioavailability in rat of 52%. In monkey, the IV half-life was 65 hrs, the SC half-life was 48 hrs, and the SC bioavailability was 68%.

Example 34

Improvement of Endotoxin Purity

FGF21ΔH-H1250 and FGF21ΔH-A129C protein were produced by *E. coli* fermentation culture. To reduce endotoxin levels, an additional Q step was utilized after the first Q which reduced the endotoxin levels from 10 EU/ml->0.1 EU/mL. The purification protocol was modified as follows. Approximately 10 g IB was obtained from 1 L culture media, and solubilized with 40 mL of 7M Urea, 5 mM DTT, 50 mM BTP (Bis-tris Propane) pH10.5 (1~2 hrs). Reduction of FGF21 protein was monitored by RP-HPLC. The solubilized protein was refolded by dilution into 400 mL of 50 mM BTP, pH 8.0 (24~36 hrs). Oxidation of native disulphide bond of FGF21 was monitored by RP-HPLC. Once refolding was almost completed, the solution was dialyzed twice against 4 L of 20 mM Tris-HCl, pH 7.5. Unsolubilized proteins were precipitated out by centrifugation at 20,000×g for 60 min, 4° C. The supernatant was loaded onto a Hitrap Q FF and the FGF21 protein was eluted with 0~200 mM NaCl gradient (20 CV, 20 mM Tris-HCl, 0.01 mM TCEP, pH 7.5). The collected fractions were loaded onto a Hitrap Ni-NTA FF with 0~100 mM imidazole gradient (10 CV, 0.01 mM TCEP, PBS, pH 7.4) to remove residual DNA efficiently. The desired fractions were dialyzed twice against 4 L of 20 mM Tris-HCl, 0.01 mM TCEP, pH 7.5 and loaded onto a Hitrap Q HP column with 0~100 mM NaCl gradient (20 CV, 20 mM Tris-HCl, pH 7.5) for elution. Purified protein fractions were collected, sterilized with a 0.22 mm filter and stored at −80°.

The typical yield from 1 L culture media was about 350 to about 400 mg. The typical yield of purified protein was about 220 to about 280 mg. This purification technique yielded protein with a purity of >95%, and a typical endotoxin level of about 1 EU/mg. Using a fermentor in place of shake flasks improved the yield about 4 to about 5 times.

Example 35

Linker Selection

It is known that the maleimide ring of L1, below, may be susceptible to opening and subsequent product degradation over time (Woodnutt, G; IBC Conference "Beyond Antibodies/Protein Engineering Design", San Diego, 21-23 Sep. 2009).

Maleimide linker such as L1 can react with thiol to form a thiol adduct with maleimide part as shown in Scheme 1. This addition reaction of thiol to maleimide is referred as to a Michael reaction. Subsequently, a group containing amine (such as antibody h38C2) can react with AZD (δ-lactam) as shown in Scheme 1 to yield 6. The resulting thiol-succinimide adduct is stable. However, the succinimide ring can undergo a slow hydrolytic cleavage over time resulting in 7 and/or 8. Therefore it is desirable to have a maleimide ring with improved stability towards hydrolytic cleavage, while preserving its ability to undergo Michael reaction.

Scheme 1

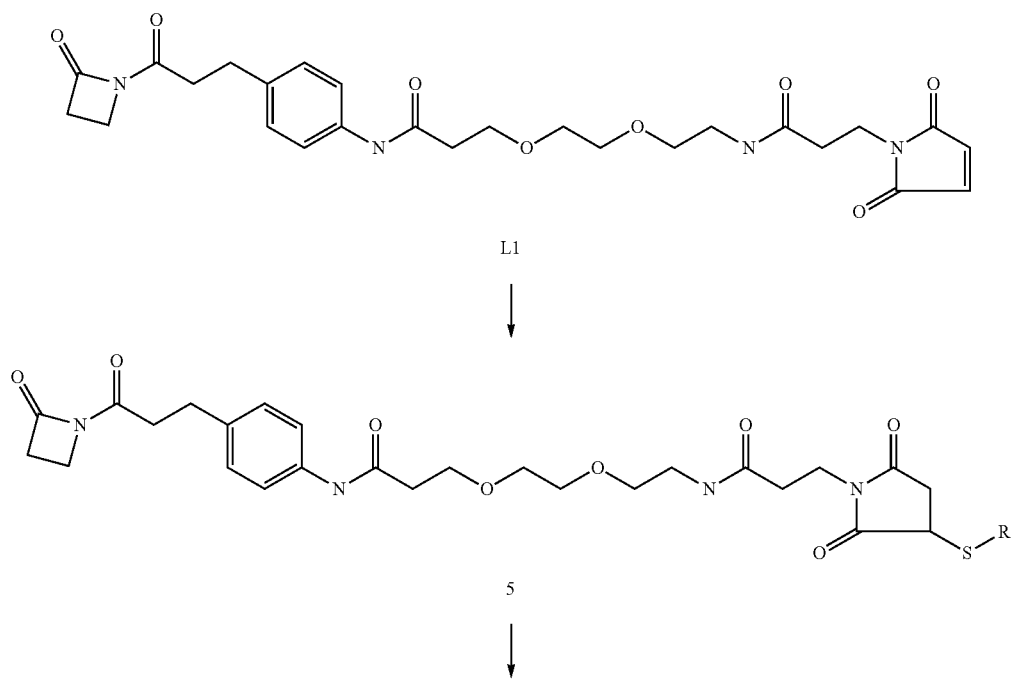

-continued

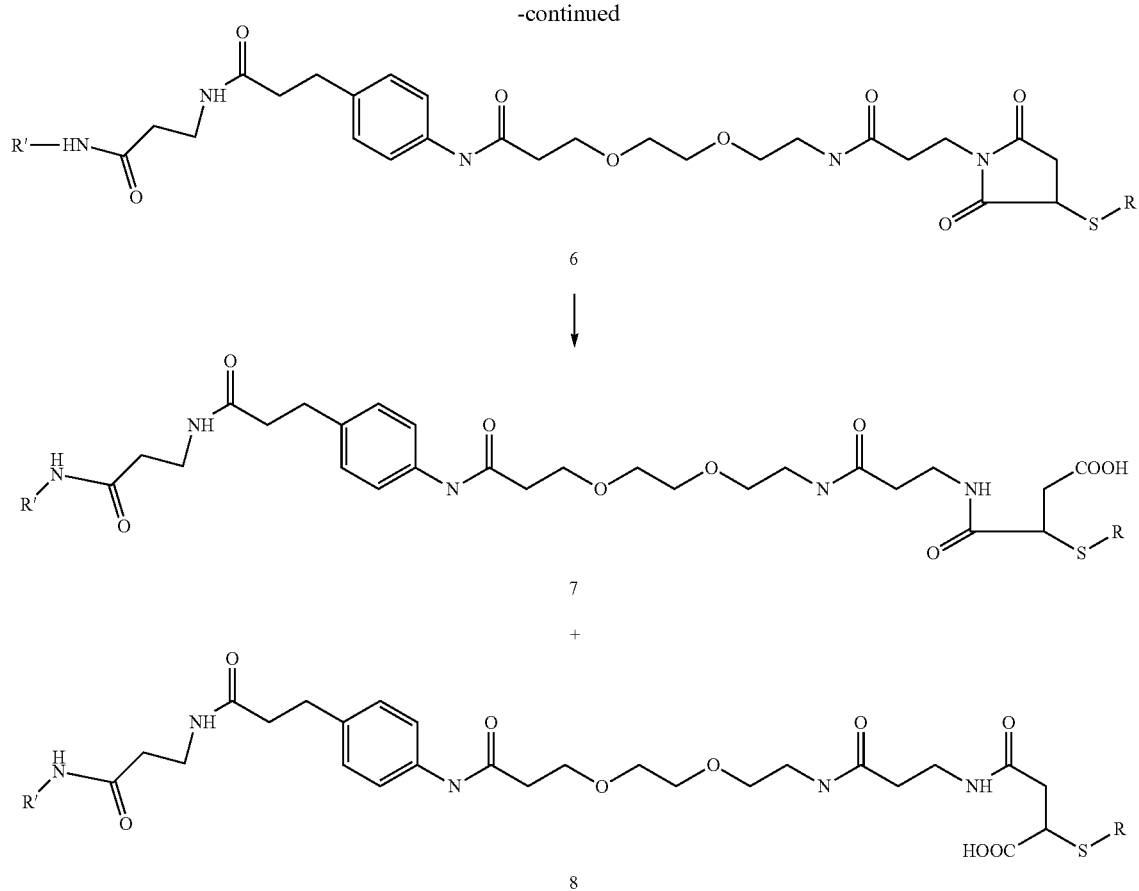

Example 36
Maleimide Modification

Accordingly, the stability of the maleimide ring in L1 was examined, with the expectation that more stable linkers could be generated by modifying the maleimide ring. In order to slow the potential hydrolytic cleavage of the maleimide ring by water, three different approaches (L2-L4) were taken to modify the ring and improve the stability.

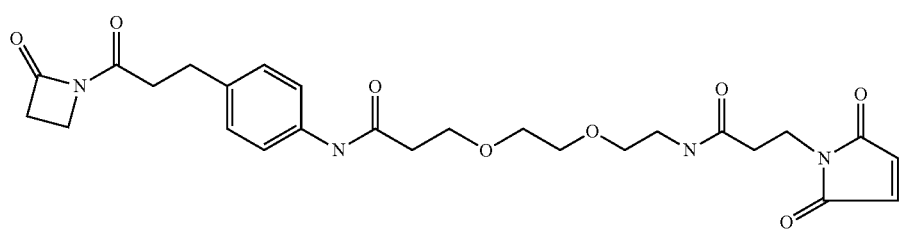

L1

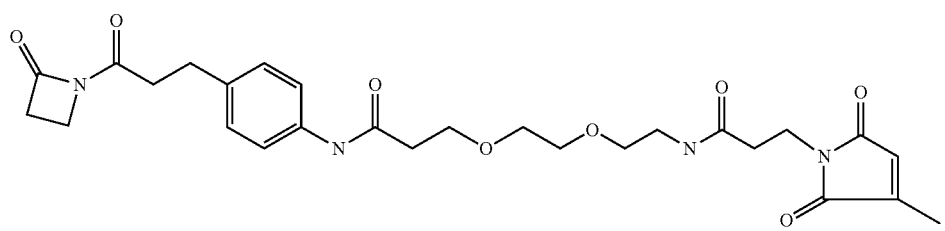

L2

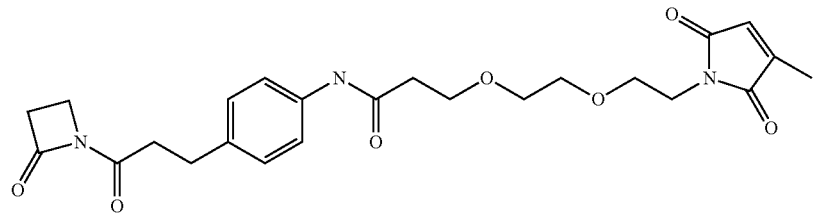

L3

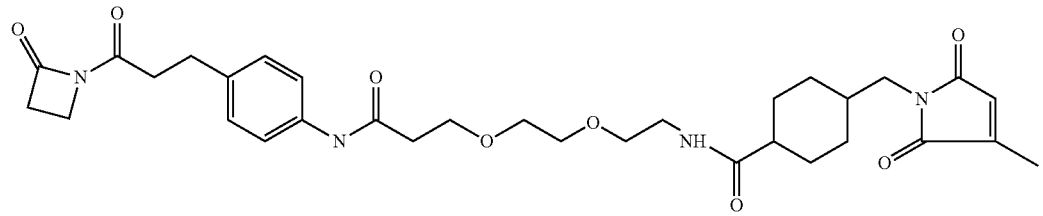

L4

First, it was envisioned that a small alkyl group attached to the ring might slow the hydrolytic cleavage of the succinimide ring. Linker 2, which has a methyl group on the succinimide ring, was prepared. In order for the ring to undergo hydrolytic cleavage, a water molecule adds to the carbonyl group and forms a tetrahedral intermediate as transition state. The presence of the methyl group would sterically and electronically limit the formation of the tetrahedral intermediate, and slow down the hydrolysis rate considerably.

The second modification was focused on the propionamide carbonyl group in close vicinity to the carbonyl group of the maleimide ring. Carbonyl groups in general attract water. Having a carbonyl group in close proximity to the maleimide ring helps attract water and facilitates the attack on the carbonyl group of the maleimide ring. By removing the propionamide carbonyl group, the hydrolytic ring opening reaction is slowed down. This modification was seen in L3.

The third modification was the introduction of a cyclohexylmethylene group in the place of propionamide group as seen in L4. The bulky hydrophobic nature of the cyclohexyl ring would interfere both electronically and sterically towards the formation of a tetrahedral intermediate by the addition of water to the carbonyl group of the ring which is required for the ring opened hydrolytic cleavage. It was anticipated that this would slow down the hydrolytic cleavage.

Stability Studies

For the stability studies, the 1-(3-(4-aminophenyl)propanoyl)azetidin-2-one portion from linkers L1-L4 was removed. Four test compounds were made (30-33) where the maleimide was conjugated with glutathione, a three amino acid peptide.

Example 37

Synthesis of compound 30

A solution of 3-(2-(2-(3-(2,5-dioxo-2,5-dihydro-1H-pyrrol-1-yl)propanamido)-ethoxy)ethoxy)propanoic acid (164 mg, 0.5 mmol) and reduced glutathione (154 mg, 0.5 mmol) in dimethylsulfoxide (5 mL) was stirred at room temperature for 17 hrs. Ethyl acetate (25 mL) was added to the reaction mixture and the solid was filtered. The solid was washed with additional 25 mL of ethyl acetate, dried to give 252 mg of compound 30.

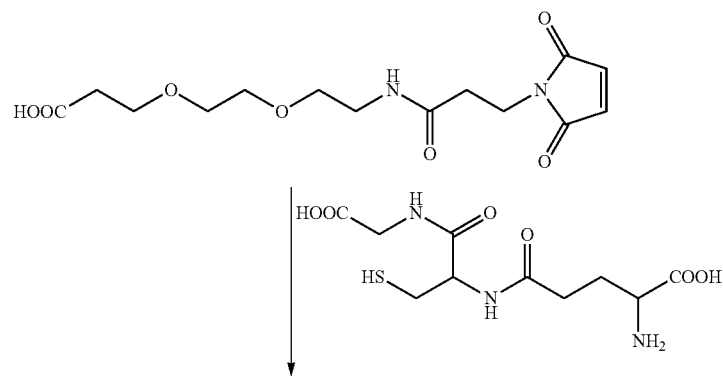

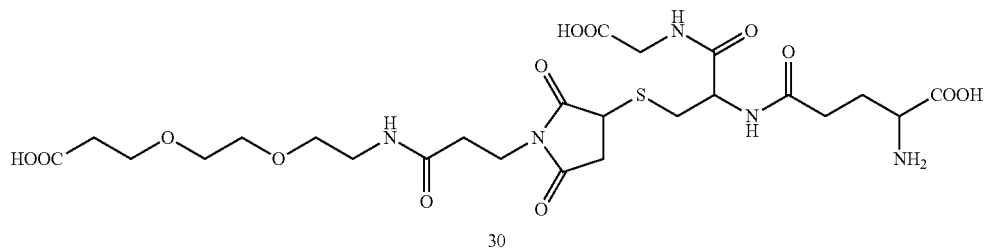

30

Example 38

Synthesis of compound 31

A solution of 3-(2-(2-(3-(3-methyl-2,5-dioxo-2,5-dihydro-1H-pyrrol-1-yl)propanamido)ethoxy)ethoxy)propanoic acid (42 mg, 0.12 mmol) and reduced glutathione (37 mg, 0.12 mmol) in dimethylsulfoxide (1.2 mL) was stirred at room temperature for 22 hrs. 50% Ethyl acetate in ether (10 mL) was added to the reaction mixture and the solid was filtered. The solid was washed with additional 25 mL of ethyl acetate, dried to give 67 mg of compound 31.

Example 39

Synthesis of Compound 32

A solution of 3-(2-(2-(3-methyl-2,5-dioxo-2,5-dihydro-1H-pyrrol-1-yl)ethoxy)ethoxy)propanoic acid (50 mg, 0.2 mmol) and reduced glutathione (61 mg, 0.2 mmol) in dimethylsulfoxide (2 mL) was stirred at room temperature for 25 hrs. 65% Ethyl acetate in ether (30 mL) was added to the reaction mixture and the solid was filtered. The solid was washed with additional 25 mL of ethyl acetate, dried to give 92 mg of compound 32.

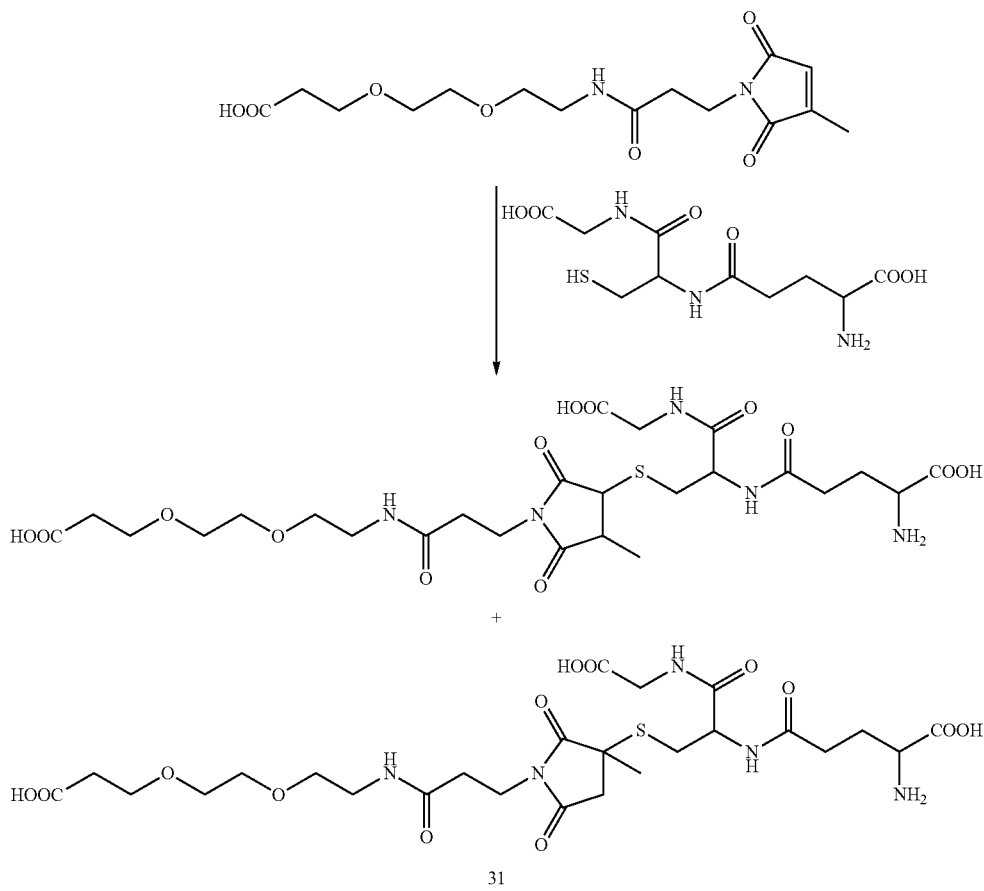

31

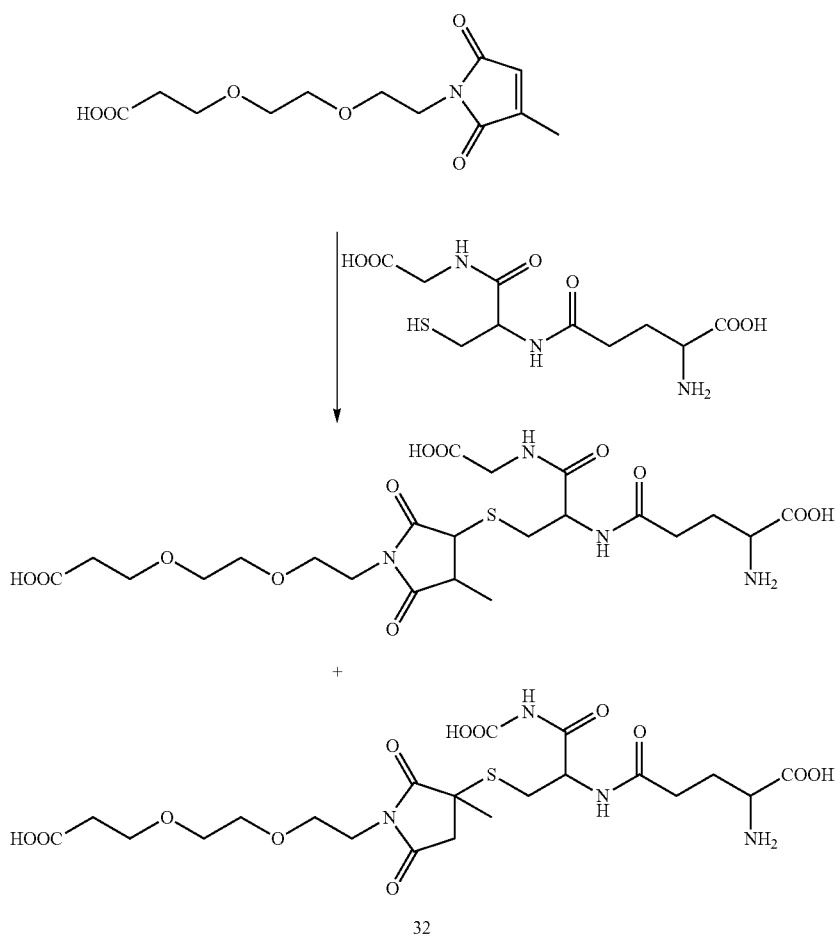

Example 40

Synthesis of Compound 33

A solution of 3-(2-(2-(4-((3-methyl-2,5-dioxo-2,5-dihydro-1H-pyrrol-1-yl)methyl)cyclohexanecarboxamido)ethoxy)ethoxy)propanoic acid (50 mg, 0.12 mmol) and reduced glutathione (37 mg, 0.12 mmol) in dimethylsulfoxide (1.2 mL) was stirred at room temperature for 22 hrs. 50% Ethyl acetate in ether (10 mL) was added to the reaction mixture and the solid was filtered. The solid was washed with additional 25 mL of ethyl acetate, dried to give 75 mg of compound 33.

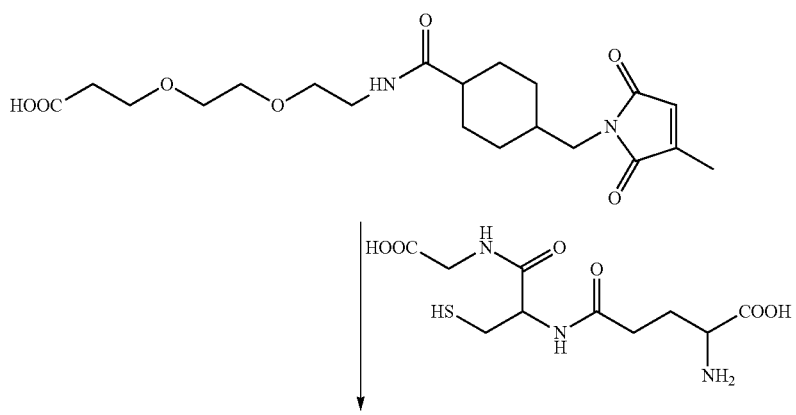

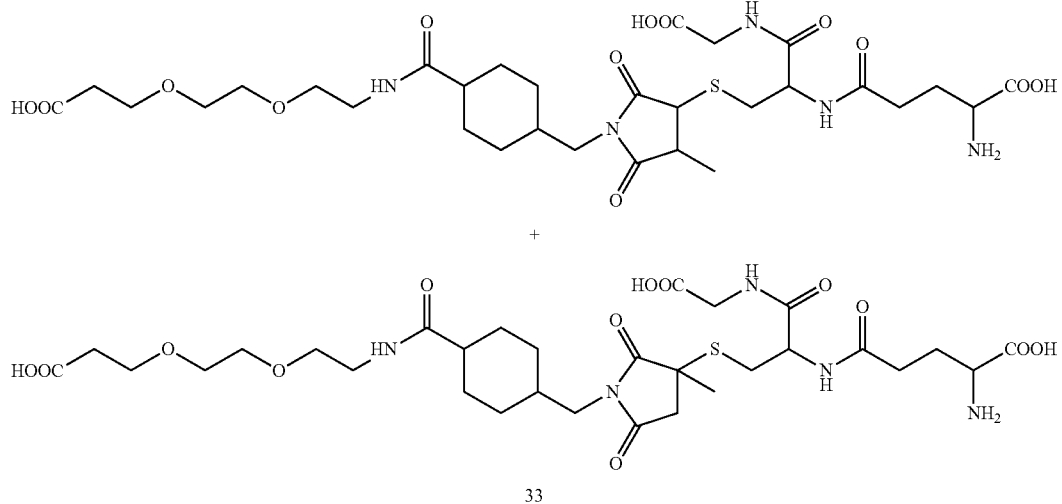
33
Example 41
Stability Study of Compounds 30-33
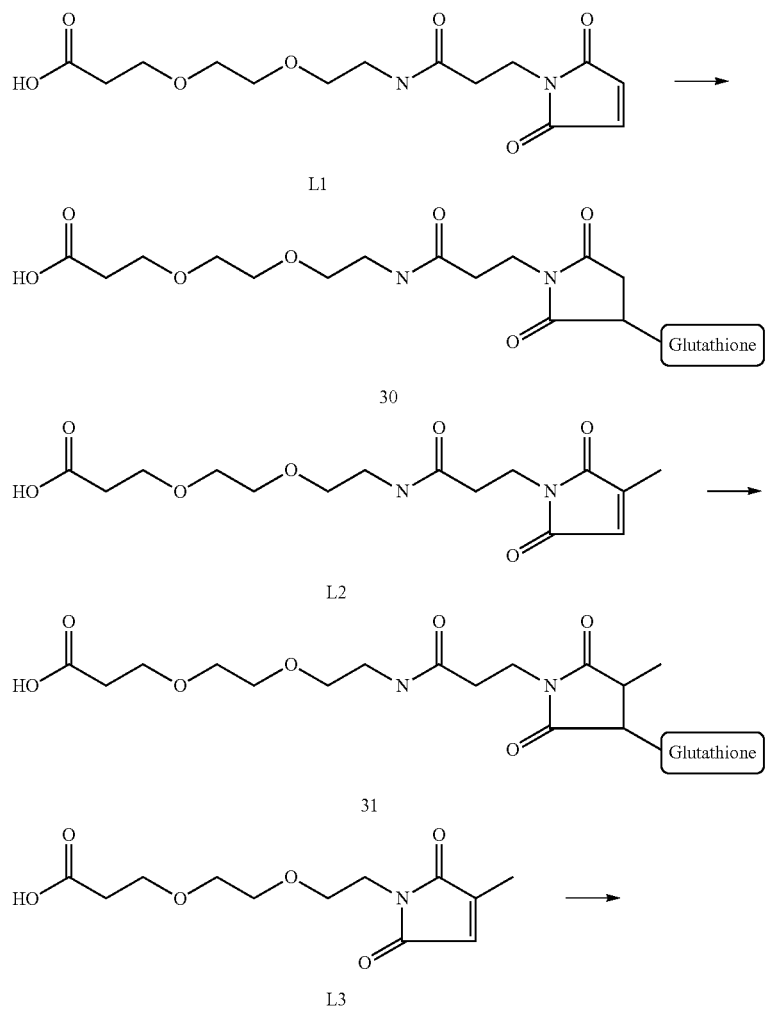

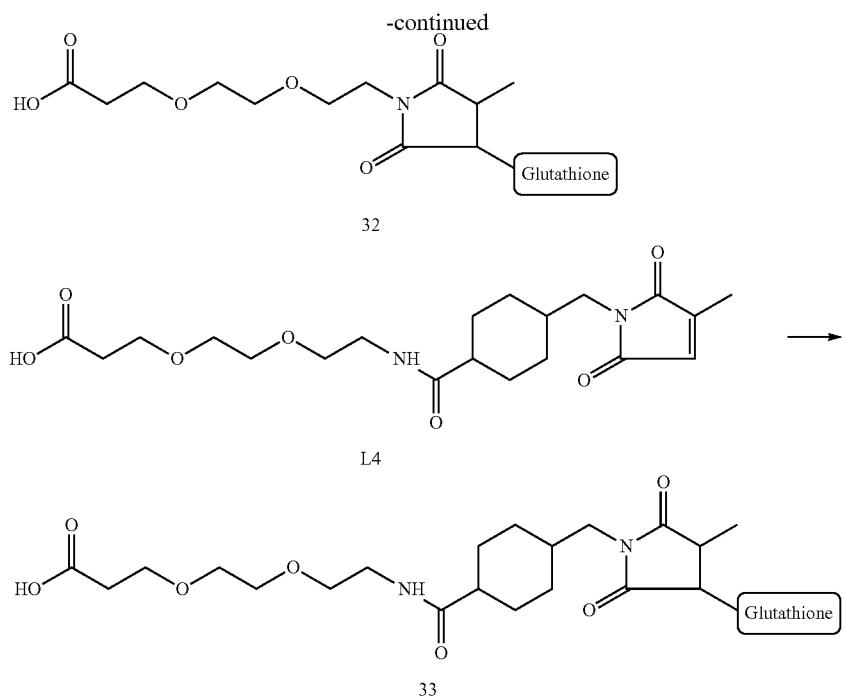

Compounds 30, 31, 32, and 33 were monitored on LC-MS for formation of the ring-opened products as well as glutathione cleavage. These new analogs were examined for their stability at pH=6.5 buffer at 40° C., at pH=7.5 buffer at 40° C., and at pH=7.5 buffer at 4° C., all over a two-week period (Tables 3A-C).

Compounds 30, 31, 32, and 33 were dissolved in a buffer at room temperature. The samples were incubated at 40° C. and the buffer solution was analyzed at the set intervals. At defined intervals, 10 μL of the buffer solution was injected on Agilent high performance liquid chromatography and mass spectrometer for analysis. The eluents from the column were monitored using UV spectrometer at 210 and 254 nm and also using mass spectrometer. The hydrolysis by-products were monitored using mass spectrometer and the percentage hydrolysis was calculated based on the total ion current of a particular mass.

It was evident from the LC-MS data showing % hydrolysis in Tables 3A-3C that the modified maleimide rings of L2, L3 and L4 (31-33) were 5-10 times more stable at pH=6.5 at 40° C. compared to maleimide ring in L1 (30), 4-15 times more stable at pH=7.5 buffer at 40° C., and up to 20 times more stable at pH=7.5 buffer at 40° C. The results of the glutathione conjugations (including the data in Tables 3A, 3B and 3C) were discussed at the IBC Conference "Beyond Antibodies/Protein Engineering Design", San Diego, 21-23 Sep. 2009.

TABLE 3A

Stability Studies at 40° C., pH = 6.5 (10 mM His, 130 mM Gly, 130 mM Suc buffer).

| | Cmpd # | 0 hr % | 1 hr % | 5 hr % | 24 hr % | 48 hr % | 72 hr % | 96 hr % | 120 hr % | 168 hr % | 192 hr % |
|---|---|---|---|---|---|---|---|---|---|---|---|
| L1 | 30 | 0.0 | 0.4 | 0.6 | 4.9 | 11.6 | 14.8 | 18.3 | 17.0 | 25.0 | 25.9 |
| L2 | 31 | 0.1 | 0.1 | 0.3 | 0.8 | 1.8 | 2.6 | 3.0 | 3.1 | 5.0 | 5.1 |
| L3 | 32 | 0.0 | 0.1 | 0.3 | 0.9 | 1.7 | 2.4 | 2.8 | 4.2 | 4.6 | 4.9 |
| L4 | 33 | 0.1 | 0.1 | 0.1 | 0.3 | 0.4 | 0.6 | 0.6 | 0.3 | 1.1 | 1.1 |

TABLE 3B

Stability Studies at 40° C., pH = 7.5 (100 mM His, 200 mM Gly, 200 mM Suc).

| | Cmpd # | 0 hr % | 1 hr % | 5 hr % | 24 hr % | 48 hr % | 72 hr % | 96 hr % | 120 hr % | 144 hr % | 168 hr % | 264 hr % | 336 hr % |
|---|---|---|---|---|---|---|---|---|---|---|---|---|---|
| L1 | 30 | 0.1 | 0.3 | 2.0 | 10.0 | 15.0 | 29.0 | | | | | | |
| L2 | 31 | 0.1 | 0.2 | 0.6 | 3.2 | 4.6 | 7.1 | 8.2 | 9.4 | 12.6 | 12.2 | 13.1 | 15.0 |
| L3 | 32 | 0.1 | 0.1 | 0.1 | 1.0 | 1.1 | 2.2 | 2.8 | 3.3 | 3.3 | 3.9 | 4.4 | 5.0 |
| L4 | 33 | 0.1 | 0.2 | 0.3 | 0.6 | 1.8 | 2.8 | 3.0 | 4.3 | 4.1 | 4.7 | 6.5 | 8.8 |

TABLE 3C

Stability Studies at 4° C., pH = 7.5 (100 mM His, 200 mM Gly, 200 mM Suc).

| Cmpd # | 0 hr % | 1 hr % | 5 hr % | 24 hr % | 48 hr % | 72 hr % | 96 hr % | 120 hr % | 144 hr % | 168 hr % | 264 hr % | 336 hr % |
|---|---|---|---|---|---|---|---|---|---|---|---|---|
| L1 | 30 | 0.1 | 0.1 | 0.1 | 0.7 | 2.0 | 2.2 | 4.4 | 5.5 | 6.9 | 7.5 | 8.7 | 12.2 |
| L2 | 31 | 0.1 | 0.1 | 0.1 | 0.1 | 0.2 | 0.2 | 0.2 | 0.1 | 0.4 | 0.3 | 0.6 | 0.7 |
| L3 | 32 | 0.1 | 0.1 | 0.0 | 0.2 | 0.3 | 0.3 | 0.4 | 0.6 | 0.6 | 0.7 | 1.1 | 1.3 |
| L4 | 33 | 0.1 | 0.1 | 0.1 | 0.2 | 0.2 | 0.2 | 0.1 | 0.3 | 0.3 | 0.2 | 0.5 | 0.6 |

Example 42

Stability of Linkers L1-L4 Conjugated to FGF21

The following experiment was performed to investigate the chemical stability over 2 weeks of the four linkers upon conjugation to FGF21: each linker was conjugated to FGF21, placed at +4° C. storage conditions, and aliquots were removed and quenched by freezing at specific time points, and linker stability was monitored by LCMS analysis.

The four linkers were dissolved in DMSO from lyophilized stock material. FGF21ΔH-A129C protein was partially reduced with 0.1 mM TCEP for 30 min prior to addition of the linker stock at a 1:1 linker:protein ratio; FGF21ΔH-A129C protein concentration in the conjugation reaction was 5 mg/ml. L1 was reacted with protein for 30 mins; L2, L3 and L4 were reacted for 2 hrs. The conjugation reaction was quenched by removal of excess linkers through size-exclusion resin. Conjugated FGF21ΔH-A129C protein was placed at +4° C. for stability storage. Aliquots were removed at t=0 (prior to stability storage) and at t=1, 3, 8, and 14 days. Analysis of linker stability was performed by LC-MS analysis to determine the relative amount of unconjugated protein, protein+linker conjugation, and single and double hydrolysis events of the conjugated protein+linker.

Linker hydrolysis is the critical analytical variable in this experiment. Hydrolysis was monitored by observing the subsequent addition of $H_2O$ to the FGF21-linker complex. A single addition of $H_2O$, +(1) $H_2O$, likely indicates the hydrolysis of the active AZD group that is present on all 4 linkers. The addition of a second $H_2O$ molecule, +(2) $H_2O$, is a strong indicator of hydrolysis (eg—chemical instability) in the linker. L1 is particularly susceptible because of the presence of a maleimide functional group.

The experimental results in Table 4 below demonstrate that L1 undergoes the largest increase in +(2) $H_2O$. At t=0, each of L1-L4 had a measured value of +(2) $H_2O$ between 6-8% of the total measured protein. During the 2 weeks these samples were monitored, the +(2) $H_2O$ observed in L1 had increased to 18% while the value for each of the remaining linkers L2-L4 was constant at 6-8%. This data suggests that L1 is relatively unstable compared to L2-L4.

TABLE 4

Hydrolysis analysis of L1-L4 conjugated with FGF21

| Linker | Time (hrs) | 0 linker | 1 linker | +(1) H2O | +(2) H2O |
|---|---|---|---|---|---|
| L1 | 0 | 13 | 49 | 30 | 8 |
| L1 | 24 | 14 | 41 | 34 | 11 |
| L1 | 72 | 14 | 40 | 35 | 11 |
| L1 | 168 | 10 | 33 | 40 | 18 |
| L1 | 336 | 12 | 28 | 41 | 18 |
| L2 | 0 | 22 | 45 | 27 | 6 |
| L2 | 24 | 23 | 43 | 26 | 8 |
| L2 | 72 | 24 | 37 | 32 | 8 |
| L2 | 168 | 24 | 40 | 29 | 7 |
| L2 | 336 | 26 | 38 | 28 | 8 |
| L3 | 0 | 19 | 45 | 30 | 6 |
| L3 | 24 | 18 | 47 | 27 | 8 |
| L3 | 72 | 19 | 43 | 30 | 8 |
| L3 | 168 | 19 | 43 | 29 | 8 |
| L3 | 336 | 20 | 43 | 29 | 8 |
| L4 | 0 | 20 | 46 | 28 | 6 |
| L4 | 24 | 20 | 46 | 27 | 7 |
| L4 | 72 | 21 | 42 | 30 | 7 |
| L4 | 168 | 21 | 41 | 32 | 6 |
| L4 | 336 | 22 | 41 | 31 | 6 |

Example 43

Ab-FGF21ΔH-A129C Conjugated with L1-L4

L2-L4 had previously been shown to be more stable than L1 with glutathione conjugations under various conditions (see Tables 3A-C) and FGF21 (Table 4). The modified maleimide linkers L2-L4 were fused to FGF21ΔH-A129C (conjugation efficiencies shown in Table 5), and showed activity in the Glut1 Taqman assay (Table 5): $EC_{50}$ values are normalized against the relative value for FGF21ΔH).

TABLE 5

Conjugation efficiencies of L1-L4

| Linker | [Compound] | FGF21-Linker conjugation | FGF21-Linker-Ab conjugation | Glut1 Taqman activity $EC_{50}$ (nM) Relative to FGF21ΔH |
|---|---|---|---|---|
| L1 | 30 | 95% | 95% | 1.68 |
| L2 | 31 | 67% | 95% | 1.00 |
| L3 | 32 | 87% | 89% | 0.35 |
| L4 | 33 | 90% | 94% | 2.71 |

Figure 2B:
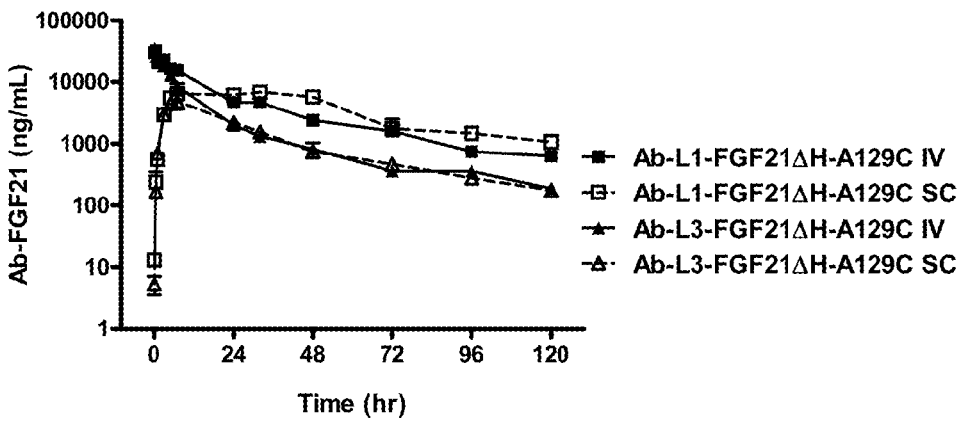
Figure 2C:
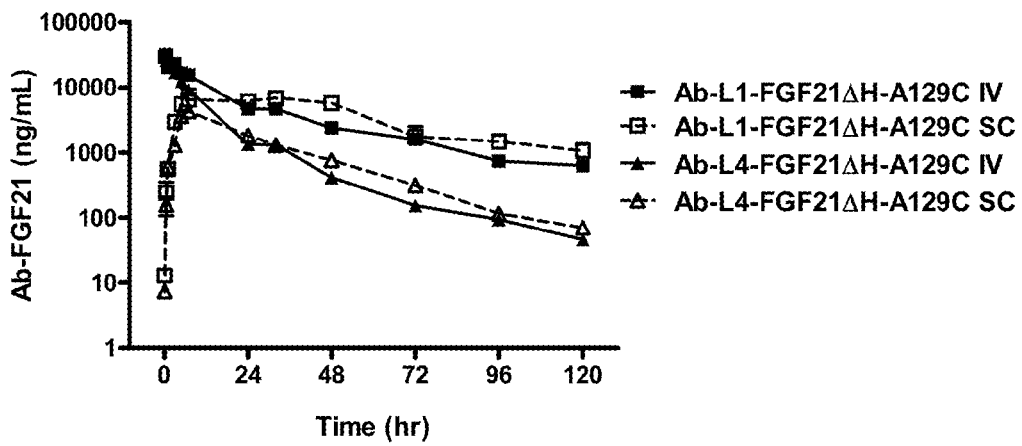

However, despite the foregoing, Ab-L2-FGF21ΔH-A129C, Ab-L3-FGF21ΔH-A129C, Ab-L4-FGF21ΔH-A129C were each less stable in vivo than Ab-L1-FGF21ΔH-A129C. This was evident as lower sustained levels in the circulation after IV dosing, and lower peak and sustained levels in the circulation after SC dosing (FIGS. 2A-C, Table 6). Surprisingly, these results ran counter to the results of the stability studies conducted with the linkers fused to a small peptide in buffer systems.

TABLE 6

Mouse PK parameters of FGF21 conjugates with L1, L2, L3,
and L4 following IV and SC administration at 3 mg/kg

| Cmpd | T½ (hr) IV | T½ (hr) SC | AUC (hr*ug/ml) IV | AUC (hr*ug/ml) SC | SC Bioavailability (%) |
|---|---|---|---|---|---|
| Ab-L1-FGF21ΔH-A129C | 33 | 33 | 491 | 511 | ~100 |
| Ab-L2-FGF21ΔH-A129C | 37 | 23 | 314 | 165 | 53 |
| Ab-L3-FGF21ΔH-A129C | 32 | 13 | 254 | 129 | 51 |
| Ab-L4-FGF21ΔH-A129C | 22 | 14 | 219 | 106 | 48 |

These results were borne out in an additional study in mouse serum. FGF21ΔH-A129C was conjugated to h38C2 using each of L1, L2, L3 and L4. Each sample was diluted in mouse serum to 0.3 mg/ml and incubated at 37° C. before freezing, followed by subsequent analysis by 2DLC/MS. Compared against a reference standard, Ab-L1-FGF21ΔH-A129C was detected at 149% after 5 mins, 66% after 34 hrs, 81% after 72 hrs, and was undetectable by 120 hrs. In contrast, Ab-L2-FGF21ΔH-A129C, Ab-L3-FGF21ΔH-A129C, Ab-L4-FGF21ΔH-A129C were undetectable in all samples.

Example 44

Rat Study of Ab-FGF21ΔH-A129C Conjugated with L1 & L2

Figure 3A:
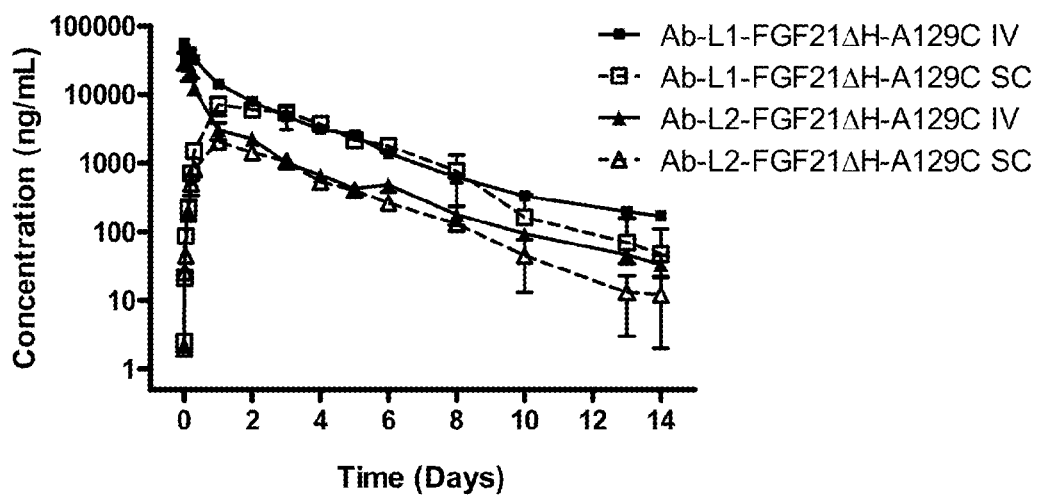
FIG. 3A. Single dose rat pharmacokinetic study with Ab-FGF21ΔH-A129C conjugated with L-1 in comparison with L-2. Adult male Sprague Dawley rats were dosed either IV or SC at 3 mg/kg. For both routes of administration, the conjugate with L-1 performed better than the L-2 conjugate with respect to half-life (~39 hrs SC and ~60 hrs IV for L-1 conjugate, ~33 hrs SC and ~52 hrs IV for L-2 conjugate) and SC bioavailability (~52% for L-1 conjugate, 36% for L-2 conjugate).

Single dose pharmacokinetics (PK) of two versions of Ab-FGF21ΔH-A129C differing by the linker used to conjugate the FGF21 protein to the antibody scaffold were determined in male Sprague Dawley rats. Rats were dosed IV or SC (3 mg/kg) with either Ab-L1-FGF21ΔH-A129C (maleimide linker) or Ab-L2-FGF21ΔH-A129C (methyl maleimide linker), and blood samples were drawn at intervals from 5 mins to 14 days post dose. Serum Ab-FGF21ΔH-A129C levels were determined by ELISA, in which the FGF21 conjugate was captured via a monoclonal antibody specific for FGF21 and detected by anti-human Fc. The resulting PK data demonstrated that the Ab-L1-FGF21ΔH-A129C conjugate had superior PK characteristics ($T_{1/2}$: IV=60 hrs, SC=38 hrs; SC bioavailability=52%) in comparison with the Ab-L2-FGF21ΔH-A129C conjugate ($T_{1/2}$: IV=52 hrs, SC=33 hrs; SC bioavailability=36%), (FIG. 3A and Table 7). These results were not anticipated given the results of stability studies conducted in buffer systems with these linkers fused to a small peptide.

TABLE 7

Rat PK parameters of FGF21 conjugates with L1 and L2 following
IV and SC administration at 3 mg/kg (for FIG. 3A)

| Cmpd | T½ (hr) IV | T½ (hr) SC | AUC (hr*ug/ml) IV | AUC (hr*ug/ml) SC | SC Bioavailability (%) |
|---|---|---|---|---|---|
| Ab-L1-FGF21ΔH-A129C | 60 | 38 | 1382 | 717 | 52 |
| Ab-L2-FGF21ΔH-A129C | 52 | 33 | 419 | 152 | 36 |

Example 45

Effect of Ab-FGF21ΔH-A129C with L1 and L2 on Glut1 RNA

3T3-L1 adipocytes were seeded at day 8 in 24-well tissue culture plates (Falcon®, Cat#353047), and incubated in DMEM complete medium (10% FBS, 2 mM L-glutamine, 1% P/S) at 37° C., 5% $CO_2$. The cells were starved (day 12) with serum-free DMEM medium with 0.2% BSA overnight and treated with Ab-L1-FGF21ΔH-A129C and Ab-L2-FGF21ΔH-A129C in serum-free DMEM containing 0.2% BSA at 37° C. for 6 hrs. The medium was aspirated, and then RNA extracted from the cells using the RNeasy mini Kit according to the manufacturer's instructions. RNA was measured at A260 nm using the Spectramax® Plus spectrophotometer.

TABLE 8

Taqman quantitative real-time PCR

| Compound | Glut1 RNA expression EC50 (nM) |
|---|---|
| FGF21ΔH | 3.39 |
| FGF21ΔH-A129C | 16.03 |
| Ab-L1-FGF21ΔH-A129C | 1.72 |
| Ab-L2-FGF21ΔH-A129C | 9.33 |

Stimulation of 3T3-L1 adipocytes by FGF21ΔH, FGF21ΔH-A129C, Ab-L1-FGF21ΔH-A129C, and Ab-L2-FGF21ΔH-A129C resulted in dose-dependent Glut1 induction. Ab-L1-FGF21ΔH-A129C appeared to be more potent than Ab-L2-FGF21ΔH-A129C (Table 8).

Example 46

Linker Length Study

Ab-L1-FGF21ΔH-D79C, Ab-L7-FGF21ΔH-D79C, and Ab-L8-FGF21ΔH-D79C were tested against each other to assess the tolerance of linker length. All showed similar PK (FIG. 3B and Table 9) and comparable potency (data not shown) in cell-based assays.

TABLE 9

Figure 3B:
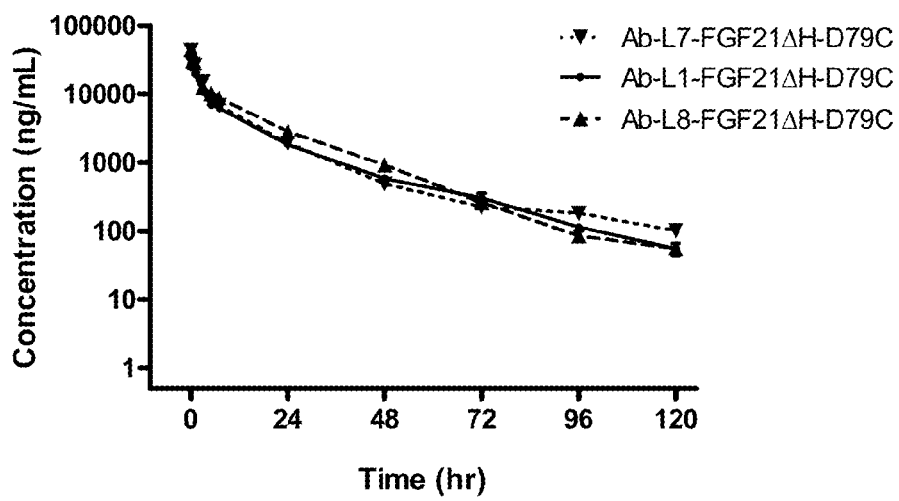
FIG. 3B. Comparison of PK of Ab-L1-FGF21ΔH-D79C, Ab-L7-FGF21ΔH-D79C, and Ab-L8-FGF21ΔH-D79C.
Figure 4A:
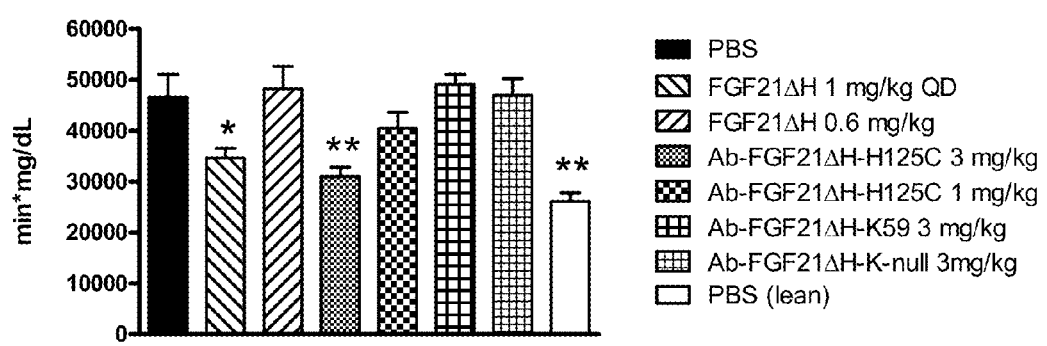

Mouse PK parameters of FGF21 conjugates with L1, L7, and L8
linkers following IV administration at 3 mg/kg (for FIG. 3B)

| Cmpd | IV T½ (hr) | IV AUC (hr*ug/ml) |
|---|---|---|
| Ab-L1-FGF21ΔH-D79C | 19 | 176 |
| Ab-L7-FGF21ΔH-D79C | 27 | 183 |
| Ab-L8-FGF21ΔH-D79C | 15 | 248 |

Example 47

Summary of Residue Positions and Linker Selection

H1C, T40C, D79C, L86C, H125C and A129C were tested as potential conjugation sites using a thiol-maleimide conjugation strategy. Of these, H1C, T40C and L86C showed problems with expression and refolding. D79C, H125C and A129C were explored further as all showed acceptable levels of protein production and demonstrated that the unconjugated mutant protein remained potent. Ab-FGF21ΔH-D79O, Ab-FGF21ΔH-H125C, and Ab-FGF21ΔH-A129C showed similar bioactivity as FGF21ΔH, suggesting that conjugating the antibody at these locations does not interfere the receptor binding. D79C, H125C and A129C have similar stability and bioactivity as FGF21ΔH.

All lysine mutant antibody conjugates tested showed inferior mouse PK to the H125C and A129C antibody conjugates, with IV half-lives of 13-17 hrs (Table 10).

TABLE 10

Summary of conjugation sites on FGF21.

| | Protein yield of fermentation (mg/L) | Glucose uptake EC$_{50}$ (nM) | Glut1 Taqman unconjugated Protein EC$_{50}$ (nM) | Glut1 Taqman Conjugate EC$_{50}$ (nM) | IV T$_{1/2}$ (hr) | SC T$_{1/2}$ (hr) | % SC BioAv | GTT* (% AUC of Ctrl) |
|---|---|---|---|---|---|---|---|---|
| FGF21ΔH** | | 12 (12) | 2.3 (7) | N/A | 0.4 | 0.5 | 96 | 67 |
| K56 | 10-50 | 5.5 | 0.9 (2) | 1.9 (1) | 17 | 13 | 66 | 100 |
| K59 | 10-50 | 0.9 | 0.6 (1) | 6.5 (2) | 13 | ND | N/A | 100 |
| K69 | 10-50 | 5.2 | 1.3 (1) | ND | ND | ND | ND | ND |
| K122 | 10-50 | 1.7 | 2.6 (2) | 1.6 (2) | 16 | 14 | 40 | 100 |
| Knull-P2 | 10-50 | ND | 1.2 (2) | 16.6 (1) | 17 | ND | N/A | 100 |
| Knull-H1K | 10-50 | ND | 6.4 (2) | 4.3 (2) | 16 | 11 | 51 | 99 |
| Knull-S181K | 10-50 | ND | 7.5 (2) | >500 (2) | ND | ND | ND | ND |
| D79C | | 9.9 | 2.1 (4) | 3.7 (3) | 17, 19 | 20, 17 | 55, 70 | 54 |
| L86C | | 62 | ND | ND | ND | ND | ND | ND |
| H125C | | 0.65 | 1.2 (3) | 3.2 (4) | 37 | 32 | 67 | 48, 66 |
| A129C | | 5.7 | 1.4 (6) | 2.7 (7) | 28, 33 | 37, 33 | 69, 100 | 64, 67, 72 |

*3 days after a single SC dose of 3 mg/kg, except 10 mg/kg for D79C and 1 mg/kg Qd for FGF21dH.
**protein;
ND: not determined Although Ala129 was not highly exposed to the solvent, and is less so than D79 or H125, FGF21ΔH-A129C was surprisingly one of the most stable mutants and the best position tested for antibody conjugation. This was unexpected as the mutation is non-conservative. Although not wishing to be bound by theory, there are several possible reasons for the unique suitability of conjugating at A129C. First; Ala129, as well as His125, are both located in the loop region which is flexible in the modelled structure of FGF21. These regions are usually heparin binding sites for other heparin binding FGF members. Since FGF19, FGF21 and FGF23 do not interact with heparin, maintaining sequence fidelity of this region may not be critical for their biological function. The flexibility of the position may be beneficial for antibody-conjugation to avoid interference of receptor binding. Second; Ala129 is surrounded by positively charged resides, namely His125, Arg126, Arg131, and Arg135. This positively charged patch may avoid the SS-dimerization of FGF21ΔH-A129C due to the strong charged repulsion. Third; these charged resides may favour the stabilization of the maleimide linker L1, which in their absence, may generate a carboxylate after ring-opening of maleimide. Thus, when conjugating FGF21 using a maleimide linkage strategy, linking at the specific residue position of A129 appears to be particularly advantageous.

Ab-L1-FGF21ΔH-A129C and Ab-L1-FGF21ΔH-H125C both show high IV half-lives and SC half-lives of at least 30 hrs in murine models as well as good bioavailability Both conjugates demonstrate potency below 4 nM in the Glut1 Taqman assay. In general, Ab-L1-FGF21ΔH-A129C shows slightly improved half-life and potency compared to Ab-L1-FGF21ΔH-H125C. Use of L1 in Ab-L1-FGF21ΔH-A129C also showed surprising in vivo advantages over what in vitro tests suggested, and appeared overall the most advantageous linker compared with those tested.

The specific combination of the components of Ab-L1-FGF21ΔH-A129C, (antibody, linker, linking residue position, linking residue, protein) appear to provide the optimum in half-life, bioavailability, potency, activity, ease of production, and resistance to hydrolysis compared with multiple alternatives.

Example 48

Efficacy of Compounds

Figure 5A:
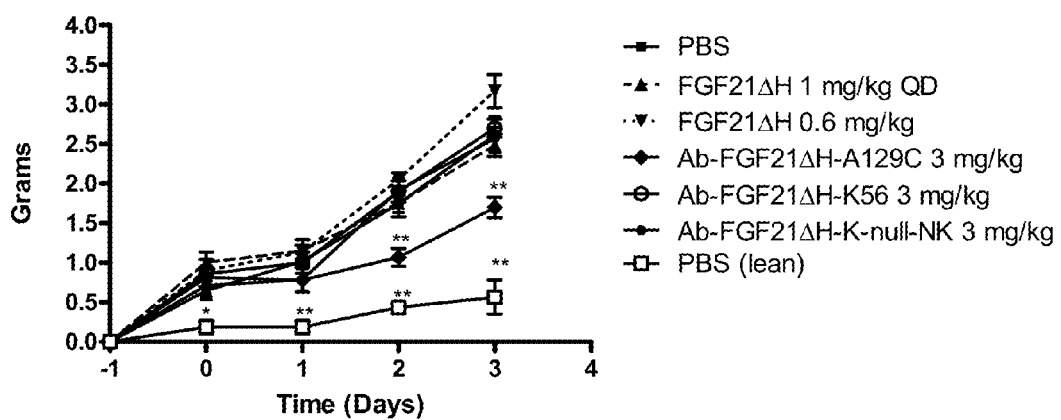
FIGS. 5A and 5B. Cumulative body weight (A) and liver weight (B) change during OGTT in ob/ob mice given a single SC dose (mean body weight (g) in square rackets, mean liver weight (g) in curly brackets): Vehicle [2.6] {2.4}, FGF21ΔH (1 mg/kg [2.5] {2.2}), FGF21ΔH (0.6 mg/kg [3.2] {2.4}), Ab-FGF21ΔH-A129C (3 mg/kg[1.7] {2.0}) (conjugated with L1), Ab-FGF21ΔH-K59 (3 mg/kg [2.7] {2.4}) (conjugated with L5), Ab-FGF21ΔH-Knull-H1K (3 mg/kg [2.6] {2.4}) (conjugated with L5), lean control [0.6] {1.0}. *P<0.05, **P<0.01 vs PBS by two-way ANOVA (A) and one-way ANOVA (B).
Figure 5B:
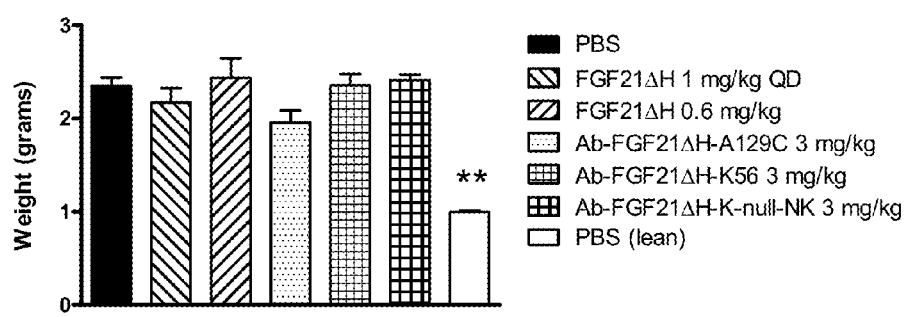

Glucose tolerance was tested for in ob/ob mice treated with compounds Ab-FGF21ΔH-K56 and Ab-FGF21ΔH-Knull-H1K. Both compounds compared poorly against Ab-FGF21ΔH-H125C (FIGS. 4A and 4B) and Ab-FGF21ΔH-A129C (FIGS. 5A and 5B). In contrast, Ab-FGF21ΔH-D79C and Ab-FGF21ΔH-H125C were shown to improve glucose tolerance and reduce body weight gain (FIGS. 4A, 4B, 6A, 6B, 6C, 6D, and Table 11).

TABLE 11

Figure 6A:
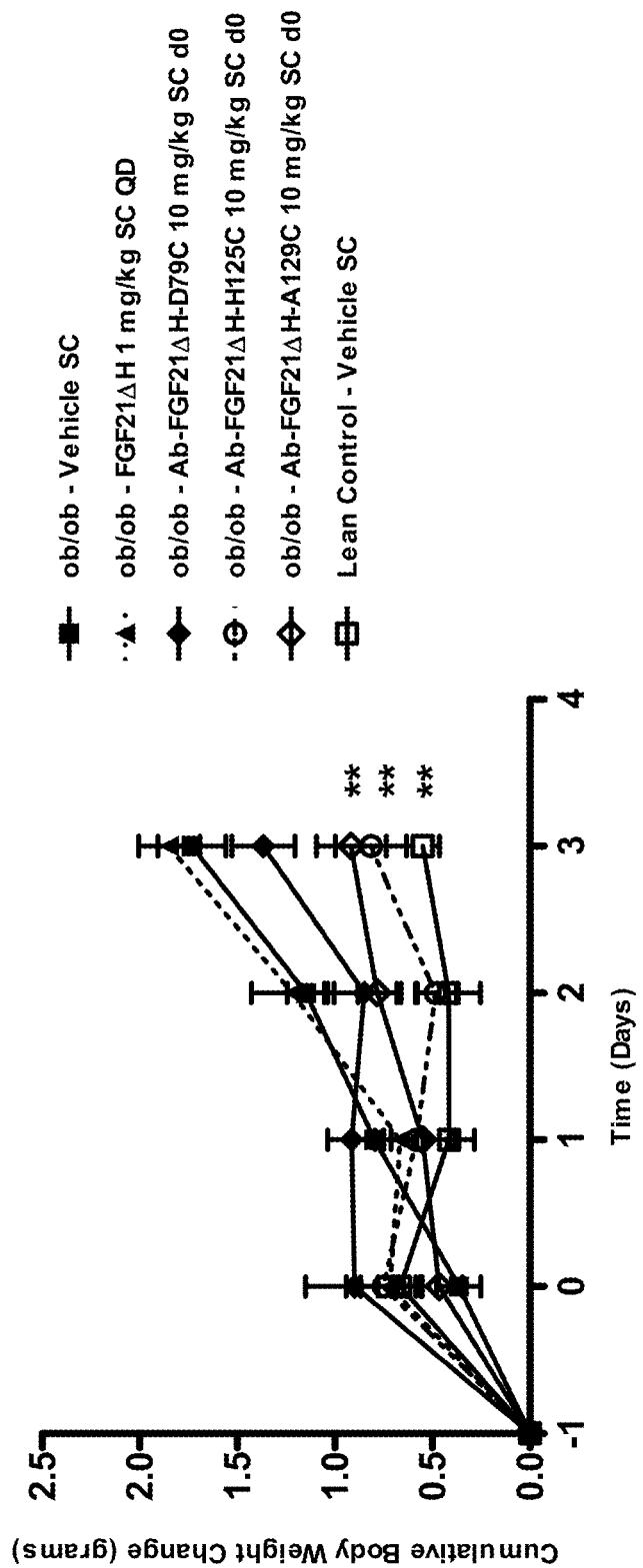
FIG. 6A. Cumulative body weight change in ob/ob mice given a single dose (mean body weight (g) in square brackets): Vehicle [1.7], FGF21ΔH [1.9], FGF21ΔH-D79C (2 mg/kg [2.1]), Ab-FGF21ΔH-D79C (10 mg/kg [1.4]), Ab-FGF21ΔH-H125C (10 mg/kg [0.8]), and Ab-FGF21ΔH-A129C (10 mg/kg [0.9]), lean vehicle [0.6]. d0: day 0. All Ab conjugates used L1. **P<0.01 vs PBS by two-way ANOVA.
Figure 6B:
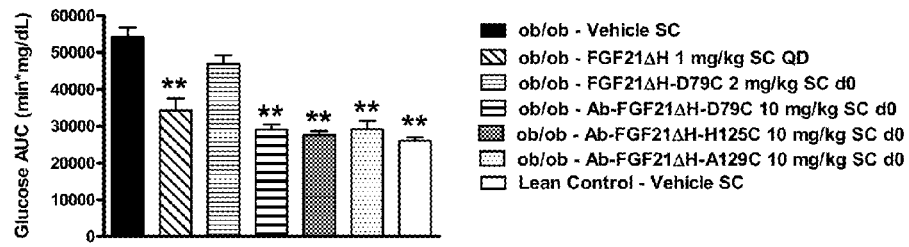
FIG. 6B. Glucose AUC during OGTT in ob/ob mice given a single dose (mean glucose AUC % in square brackets): vehicle [100], FGF21ΔH [63], Ab-FGF21ΔH-D79C (2 mg/kg [86]), FGF21ΔH-D79C (10 mg/ml [54]), Ab-FGF21ΔH-H125C (10 mg/ml [51]), and Ab-FGF21ΔH-A129C (10 mg/kg [54]), lean control [48]. All Ab conjugates used L1. **P<0.01 vs Vehicle by one-way ANOVA.
Figure 6C:
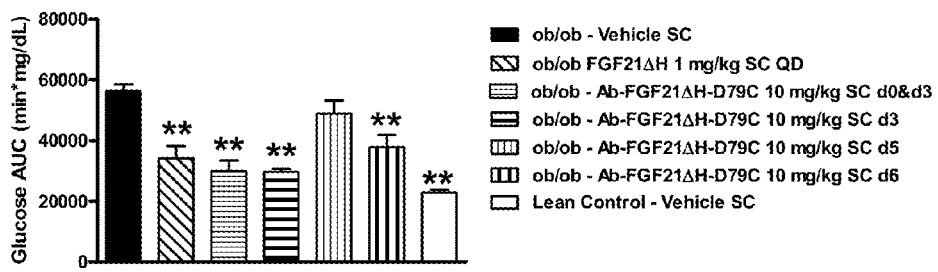
FIG. 6C. Glucose AUC during OGTT in ob/ob mice dosed with FGF21ΔH and Ab-FGF21ΔH-D79C, (10 mg/kg). Ab-FGF21ΔH-D79C was conjugated with Linker-1. **P<0.01 vs Vehicle.
Figure 6D:
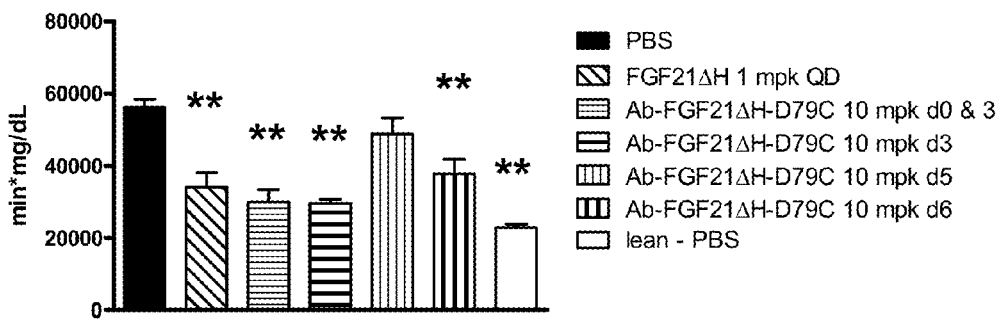
FIG. 6D. Glucose AUC during OGTT in ob/ob mice dosed with FGF21ΔH and Ab-FGF21ΔH-D79C (10 mg/kg) on day 6. Ab-FGF21ΔH-D79C was conjugated with L1. **P<0.01 vs ob/ob-PBS.
Figure 6E:
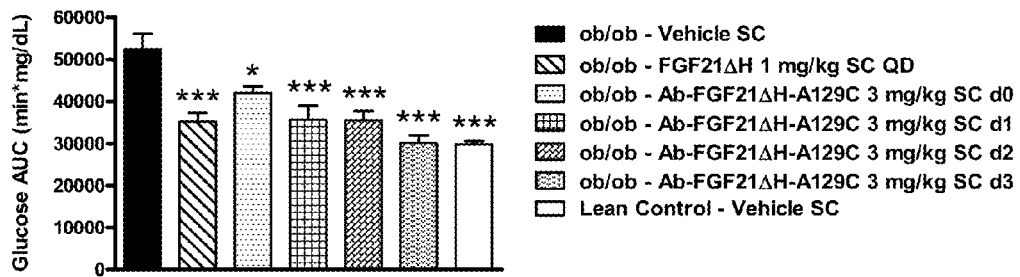
FIG. 6E. Glucose AUC during OGTT conducted on d6 in ob/ob mice given a single dose of Ab-FGF21ΔH-A129C on day 0, 1, 2, or 3 (3 mg/kg). Ab-FGF21ΔH-A129C was conjugated with L1. *P<0.05, ***P<0.001 vs PBS by one-way ANOVA.
Figure 6F:
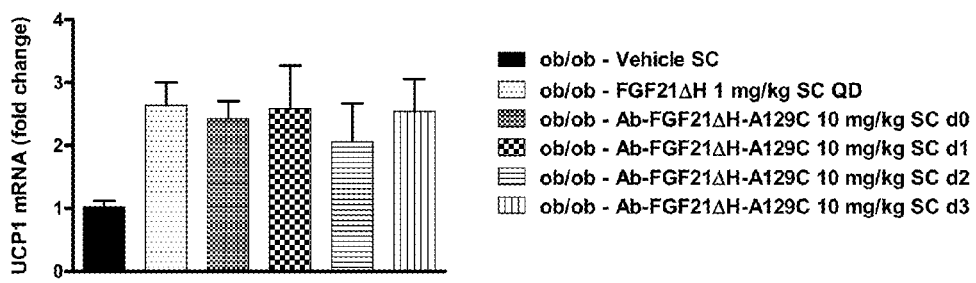
FIG. 6F. A single dose of Ab-FGF21ΔH-A129C increases Ucp1 expression in white adipose tissue in ob/ob mice (10 mg/kg). Ab-FGF21ΔH-A129C was conjugated with L1.
Figure 6G:
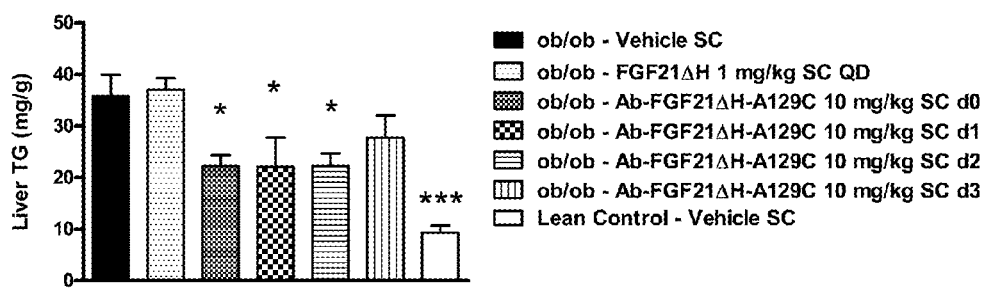
FIG. 6G. A single dose of Ab-FGF21ΔH-A129C decreases liver triglycerides in ob/ob mice (10 mg/kg). Ab-FGF21ΔH-A129C was conjugated with L1. *P<0.05, ***P<0.001 vs Vehicle by one-way ANOVA.
Figure 6H:
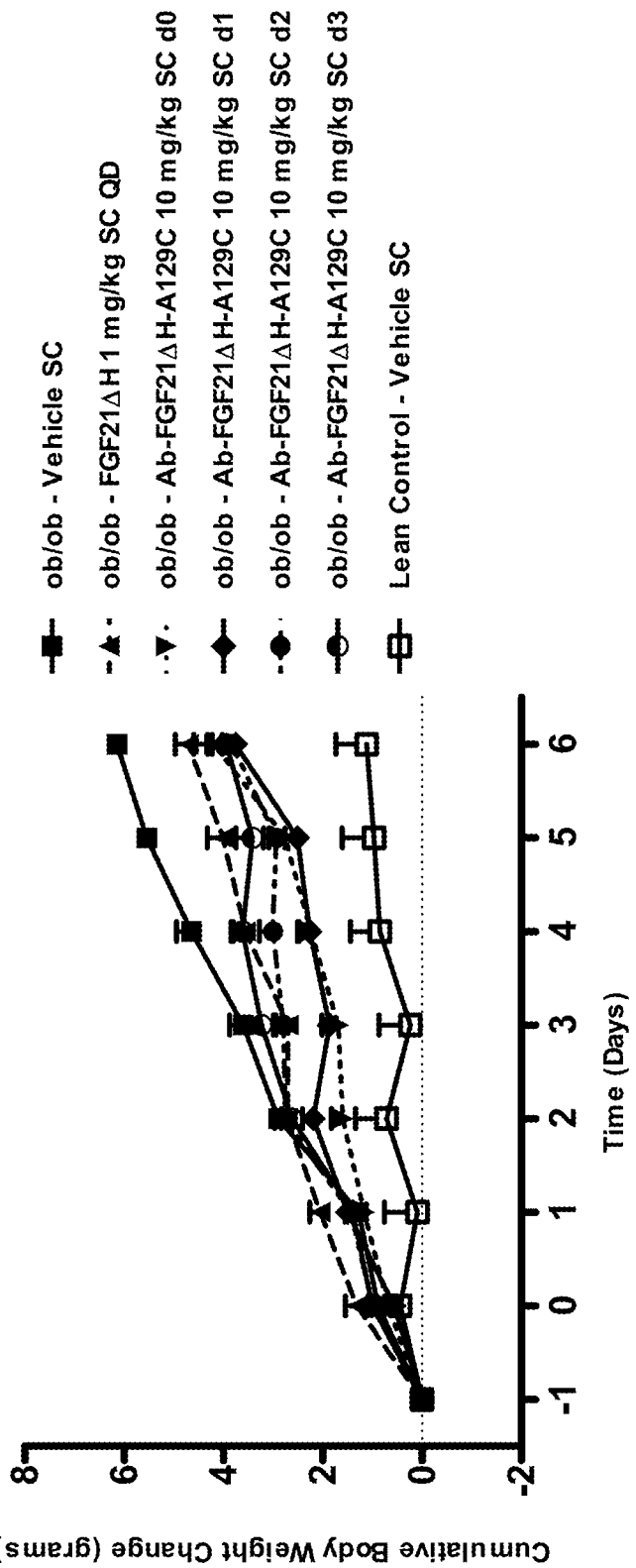
FIG. 6H. Cumulative body weight change in ob/ob mice given a single dose of Ab-FGF21ΔH-A129C on day 0, 1, 2, or 3 (10 mg/kg). Ab-FGF21ΔH-A129C was conjugated with L1.

Glucose AUC during the OGTT conducted on day 6 after SC injection of Ab-FGF21ΔH-D79C at 10 mg/kg at indicated time in ob/ob mice (see FIGS. 6C and 6D)

| Treatment | Mean Glucose AUC (% of vehicle control) |
|---|---|
| Vehicle | 100 |
| FGF21ΔH 1 mg/kg QD | 61 |
| Ab-FGF21ΔH-D79C, day 0 & 3 | 53 |
| Ab-FGF21ΔH-D79C, day 3 | 53 |
| Ab-FGF21ΔH-D79C, day 5 | 87 |
| Ab-FGF21ΔH-D79C, day 6 | 67 |
| Lean control (vehicle) | 41 |

Figure 7A:
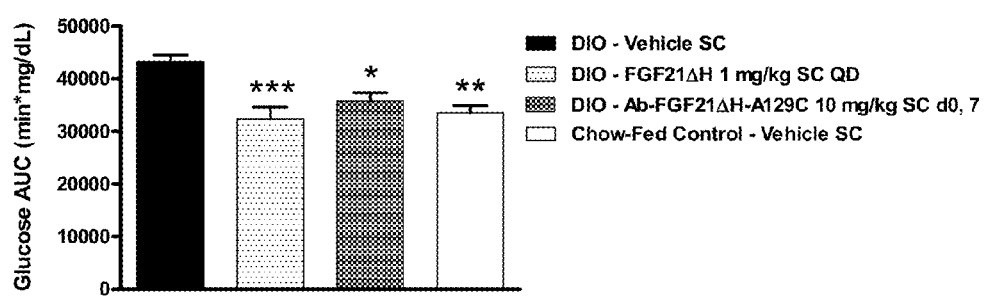
FIG. 7A. Repeat dose of Ab-FGF21ΔH-A129C (10 mg/kg on day 0 and 7) improves glucose tolerance in DIO mice. OGTT was conducted on day 10. Ab-FGF21ΔH-A129C was conjugated with L1. *P<0.05, P<0.01, *P<0.001 vs Vehicle by one-way ANOVA.
Figure 7B:
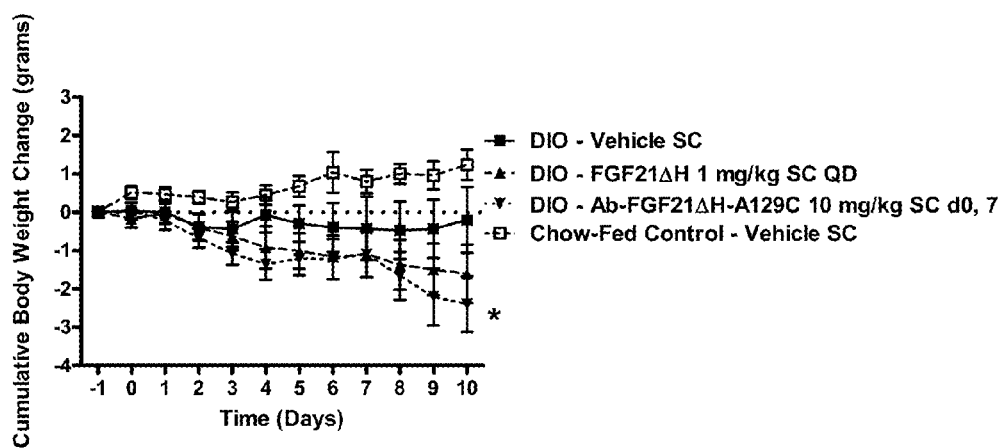
FIG. 7B. Cumulative body weight change in DIO mice given two doses of Ab-FGF21ΔH-A129C on day 0 and 7 (10 mg/kg). Ab-FGF21ΔH-A129C was conjugated with L1. *P<0.05, vs Vehicle by two-way ANOVA.
Figure 7C:
FIG. 7C. Repeat dose of Ab-FGF21ΔH-A129C increases Ucp1 expression in white adipose tissue in DIO mice (10 mg/kg). Ab-FGF21ΔH-A129C was conjugated with L1. **P<0.01 vs Vehicle by one-way ANOVA.
Figure 7D:
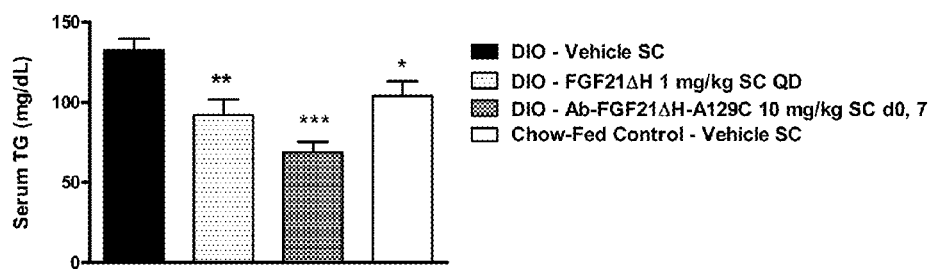
FIG. 7D. Ab-FGF21ΔH-A129C lowers serum triglycerides in DIO mice (10 mg/kg).
Figure 7E:
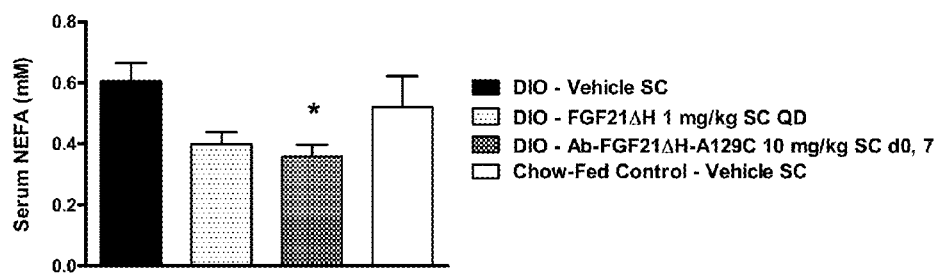
FIG. 7E. Ab-FGF21ΔH-A129C lowers serum non-esterified fatty acids in DIO mice (10 mg/kg).
Figure 7F:
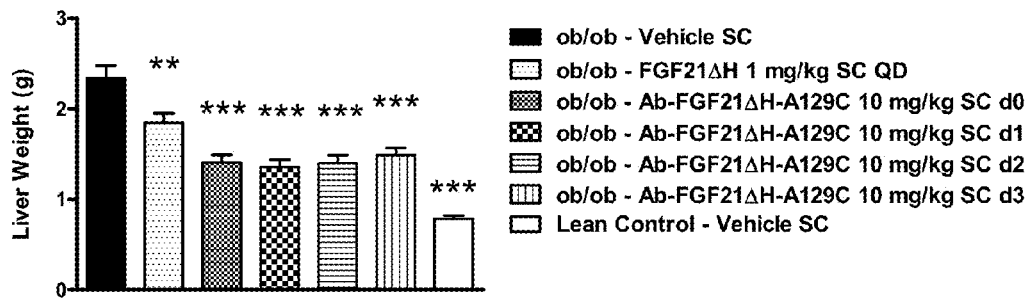
FIG. 7F. Ab-FGF21ΔH-A129C Liver weight. Ab-FGF21ΔH-A129C was conjugated with L1. *P<0.05, P<0.01, *P<0.001 vs Vehicle (A, B) and vs PBC (C) by one-way ANOVA.
Figure 7G:
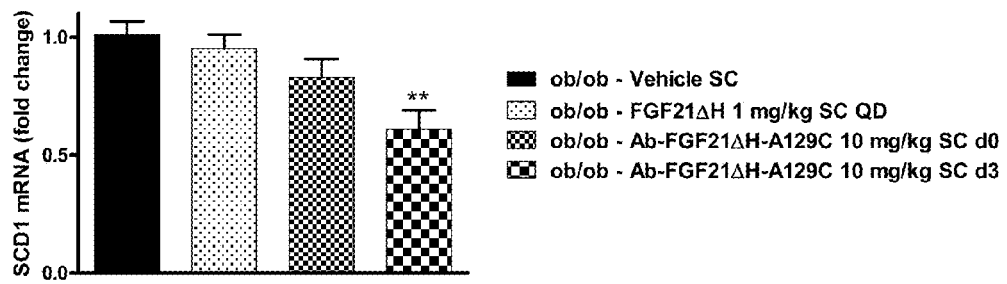
FIG. 7G, 7H, 7i. Effect of Ab-FGF21ΔH-A129C on Hepatic Gene Expression in ob/ob Mice. (7G) SCD1: stearoyl-CoA desaturase 1, (7H) MOGAT2: monoacyglycerol acyltransferase 2 (7i) FoxA2: forkhead transcription factor A2. Ab-FGF21ΔH-A129C was conjugated with L1. **P<0.01 vs Vehicle by one-way ANOVA.
Figure 7H:
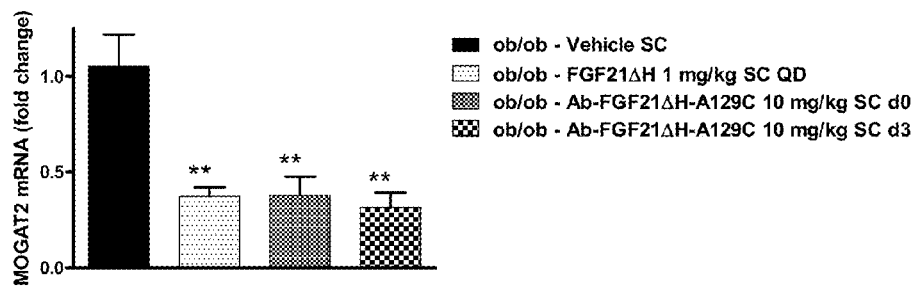
Figure 7I:
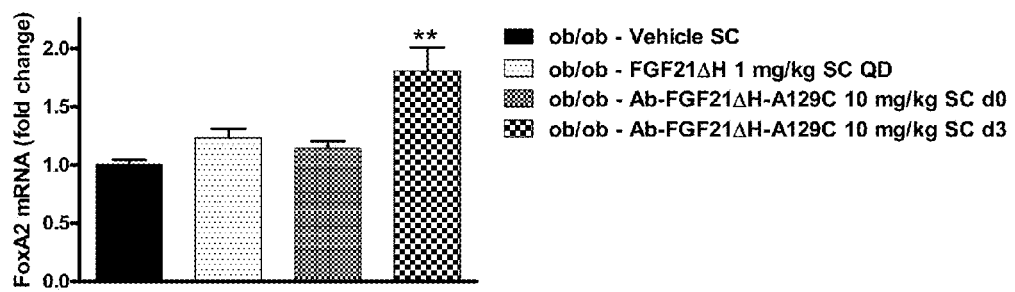

Ab-FGF21ΔH-A129C was found to improve glucose tolerance, and reduced body weight gain, due to increased energy expenditure evidenced by increased Ucp1 expression in white adipose tissue (WAT), and reverses hepatic steatosis in ob/ob mice (FIGS. 6E, 6F, 6G, 6H and Table 12). For Ucp1 expression, frozen visceral WAT samples collected from the in vivo efficacy studies were homogenized. Total RNA was extracted from the tissue homogenates, and Glut1 and GAPDH mRNA expression was measured using a Quantitect Probe RT-PCR kit and running a quantitative real time PCR reaction in a Taqman machine (Applied Biosystems). The effect of treatment was determined by a fold change in Glut1 mRNA levels normalized by the GAPDH mRNA levels from each sample. Ab-FGF21ΔH-A129C caused body weight loss due to increased energy expenditure as suggested by increased Ucp1 expression in WAT, reduced serum triglycerides and fatty acid levels in DIO mice and decreased liver weight (FIGS. 7A, 7B, 7C, 7D, 7E, and Table 13). A reduction in liver weight was also observed in ob/ob mice (FIG. 7F and Table 14). Further tests in ob/ob mice demonstrated a reduction in RNA levels of stearoyl-coenzyme A desaturase-1 (SCD1), monoacylglycerol O-acyltransferase (MOGAT2), and forkhead box A2 (FoxA2), (FIGS. 7G, 7H and 7i and Table 15).

TABLE 12

Results after a single SC injection of Ab-FGF21ΔH-A129C at day 6 in ob/ob mice; see FIGS. 6E, 6F, 6G, 6H.

| Treatment | Glucose AUC during OGTT 3 mg/kg. | UCP1 mRNA expression in WAT 10 mg/kg. | Triglycerides content in liver 10 mg/kg. | Body weight change from day −1 10 mg/kg. |
|---|---|---|---|---|
| Vehicle | 100 | 1.0 | 35.7 | 6.2 |
| FGF21ΔH 1 mg/kg QD | 67 | 2.6 | 37.0 | 4.7 |
| Ab-FGF21ΔH-A129C, day 0 | 80 | 2.4 | 22.2 | 4.2 |
| Ab-FGF21ΔH-A129C, day 1 | 68 | 2.6 | 22.1 | 3.8 |
| Ab-FGF21ΔH-A129C, day 2 | 68 | 2.1 | 22.2 | 3.8 |
| Ab-FGF21ΔH-A129C, day 3 | 57 | 2.5 | 27.7 | 4.0 |
| Lean control (vehicle) | 57 | 0.2 | 9.3 | 1.1 |

TABLE 13

Results on day 10 after a repeat SC injection of Ab-FGF21AH-Δ129C at 10 mg/kg on day 0 & 7 in DIO mice (see FIGS. 7A, 7B, 7C, 7D, 7E)

| Treatment | Glucose AUC during OGTT | Body weight change from day −1 | UCP1 mRNA expression in WAT | Mean values of serum lipids TG (mg/dL) | NEFA (mM) |
|---|---|---|---|---|---|
|  | 100 | −0.2 | 1.00 | 133 | 0.61 |
| FGF21ΔH 1 mg/kg QD | 75 | −1.6 | 1.38 | 92 | 0.40 |
| Ab-FGF21ΔH-A129C, d 0&7 | 83 | −2.4 | 4.02 | 69 | 0.36 |
| Chow-fed control (vehicle) | 78 | +1.2 | 0.42 | 104 | 0.52 |

TABLE 14

Liver weight on day 6 after a single SC injection of Ab-FGF21ΔH-A129C at 10 mg/kg at indicated time in ob/ob mice (for FIG. 7F)

| Treatment | Liver Weight (g) |
|---|---|
| Vehicle | 2.3 |
| FGF21ΔH 1 mg/kg QD | 1.8 |
| Ab-FGF21ΔH-A129C, day 0 | 1.4 |
| Ab-FGF21ΔH-A129C, day 1 | 1.4 |
| Ab-FGF21ΔH-A129C, day 2 | 1.4 |
| Ab-FGF21ΔH-A129C, day 3 | 1.5 |
| Lean control (vehicle) | 0.8 |

TABLE 15

Mean fold changes of mRNA expression using qPCR from liver tissue

| Treatment | SCD1 | MOGAT2 | FoxA2 |
|---|---|---|---|
| Vehicle | 1.01 | 1.05 | 1.00 |
| FGF21ΔH 1 mg/kg QD | 0.95 | 0.37 | 1.23 |
| Ab-FGF21ΔH-A129C, day 0 | 0.83 | 0.38 | 1.14 |
| Ab-FGF21ΔH-A129C, day 3 | 0.61 | 0.31 | 1.81 | samples collected on day 6 after a single SC injection of Ab-FGF21ΔH-A129C at 10 mg/kg at indicated time in ob/ob mice (for FIG. 7G, 7H, 7i).

Example 49

Plasma Drug Levels of Ab-L1-FGF21ΔH-A129C in ob/ob Model

Figure 7J:
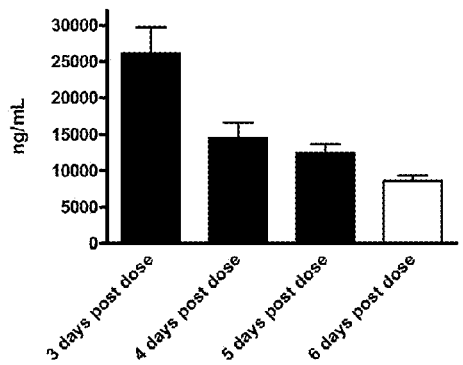
FIG. 7J, 7K. Dose related serum levels of Ab-L1-FGF21ΔH-A129C in ob/ob mice (7J) dosed at 10 mg/kg and (7K) dosed at 3 mg/kg.
Figure 7K:
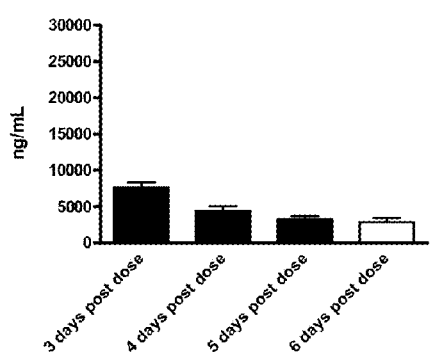

Dose related serum levels of Ab-L1-FGF21ΔH-A129C in ob/ob mice were examined at 3, 4, 5, and 6 days post-dose, following dosing at 10 mg/kg and 3 mg/kg. Serum levels of Ab-L1-FGF21ΔH-A129C were observed to be well maintained (FIGS. 7J and 7K). These results were consistent with the pharmokinetics in healthy animals.

Example 50

In Vivo Effect of Ab-L1-FGF21ΔH-A129C on Insulin Sensitivity

A study was undertaken to determine in vivo effect of Ab-L1-FGF21ΔH-A129C on whole body insulin sensitivity (measured as glucose infusion rate) and hepatic glucose production during a hyperinsulinemic euglycemic clamp in conscious, unrestrained ob/ob mice. Ab-L1-FGF21ΔH-A129C (in 30 mM acetate buffer, pH 4.8) was administered SC twice a week for one week at a dose of 10 mg/kg. The dosing volume was 2 mL/kg per injection. Ab-FGF21ΔH-A129C was injected on day 2 and 5 of the study. Vehicle (30 mM acetate buffer pH4.8) was administered twice a week at a dosing volume of 2 mL/kg per injection on day 2 and day 5 of the study. Mice were treated with ketprofen 2 mg/kg SC and ampicillin 100 mg/kg SC immediately before surgery. Animals (n=8 per group) were randomized according to their day 1 fasted plasma glucose and body weight.

Body weights were recorded on days 1, 4, 7, and 8 of the study. Surprisingly, Ab-L1-FGF21ΔH-A129C did not demonstrate an effect on body weight in this study (data not shown). Fasted plasma glucose was determined on day 1 (4-hr fast) and day 8 (16-hr fast) with Accu-Chek hand-held glucometers (Roche). Ab-L1-FGF21ΔH-A129C had no effect on fasted plasma glucose levels in this study (data not shown).

On day 7 of the study, mice were fasted for 16 hrs before the clamp procedure on day 8. On day 8 catheters were exteriorized and animals connected to the infusion lines. 90 mins before the start of the clamp procedure (−90 min), a 6 μCi bolus of [3-3H] glucose was injected into the jugular vein followed by a 0.1 μCi/min constant infusion until the end of the clamp. Blood was collected at −10 min and 0 min for the determination of basal HGP. At time 0 min the variable glucose infusion (50% dextrose) as well as the constant infusion of insulin 20 mU/kg/min was started. Plasma glucose was measured every 10 min from the tail vein and glucose infusion rates were adjusted according to each animals glucose level until a steady state was reached. At time points 170 min and 180 min blood was collected to determine hepatic glucose production (HGP) under clamped conditions. During the clamp procedure, animals were unrestrained and conscious. Hepatic Glucose Production (HGP) was calculated using the following formula:

HPG=Ra−Rate of cold glucose infusion, where $$Ra = \frac{\text{Glucose Infusion Rate (dpm/min)}}{\text{Blood specific activity (dpm/mg)} \times \text{weight (kg)}} = \text{mg/kg/min}$$

The Rate of appearance (Ra)

(which as steady state = the Rate of disappearance (Rd))

Figure 8A:
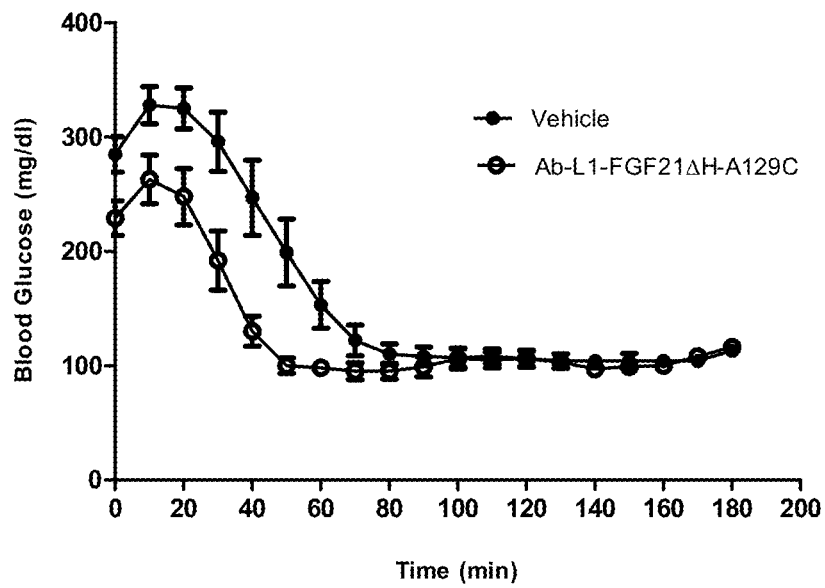
FIG. 8A. Plasma glucose levels over the full period of the hyperinsulinemic euglycemic clamp.
Figure 8B:
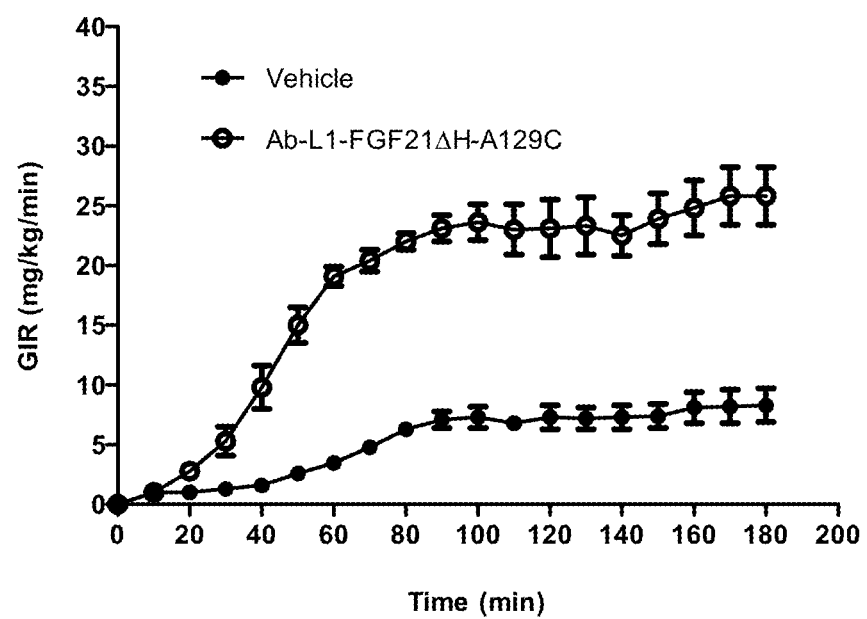
FIG. 8B. Glucose infusion rates over the full period of the hyperinsulinemic euglycemic clamp.
Figure 8C:
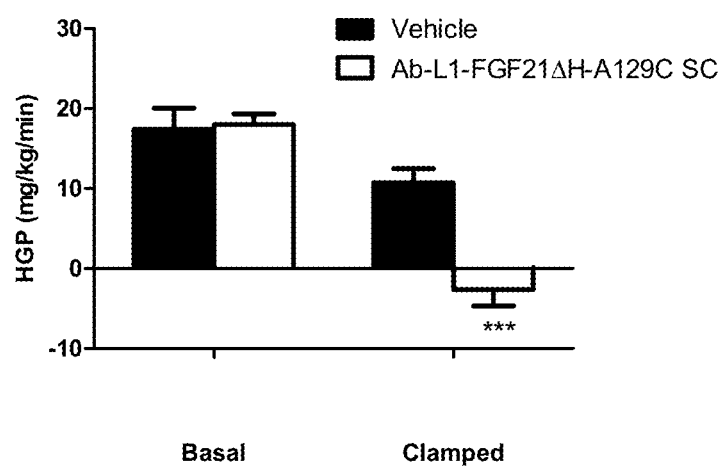
FIG. 8C. Hepatic glucose production under basal and clamped conditions (***=P<0.0001).

Ab-L1-FGF21ΔH-A129C did not affect body weight or fasted plasma glucose in ob/ob mice compared with vehicle-treated animals. All animals were clamped successfully and reached euglycemic plasma glucose levels of 100-110 mg/dl as well as constant glucose infusion rates during the last 30 min of the clamp. Euglycemia (100 mg/dL-110 mg/dL plasma glucose) was reached in the vehicle- and Ab-L1-FGF21ΔH-A129C-treated groups. Plasma glucose levels were measured over the full period of the hyperinsulinemic euglycemic clamp (FIG. 8A). There was no statistical difference between the vehicle- and Ab-L1-FGF21ΔH-A129C-treated animals during the last 30 min of the experiment (clamp period). Ab-L1-FGF21ΔH-A129C significantly increased the glucose infusion rate (GIR) compared with vehicle (FIG. 8B). Ab-L1-FGF21ΔH-A129C did not alter basal hepatic glucose production (HGP) but significantly suppressed HGP under clamped (hyperinsulinemic) conditions (FIG. 8C).

In conclusion, in this study Ab-L1-FGF21ΔH-A129C significantly increased glucose infusion rates, a measure of whole body insulin sensitivity, and suppressed hepatic glucose production compared with vehicle treated animals without having an effect on body weight or fasted plasma glucose levels.

Example 51

Effect of Ab-L1-FGF21ΔH-A129C in Cynomolgus Macaques

The goal of this study was to evaluate the effects of Ab-L1-FGF21ΔH-A129C on plasma glycemic and lipid indices, as well as on glucose tolerance and inflammatory biomarkers, when administered to obese insulin resistant (pre-diabetic) cynomolgus macaques via twice-weekly SC injections. The study was also designed to determine the duration of pharmacodynamic (PD) effect of Ab-L1-FGF21ΔH-A129C in the monkeys compared to daily dosing with FGF21ΔH.

Twenty-two adult cynomolgus monkeys (*Macaca fascicularis*) were included in the study. The monkeys (13 male, 11 female) were stratified into four treatment groups of 6 individuals, based on sex, body weight, and basal glycemic and lipid indices measured in a baseline plasma sample collected 2 weeks prior to the start of dosing. Animals were maintained on a high fat diet. Animals were dosed for 4 weeks followed by a 4 week washout period. Animals were dosed as follows: twice weekly SC with Ab-L1-FGF21ΔH-A129C in 25 mM Tris, 125 mM NaCl pH 7.0 at 1.5 mg/kg (group A; 4 male (m) 1 female (f)) and 0.15 mg/kg (group B; 3m, 3f), twice weekly s.c. with vehicle (25 mM Tris and 125 mM NaCl at a final pH of 7.0) (group C; 3m, 3f), and once daily (QD) with FGF21ΔH at 0.3 mg/kg (group D; 3m, 2f).

Blood samples were collected weekly during the dosing and washout periods, with the exception that no samples were collected at week 3 of washout. After an overnight fast (16-18 h), monkeys were sedated with ketamine 10-15 mg/kg by intramuscular (IM) injection. Body weights were recorded and blood (5 mL) was collected via percutaneous femoral venipuncture into ethylenediaminetetraacetic acid (EDTA) treated Vacutainer tubes pretreated with ~1.8 trypsin inhibitor units (TIU) Aprotinin (Sigma 0.6 TIU per mL whole blood). Tubes were immediately placed on ice. Plasma was prepared by centrifugation, with the resulting plasma aliquoted and frozen at −80° C.

Plasma drug level sampling was conducted on Days 1, 14, and 28 of the dosing period. Plasma Ab-L1-FGF21ΔH-A129C levels were determined using an enzyme-linked immunosorbent assay (ELISA). Ab-L1-FGF21ΔH-A129C was captured using mouse anti-idiotypic h38C2 and detected with a mixture of biotinylated mouse anti-FGF21 monoclonal antibodies directed to the N- and C-termini of FGF21. The C-terminal detection antibody has specificity for the last 4-5 amino acids of FGF21, while the N-terminal detection antibody was raised against the first 11-12 amino acids of FGF21. The minimum required dilution for the dual-detection reagent assay was 1:20 in 3% BSA phosphate buffered saline. The calibration range was 0.03-10 μg/mL, and the quantification range was 0.03-4 μg/mL.

Data were treated in the same way for each pharmacodynamic endpoint. The baseline value for each individual monkey was subtracted from each timepoint to give a value corresponding to change from baseline. Changes from baseline values were averaged for each timepoint in each treatment group and standard error of the mean (SEM) calculated. Results are reported as mean change from baseline±SEM for each treatment group over the timecourse of the study. For the 0.15 mg/kg and 1.5 mg/kg Ab-L1-FGF21ΔH-A129C treated animals, statistical significance at each timepoint was assessed vs. vehicle using the change from baseline values and a student's T-test (unpaired sample, unequal variance). As there was no vehicle control group for the FGF21ΔH treated animals, the raw data and not the change from baseline value was used to assess statistical significance. In this case a student's T-test (two sided, paired sample) was carried out vs. baseline.

Example 52

Ab-L1-FGF21ΔH-A129C Plasma Drug Levels

Plasma drug levels are shown in Table 16. Measurable drug levels were present 4 hrs after the first dose and at all subsequent timepoints tested

TABLE 16

Ab-L1-FGF21ΔH-A129C plasma drug levels.

| Day | Dose (mg/kg) | Mean (SD) AB-L1-FGF21ΔH-A129C Plasma Concentration by Time (h) | | | |
|---|---|---|---|---|---|
| | | Predose | 1 | 4 | 24 |
| 1 | 0.15 | BLQ | NC | 61.6(52.5) | 60.1(25.0) |
| | 1.5 | BLQ | NC | 221(186) | 335(181) |
| 14 | 0.15 | 31.7(20.8) | 18.6(10.5) | 27.1(10.3) | 27.6(14.3) |
| | 1.5 | 66.4(38.5) | 249(188) | 312(225) | 300(228) |
| 28 | 0.15 | — | — | — | 39.1(51.4) |
| | 1.5 | — | — | — | 73.7(84.8) |

BLQ = Below limit of quantitation (8 ng/mL), NC = not calculated n < 3, — = sample not available for test

Example 53

Body Weight

Figure 9A:
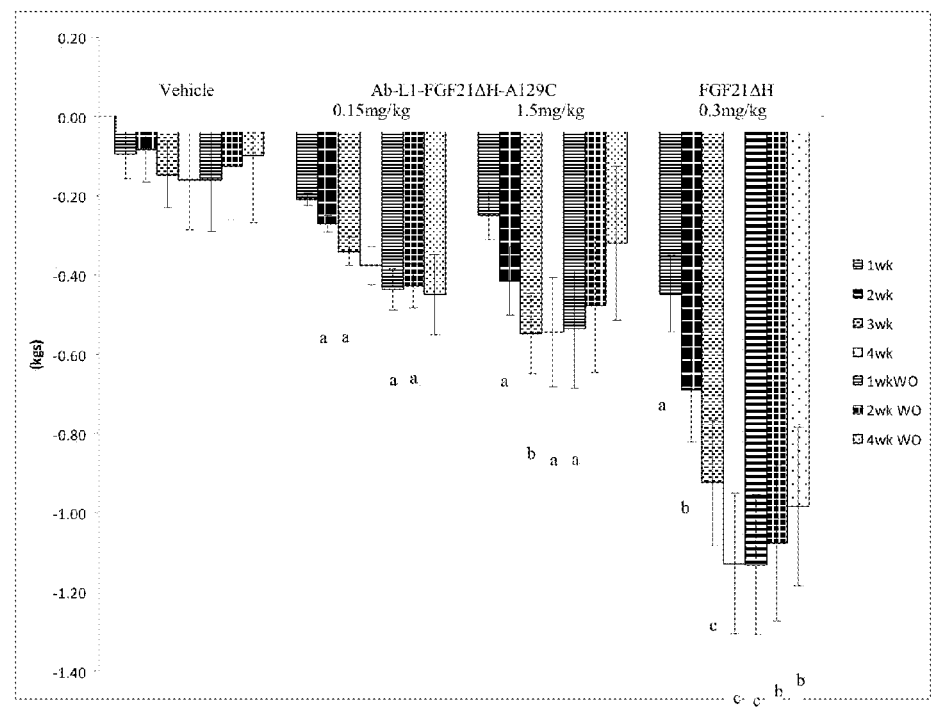

There was a significant decrease in body weight on treatment after 2 weeks in both AB-L1-FGF21ΔH-A129C dose groups and after 1 week in the group treated with FGF21 control protein (FIG. 9A). In all groups weight loss remained depressed during the wash out period although significance was lost by 4 weeks of washout in both AB-L1-FGF21ΔH-A129C groups. FGF21ΔH treated animals exhibited higher weight loss than those treated with AB-L1-FGF21ΔH-A129C. Food intake was not directly measured in these animals but there were no observations of inappetence by the care staff in any of the animals in any treatment group.

Example 54

Fasted Plasma Glucose

Figure 9B:
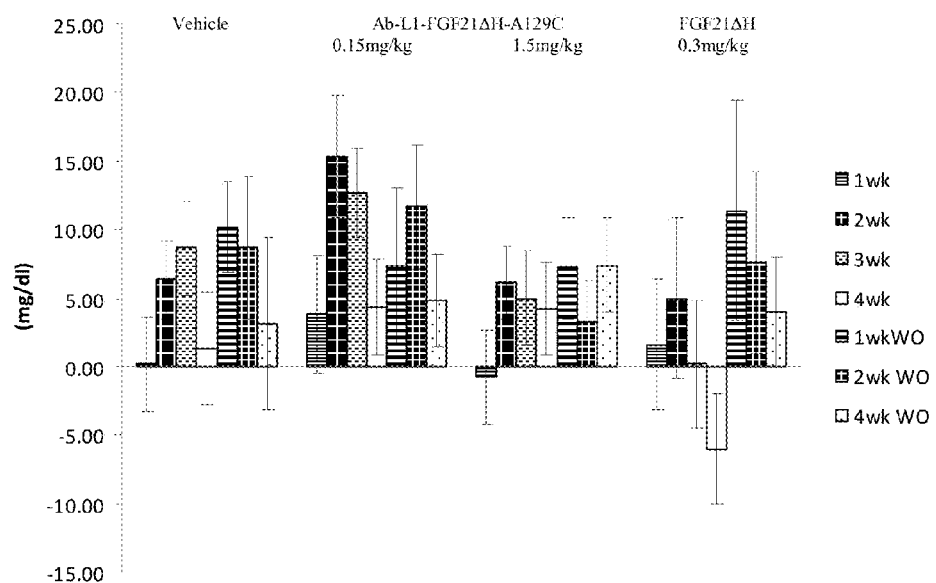

Plasma glucose was measured via an enzymatic colorimetric method using the Ace Alera® Clinical Chemistry Analyzer and reagents (Alfa Wassermann®, Caldwell, N.J.) according to manufacturer's instructions. There was no significant change in fasted plasma glucose (FIG. 9B) across time in any of the treatment groups, indicating that prolonged treatment with AB-L1-FGF21ΔH-A129C does not cause hypoglycemia.

Example 55

Fasted Plasma Insulin

Figure 9C:
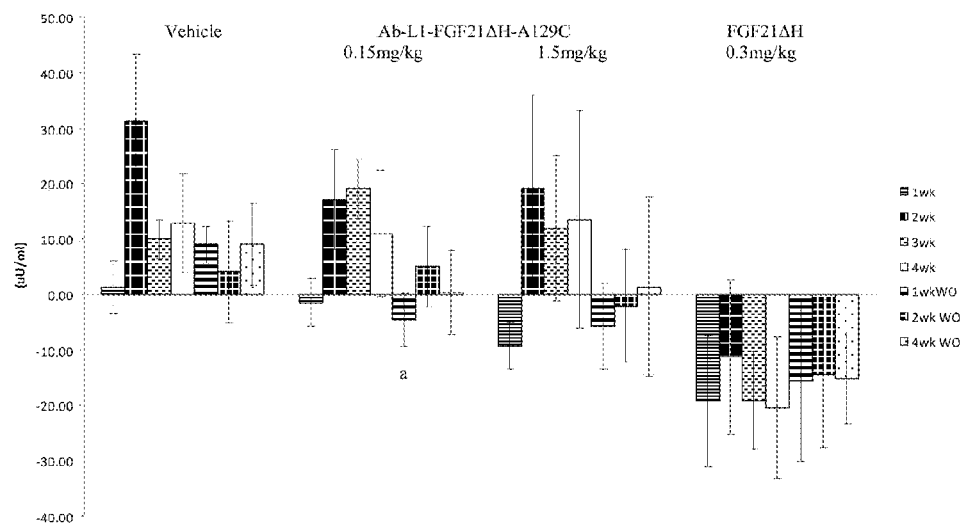

Plasma insulin concentrations were determined using an ELISA kit from Mercodia® (Uppsala, Sweden) according to manufacturer's instructions. There was no significant change in fasted plasma insulin (FIG. 9C) levels across time in any of the treatment groups.

Example 56

Fasted Plasma Fructosamine

Figure 9D:
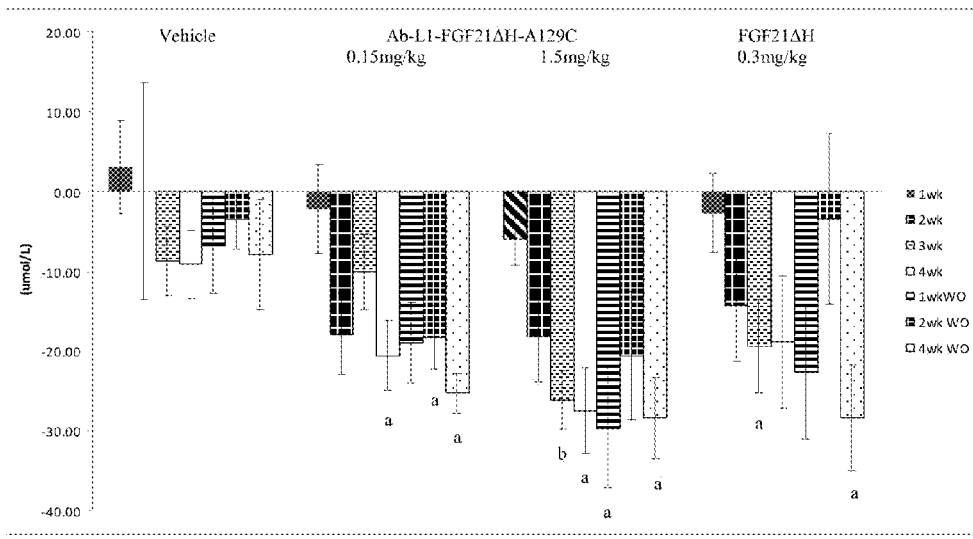

Plasma fructosamine was measured via an enzymatic colorimetric method using the Ace Alera Clinical Chemistry Analyzer using a kit from Roche Diagnostics®(Mannheim, Germany) according to manufacturer's instructions. Plasma fructosamine levels were significantly reduced after 4 and 3 weeks of treatment respectively in the 0.15 mg/kg and 1.5 mg/kg AB-L1-FGF21ΔH-A129C treatment groups and after 3 weeks in the FGF21 control protein treated animals (FIG. 9D). This significance was sustained into the washout period particularly in the 1.5 mg/kg AB-L1-FGF21ΔH-A129C treatment group but was not consistent across the timepoints for FGF21ΔH treated animals. Significant reduction in plasma fructosamine levels over time indicates improved glycemic control.

Example 57

Fasted Plasma Glucagon

Figure 9E:
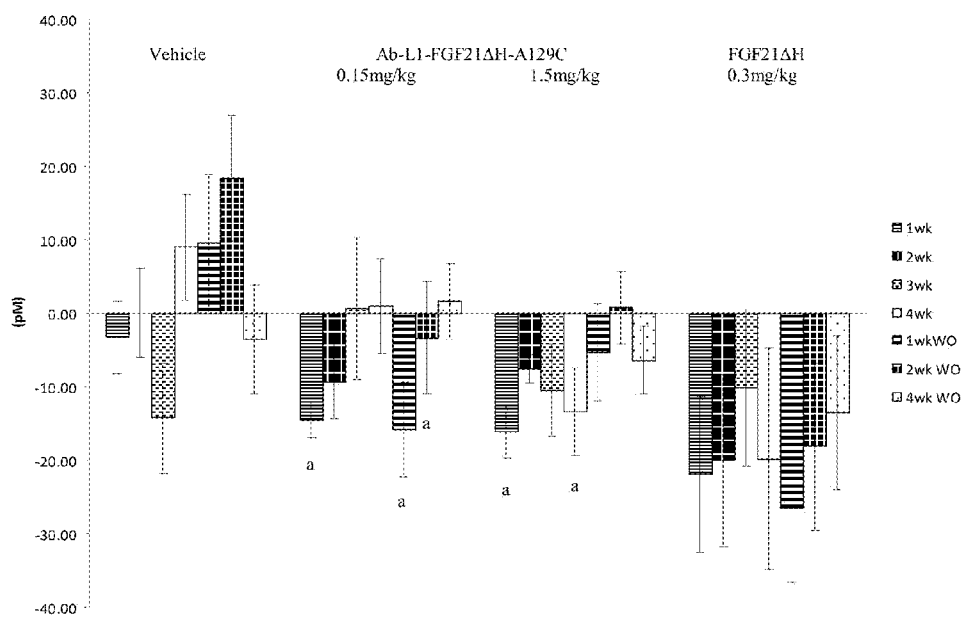

Plasma Glucagon was measured using a Human (cross-reacts with non human primate) endocrine Immunoassay kit from Millipore® on the BioPlex® Instrument (Luminex xMAP technology) according to manufacturer's instructions. Glucagon levels decreased in all 3 treatment groups with significance being reached at some timepoints throughout the study but the significance of decrease is not consistent across the treatment groups or across the AB-L1-FGF21ΔH-A129C dose groups (FIG. 9E).

Example 58

Intravenous Glucose Tolerance Test (IVGTT)

Intravenous glucose tolerance tests (IVGTTs) were conducted on each animal at three timepoints: baseline (i.e. two weeks prior to commencement of dosing), again after 4 weeks of dosing, and finally after 4 weeks of post-dosing washout. At those time points, monkeys were sedated and fasted blood samples were collected as described above. 50% dextrose (500 mg/kg; 1 mL/kg) was infused into a peripheral vein (cephalic or saphenous) over approximately 30 seconds, followed by a saline flush. Blood samples were subsequently collected into EDTA-treated vacutainers (2 mL) at 5, 10, 20, and 60 mins post-dextrose.

Glucose and insulin were measured at each of the IVGTT timepoints. Areas under the glucose and insulin curves were calculated during the glucose tolerance test (0-60 min). ΔAUC's were calculated for glucose and insulin from the glucose and insulin excursion curves by trapezoidal rule using time 0 (t=0 min) values as baseline. For the AB-L1-FGF21ΔH-A129C 0.15 mg/kg and 1.5 mg/kg treated groups statistical significance was assessed vs. vehicle by ANOVA with Dunnetts post test. Significance across the IVGTT timepoints vs. baseline was assessed for the FGF21ΔH group by repeated measure ANOVA with Dunnett's post test.

Figure 9F:
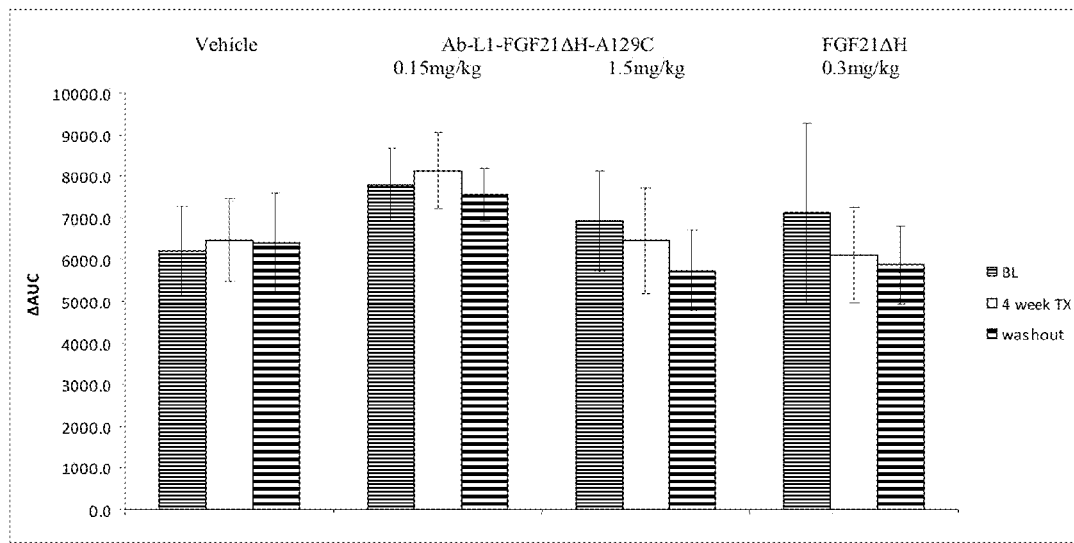
FIG. 9F. Effect of AB-L1-FGF21ΔH-A129C on intravenous glucose tolerance test (IVGTT) ΔAUC glucose. Values represent mean ΔAUC±SEM. For the AB-L1-FGF21ΔH-A129C 0.15 mg/kg and 1.5 mg/kg treated groups statistical significance was assessed vs. vehicle by one way analysis of variance (ANOVA) with Dunnetts post test. Significance across the IVGTT timepoints vs. baseline was assessed for the FGF21 control protein group by repeated measure ANOVA with Dunnetts post test.
Figure 9G:
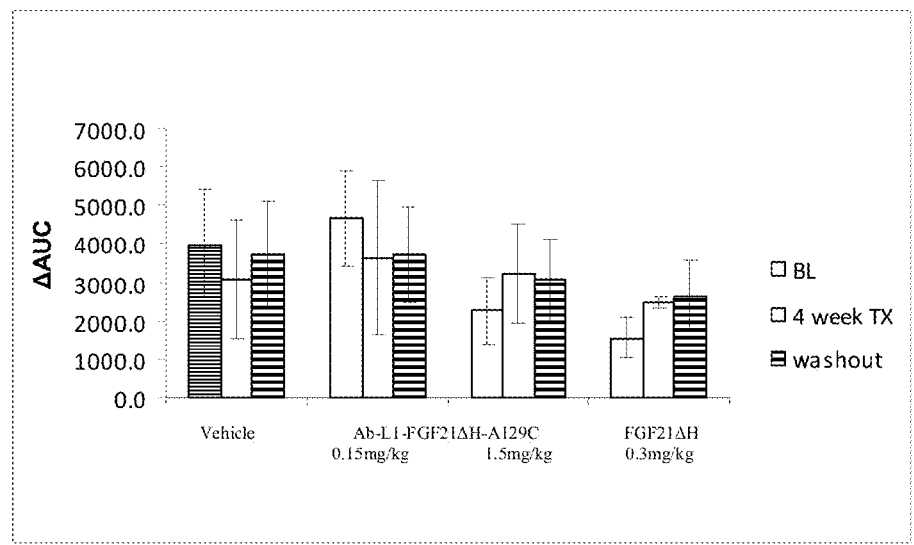
FIG. 9G. Effect of AB-L1-FGF21ΔH-A129C on IVGTT ΔAUC insulin. Values represent mean ΔAUC±SEM. For the AB-L1-FGF21ΔH-A129C 0.15 mg/kg and 1.5 mg/kg treated groups statistical significance was assessed vs. vehicle by one way ANOVA with Dunnetts post test. Significance across the IVGTT timepoints vs. baseline was assessed for the FGF21 control protein group by repeated measure ANOVA with Dunnetts post test FIG. 9H. Effect of AB-L1-FGF21ΔH-A129C on fasted total plasma cholesterol.

Mean calculated ΔAUCs±SEM for glucose and insulin are shown in FIGS. 9F and 9G respectively. There were no significant changes in any of the calculated parameters for any of the treatment groups.

Example 59

Total Plasma Cholesterol (TPC)

Figure 9H:
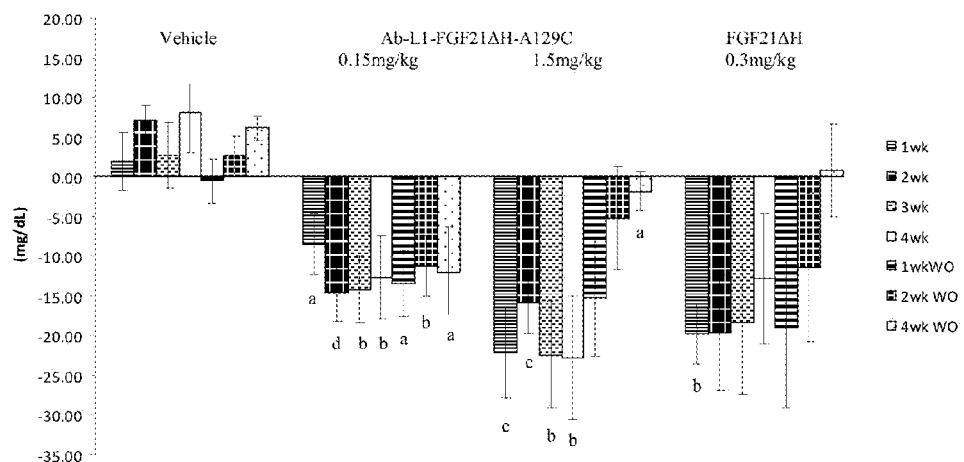

TPC levels were measured using enzymatic methods on the Ace Alera analyzer. There was a significant decrease in TPC after 1 week of treatment in all treatment groups (FIG. 9H). In the 0.15 mg/kg AB-L1-FGF21ΔH-A129C treated animals TPC levels remained decreased through the entire dosing and washout phase whereas in the 1.5 mg/kg and FGF21ΔH treated groups levels rebounded towards baseline during the washout phase.

Example 60

Triglycerides (TG)

Figure 9I:
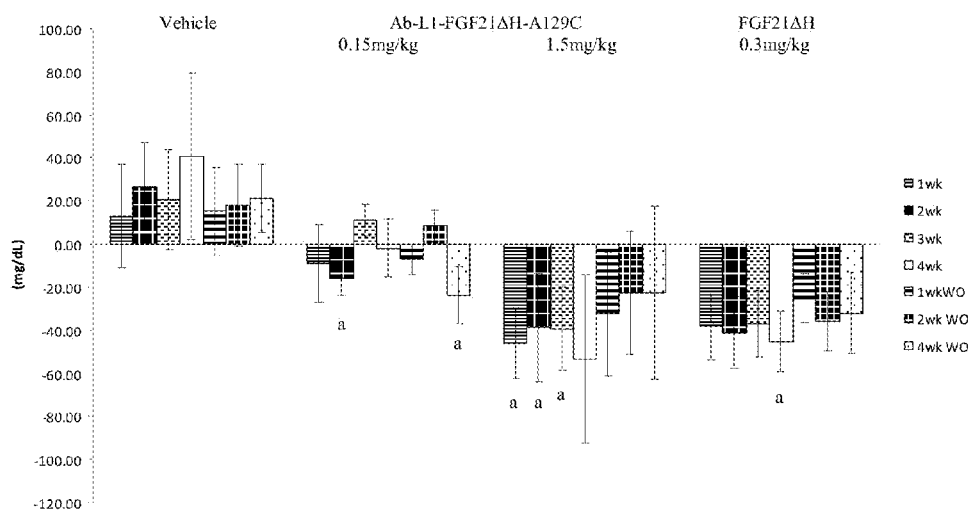

TG levels were measured using enzymatic methods on the Ace Alera analyzer. There was a significant decrease in TG over the dosing period in both the 1.5 mg/kg AB-L1-FGF21ΔH-A129C treated group and the FGF21ΔH treated animals (FIG. 9i). The reduction in TG levels persisted across the washout phase in the FGF21ΔH treated group whereas TG levels in the 1.5 mg/kg AB-L1-FGF21ΔH-A129C treated group trended towards baseline in the washout phase.

Example 61

Non-Esterified Free Fatty Acids (FFA)

Non-esterified free fatty acids (FFA) were measured using enzymatic methods on a Roche Cobas® C311 clinical chemistry analyzer using protocols and reagents from Wako® (Wako Diagnostics, Richmond, Va.) according to manufacturer's instructions. There was no significant change in FFA levels in the 0.15 mg/kg and 1.5 mg/kg AB-L1-FGF21ΔH-A129C treated groups (FIG. 9J). FFA levels in the FGF21ΔH treated animals were significantly increased over the first 2 weeks of treatment and then returned to baseline levels by week 1 of the washout phase.

Example 62

High Density Lipoprotein Cholesterol (HDL)

HDL levels were measured using enzymatic methods on the Ace Alera analyzer. There was no significant change in HDL cholesterol over the treatment period in any of the treatment groups.

Example 63

Low Density Lipoprotein Cholesterol (LDL)

Figure 9K:
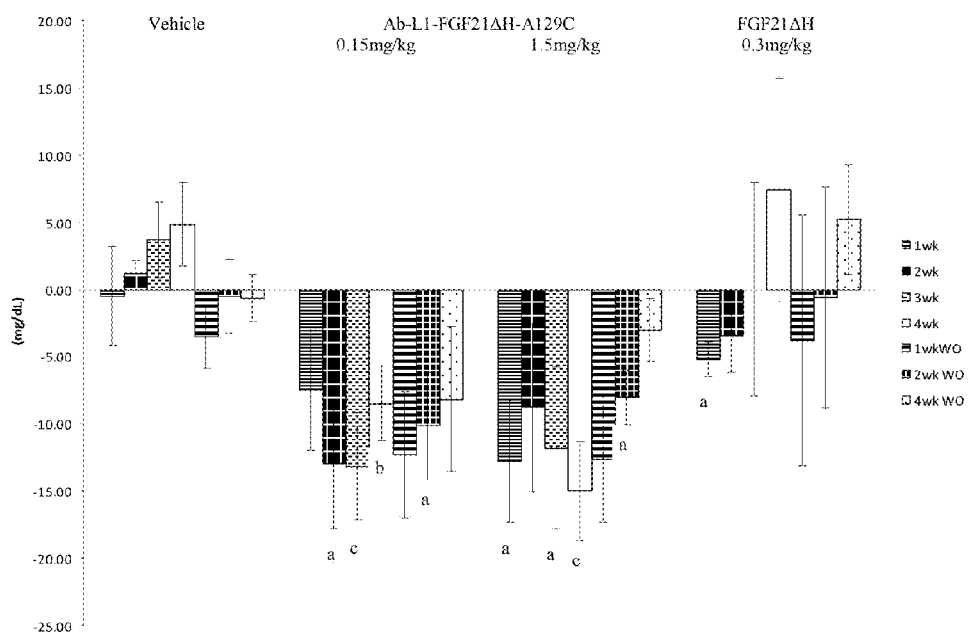

LDL levels were measured using enzymatic methods on the Ace Alera analyzer. There was a significant decrease in LDL cholesterol from 2 weeks and 1 week of treatment respectively through to week 2 of the washout period in the 0.15 mg/kg and 1.5 mg/kg AB-L1-FGF21ΔH-A129C treated groups (FIG. 9K). A significant decrease in LDL cholesterol levels was only observed after 1 week of treatment in FGF21ΔH treated animals. No significance was seen at any other timepoint in this treatment group.

Example 64

Total Ketone Bodies (TOTK)

Figure 9L:
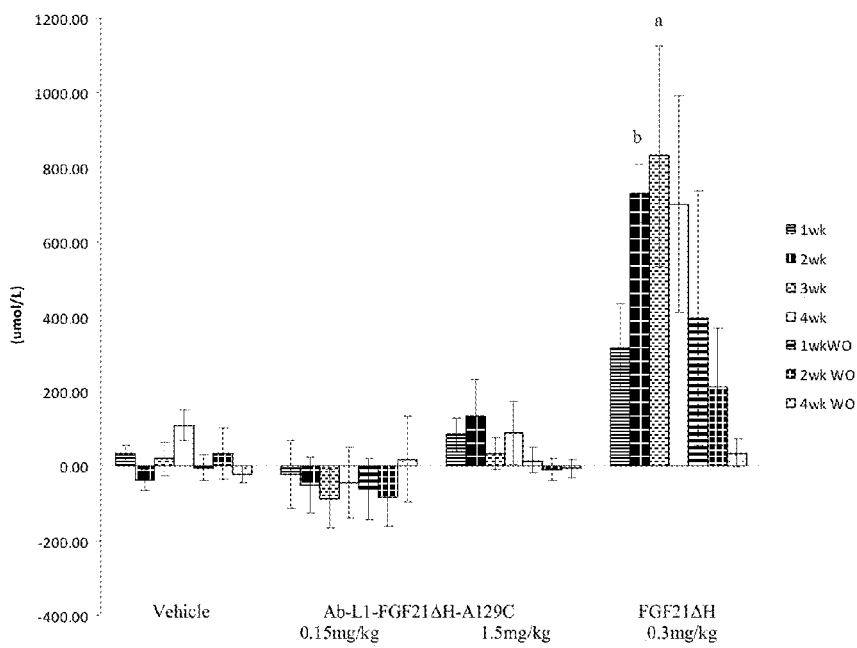

TOTK were measured using enzymatic methods on a Roche Cobas® C311 clinical chemistry analyzer using protocols and reagents from Wako®. There was no significant change in total ketone body levels in the 0.15 mg/kg and 1.5 mg/kg AB-L1-FGF21ΔH-A129C treated animals (FIG. 9L). TOTK levels were significantly increased in the FGF21ΔH treated animals over the first 3 weeks of treatment with levels trending towards baseline over the washout period.

Example 65

Adiponectin

Figure 9M:
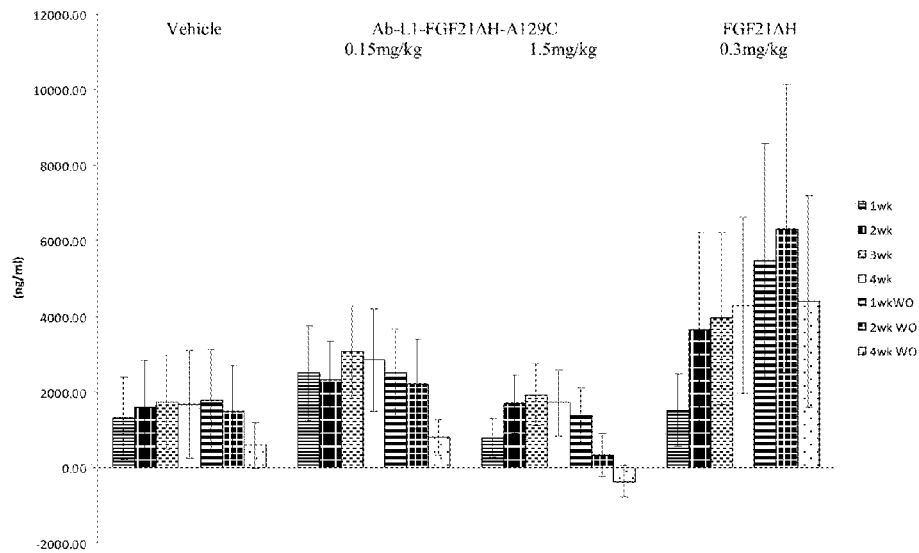

Adiponectin levels were determined using a Mercodia® ELISA kit. Plasma adiponectin levels are shown in FIG. 9M. Three animals (one each in the vehicle, 1.5 mg/kg AB-L1-FGF21ΔH-A129C and the FGF21ΔH treated group) were excluded from analysis as their adiponectin levels were below the limit of detection for the assay. No significant change in adiponectin levels were seen in any of the treatment groups although the levels trended upwards in the FGF21ΔH treated animals.

Example 66

C-Reactive Protein (CRP)

Figure 9N:
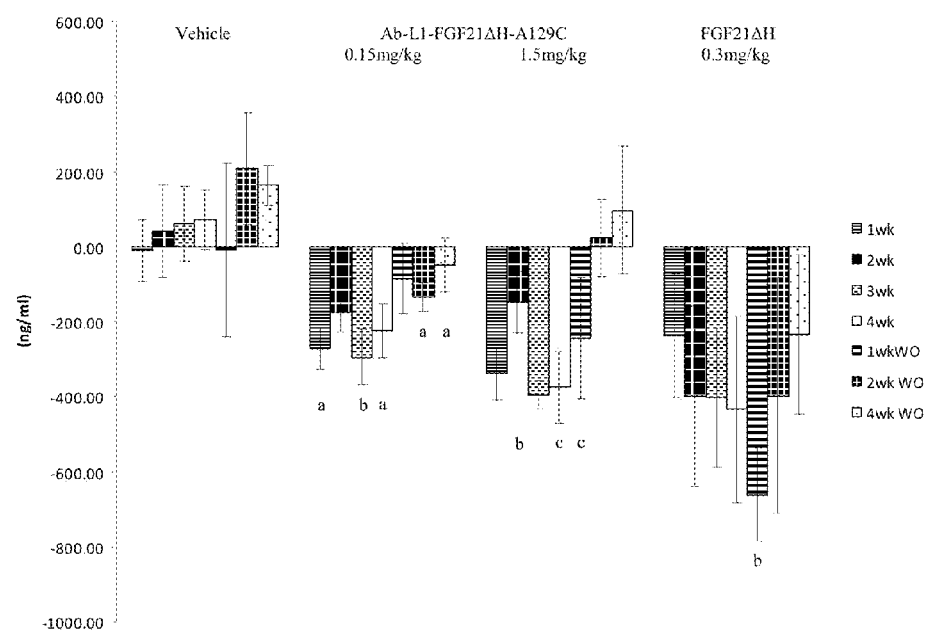

C-reactive protein (CRP) was measured using an ELISA kit from ALPCO Diagnostics® (Salem, N.H.) according to manufacturer's instructions. Plasma CRP levels were significantly decreased in the 0.15 and 1.5 mg/kg AB-L1-FGF21ΔH-A129C treated animals over the 4 week treatment period with the exception of week 2 (FIG. 9N). Levels trended back to baseline during the washout phase. Plasma CRP levels also decreased in the FGF21ΔH treated animals but significance was only reached at the 1 week washout timepoint.

Example 67

Leptin

Figure 9O:
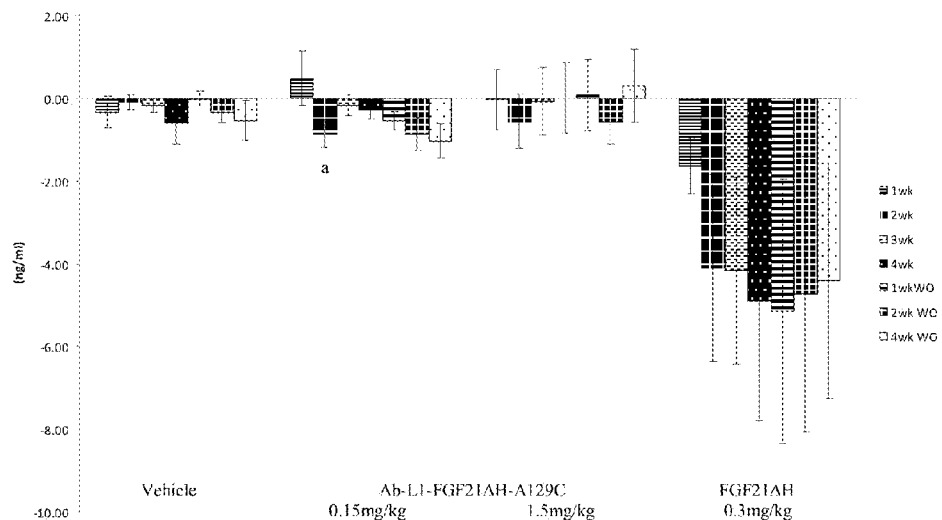
Figure 9P:
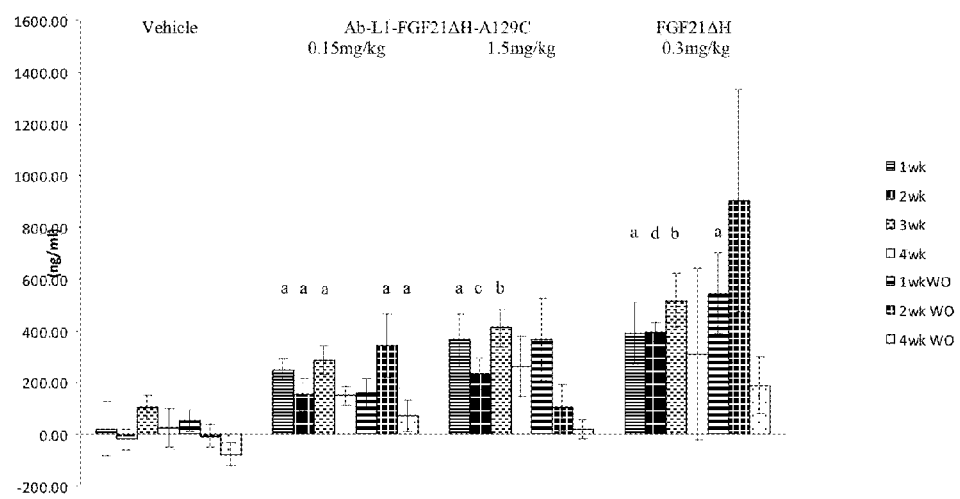

Leptin was measured by Luminex® technology (Millipore® catalogue number HMH-34K) with protocols and reagents according to manufacturer's instructions. Plasma leptin levels decreased in the FGF21ΔH treated animals (FIG. 9o) but this decrease did not reach significance at any of the timepoints. There was no change in leptin levels in the AB-L1-FGF21ΔH-A129C treated groups

Example 68

Adipsin

Adipsin levels were measured using and R&D Systems® (Minneapolis Minn.) human complement factor D Quantikine kit (catalogue number DFD00) according to manufacturer's instructions. Plasma adipsin levels increased significantly in all the treated animals (FIG. 9Q) during the first 3 weeks of treatment. The levels trended back towards baseline during the washout phase.

Example 69

Conclusion from Monkey Studies

AB-L1-FGF21ΔH-A129C was efficacious in reducing body weight, improving lipid indices (TPC, TG and LDL), and reducing an inflammatory biomarker (CRP) in mild to moderately insulin resistant cynomolgus macaques. There was no apparent effect of AB-L1-FGF21ΔH-A129C or FGF21ΔH on fasted blood glucose levels and no development of hypoglycemia. There was no effect on insulin sensitivity as assessed by an IVGTT. While unexpected, this result, along with the lack of effect on plasma glucose levels, may be due to the baseline levels of glucose and insulin in these macaques being only slightly elevated compared to normal healthy macaques. This suggests that these animals display only mild insulin resistance. The small change in baseline levels combined with the natural variability from monkey to monkey and low animal number per group may make it difficult to observe statistically significant changes in glycemic indices. The reduction in fructosamine levels in the AB-L1-FGF21ΔH-

A129C treated animals towards the end of the treatment period does indicate improved glycemic control in these animals. Twice weekly dosing of AB-L1-FGF21ΔH-A129C (particularly the 1.5 mg/kg dose) produced comparable beneficial effects to daily dosing of the control FGF21 protein.

Example 70

First in Human Study of AB-L1-FGF21ΔH-A129C

A randomized, placebo-controlled, parallel ascending single IV dose study of Ab-L1-FGF21ΔH-A129C (h38C2-(SEQ ID NO: 9-L1)$_2$) was undertaken in subjects with Type 2 diabetes mellitus. Subjects received either placebo or Ab-L1-FGF21ΔH-A129C as an IV bolus (0.5 mg and 1.5 mg) or IV infusion (5, 15, 50, 100, 200 mg) administration with 10 subjects evaluated at each active treatment dose group and 14 in the placebo group. To date, seven cohorts up to the 200 mg dose level have been evaluated without identification of the maximum tolerated dose (MTD) as single IV doses up to 200 mg were found to be generally safe and well tolerated. A preliminary summary of the observed safety/tolerability, pharmacokinetic and pharmacodynamic data is presented here.

Following a single dose administration, no difference between 7-pt mean plasma glucose profiles and fasting plasma glucose levels were observed compared with the placebo, although both test and placebo showed a decrease. No dose-related trends were observed in total cholesterol, LDL cholesterol, fasting insulin, fasting glucagon, or fasting beta-hydroxybutyrate. An increase in HDL cholesterol compared to placebo was observed at the top two dose levels studied (100 and 200 mg IV). A dose-dependent decrease in fasting triglycerides was observed.

Pharmacokinetics of intact C-terminus and intact N-terminus of FGF21 were estimated separately in healthy volunteers following single intravenous administration of Ab-L1-FGF21ΔH-A129C. Exposures to both appeared to increase proportionally with increasing dose. The terminal phases of the log concentration versus time curves were parallel with mean terminal half-lives of 7 to 9 hrs for C-terminus and 30-36 hrs for N-terminus, respectively.

There were no serious adverse events (SAEs) reported and a total of 60 adverse events (AEs) were reported in 33 subjects. Of these AEs, 54 were reported in 28 subjects while receiving Ab-L1-FGF21ΔH-A129C. The majority of AEs were deemed to be mild in intensity except an episode of nausea rated as moderate starting at 32.5 hrs post the 15 mg dose of Ab-L1-FGF21ΔH-A129C or placebo which lasted 165 hrs, did not require intervention and was considered related to study drug treatment. Also reported was an episode of diarrhea rated moderate starting at 2 hrs post the 50 mg dose of Ab-L1-FGF21ΔH-A129C or placebo and lasted for 156 hrs which did not require intervention and was considered related to study drug treatment. Diarrhea was the most frequent AE reported (14 episodes in 12 subjects) and of these, nine (9) episodes were considered-treatment related. The other episodes of diarrhea were considered related to altered chlorination treatment of tap water served to subjects in one cohort during inpatient confinement at a participating clinical research unit. Gastrointestinal symptoms (abdominal distention, abdominal pain, diarrhea, dyspepsia, flatulence, hyperchlorhydria, nausea and vomiting) appear to increase in frequency with increasing dose with five (5) subjects reporting nine (9) GI AEs in Cohort 7 (200 mg dose group or placebo). No subjects were withdrawn from participation in the study as a result of an AE.

No dose-related trends were observed in IGF-1 values, laboratory tests, vital signs or 12-lead ECGs observed across the doses studied. In the 200 mg treatment group, mean values for systolic blood pressure (SBP) trended numerically higher than other treatment groups (including placebo) with a highest increase from baseline of 11.2 mmHg at 0.5 hr post dose on Day 1 and was sustained through Day 15 at 7.0 mmHg. The mean changes from baseline observed in the 200 mg treatment group were within one standard deviation of the group mean baseline. Furthermore, there was no correlation between Ab-L1-FGF21ΔH-A129C exposure and SBP increases in individual subjects in the 200 mg treatment group. In addition, the increased SBP persisted through Day 15, well after study drug washout. All of these observations suggest that the mean increase observed is within and possibly related to treatment group variability.

Example 71

Dosage Regimen

The concentration-response relationship of triglyceride lowering following a single dose of Ab-L1-FGF21ΔH-A129C in type 2 diabetic patients was described using a slow pharmacology onset and offset PK/PD model. The PK/PD model derived IC$_{50}$ and slow pharmacology kinetics from FIH (First in Human) triglyceride data and the model derived maximal pharmacology from ob/ob mice OGTT data were used for the dose projections.

A weekly dose of 10 mg h38C2-(SEQ ID NO:9-L1)$_2$ or twice a week dose of 5 mg Ab-L1-FGF21ΔH-A129C for 4 weeks is projected to achieve ~25% fasting plasma glucose lowering in 8% HbA1C diabetic patients.

Accordingly, the present invention provides for a dosage regimen, comprising treating a patient with a dose of about 5 mg of a compound of the invention (in particular Ab-L1-FGF21ΔH-A129C). In some aspects, the about 5 mg of a compound of the invention (in particular Ab-L1-FGF21ΔH-A129C) is administered twice per week. In some aspects, the about 5 mg of a compound of the invention (in particular Ab-L1-FGF21ΔH-A129C) is administered for at least 4 weeks. In some aspect, the about 5 mg of a compound of the invention (in particular Ab-L1-FGF21ΔH-A129C) is administered twice per week, for at least 4 weeks.

Accordingly, the present invention provides for a dosage regimen, comprising treating a patient with a dose of about 10 mg of a compound of the invention (in particular Ab-L1-FGF21ΔH-A129C). In some aspects, the about 10 mg of a compound of the invention (in particular Ab-L1-FGF21ΔH-A129C) is administered once-weekly. In some aspects, the about 10 mg of a compound of the invention (in particular Ab-L1-FGF21ΔH-A129C) is administered for at least 4 weeks. In some aspect, the 10 mg of a compound of the invention (in particular Ab-L1-FGF21ΔH-A129C) is administered once-weekly for at least 4 weeks.

In some aspects, the patient suffers from type 2 diabetes. In some aspects, the patient is a diabetic patient with elevated hemoglobin A1C (HbA1C). In some aspects, the dosage regimen is for the lowering of triglyceride levels. In some aspects, the dosage regimen is for the raising of HDL. In some aspects, the dosage regimen is for the lowering of blood glucose. In some aspects, the dosage regiment is for the lowering of blood glucose by at least about 25%. In some aspects, the dosage regimen is for the treatment of type 2 diabetes.

Example 72

Stability of Ab-L1-FGF21ΔH-H125C & Ab-L1-FGF21ΔH-A129C

Various formulations of Ab-L1-FGF21ΔH-H125C & Ab (h38C2-(FGF21ΔH-H125C-L1)$_2$) and Ab-L1-FGF21ΔH-A129C (h38C2-(FGF21ΔH-A129C-L1)$_2$) were prepared by UF-DF (diafiltration and ultrafiltration using 30000 molecular weight cut-off), and then sterile filtered. The formulations were subjected to a range of stress conditions (see Table 17). The samples were then analyzed using Appearance assay, UV (ultraviolet absorbance), SDS-PAGE (sodium dodecyl sulfate-polyacrylamide gel electrophoresis), Size Exclusion Chromatography (SEC), and iCE (imaged capillary electrophoresis). Some samples were analyzed by biophysical techniques such as differential scanning calorimetry (DSC), and analytical ultracentrifugation. Samples were analyzed at various time points (Table 17) to assess stability trend. To determine any beneficial effect of polysorbate 80, selected formulations prepared with or without polysorbate 80 were subjected to agitation stress (4 hrs at 300 rpm orbital shaking). Additionally, some formulations also used higher concentration to evaluate if the conjugates are soluble in aqueous buffered solvents at high concentration and to assess stability at high concentration.

TABLE 17

Formulations of Ab-L1-FGF21ΔH-H125C (A-E) and Ab-L1-FGF21ΔH-A129C (F-I).

| | Formulation | Protein mg/mL | Initial | 4 hrs 300 rpm | 4 wks 5° C. | 4 wks 25° C. | 2 wks 40° C. | 2 wks 50° C. |
|---|---|---|---|---|---|---|---|---|
| A | "H125C-His6" (20 mM histidine, pH 6) | 7-10 | C | PF | PF | PF | PF | PF |
| B | "H125C -NaAc4" (20 mM sodium acetate, pH 4) | 7-10 | C | nc | PF | nc | C | nc |
| C | "H125C -NaP8" (20 mM sodium phosphate, pH 8) | 7-10 | C | nc | PF | nc | C | nc |
| D | "H125C -His6-50" (20 mM histidine, pH 6) | 40-50 | C | nc | PF | nc | C | nc |
| E | "H125C-His6-PS80" (20 mM his, 0.2 mg/mL polysorbate 80, pH 6) | 7-10 | C | C | nc | nc | nc | nc |
| F | "A129C-His6" (20 mM histidine, pH 6) | 7-10 | C | PF | PF | PF | PF | PF |
| G | "A129C -NaAc4" (20 mM sodium acetate, pH 4) | 7-10 | C | nc | C | nc | C | nc |
| H | "A129C -NaP8" (20 mM sodium phosphate, pH 8) | 7-10 | C | nc | C | nc | C | nc |
| I | "A129C -His6-50" (20 mM histidine, pH 6) | 40-50 | C | nc | PF | nc | C | nc |
| J | "A129C-His6-PS80" (20 mM his, 0.2 mg/mL polysorbate 80, pH 6) | 7-10 | C | C | nc | nc | nc | nc |

PF: particles formed; C: clear; nc: not conducted.

Appearance Assay

Particulate formation upon storage at various temperatures: Both candidates in 20 mM histidine, pH 6 formulation (Formulations A and F) showed particulate formation following either 4 week storage at 5° C. or 4 week at 25° C., or 2 week at 40° C., or 2 week at 50° C. These data suggest that 20 mM histidine, pH 6 formulation leads to instability of Ab-L1-FGF21ΔH-H125C and Ab-L1-FGF21ΔH-A129C. When stressed at 40° C. for 2 weeks, acetate pH 4, and phosphate pH8 showed no particulate formation, in contrast to histidine pH 6 formulation at the same protein concentration level. However, high protein concentration (40-50 mg/mL) appears to slow down particulate formation when compared to the same formulation (histidine, pH 6) at lower protein concentration (7-10 mg/mL). When appearance data of Ab-L1-FGF21ΔH-H125C and Ab-L1-FGF21ΔH-A129C after storage at 5° C. for 4 weeks are compared, Ab-L1-FGF21ΔH-A129C shows superior performance against particulate formulation in 2 formulations (acetate, pH4, and phosphate pH 8).

The presence of polysorbate 80 helps in preventing agitation stress induced particulate formation in both candidates as seen in Table 17 when comparing formulations with and without polysorbate 80. Agitation stress is commonly used for predicting stability against various process steps that involve air-water interface as well mechanical stress.

No significant change in UV was observed over time indicating that even if particulate formation was observed in some of the formulations listed in Table 17, the net concentration of protein in was not significantly affected over time.

High Molecular Weight Species (HMWS) Formation

SEC was used to measure HMWS formation for various formulations listed in Table 17 (results shown in Table 18). SEC is able to reliably separate HMWS, and is an important stability-indicating assay for both Ab-L1-FGF21ΔH-H125C and Ab-L1-FGF21ΔH-A129C. HMWS in the SEC assay is defined as the species that elute prior to the conjugates carrying 2 units of FGF21 (i.e. h38C2-(FGF21ΔH-H125C-L1)$_2$ and h38C2-(FGF21ΔH-A129C-L1)$_2$). Formulations in 20 mM histidine, pH 6 for both candidates showed high initial as well as time-dependent formation of HMWS. Interestingly, some of the formulations (acetate, pH4; phosphate, pH 8, and high concentration formulations in histidine pH 6) of both candidates at high temperatures (40° C.) tend to show an initial dissociation of aggregates in the first week. Nonlinear aggregation trend of protein formulations over time is known in literature. Formulations in 20 mM sodium acetate, pH 4 showed less HMWS when compared to formulations in 20 mM histidine, pH 6. Therefore, formulations in 20 mM sodium acetate, pH 4 provide superior stability than in 20 mM histidine, pH 6 for HMWS formation. SDS PAGE analysis was consistent with these results. Finally, when the two candidates are compared for propensity of HMWS formation at 5° C. in acetate, pH 4 formulation, Ab-L1-FGF21ΔH-A129C appears to perform superior than Ab-L1-FGF21ΔH-H125C (Table 18).

TABLE 18

Stability data of Ab-L1-FGF21ΔH-H125C and Ab-L1-FGF21ΔH-A129C %

| | Storage Temperature | | | | | | | | | |
|---|---|---|---|---|---|---|---|---|---|---|
| | 5° C. | | | 25° C. | | | | 40° C. | | |
| | Time Point (week) | | | | | | | | | |
| | initial | 2 wk | 4 wk | 8 wk | 1 wk | 2 wk | 4 wk | 1 wk | 2 wk | 4 wk |
| H125C-His6 | 25.1 | 25.9 | 27.1 | 21.8 | 22.8 | 23.3 | 22.0 | 14.5 | 20.2 | 25.1 |
| H125C-NaAc4 | 11.7 | 8.5 | 9.6 | | | | | 4.6 | 4.5 | 6.3 |
| H125C-NaP8 | 21.0 | 20.2 | 21.7 | | | | | 15.0 | 12.0 | 10.1 |
| H125C-His6-50 | 33.2 | | 36.4 | | | | | | 33.9 | 20.9 |
| A129C-His6 | 27.3 | 23.3 | 25.0 | 24.3 | 18.6 | 20.3 | 18.9 | 14.0 | 23.2 | 13.0 |
| A129C-NaAc4 | 3.6 | 3.2 | 3.5 | | | | | 2.9 | 3.6 | 5.0 |
| A129C-NaP8 | 17.8 | 17.0 | 17.8 | | | | | 11.9 | 14.9 | 30.8 |
| A129C-His6-50 | 28.2 | | 35.3 | | | | | | 29.6 | 23.5 |

HMWS (high molecular weight species) measured by SEC. SEC conditions include: Waters Biosuite UHR 250 4 μm, 4.6×300 mm SEC column, Mobile Phase: 200 mM Sodium Phosphate 100 mM Sodium Chloride buffer (pH 7.0), Column Temperature: Ambient, Flow Rate: 0.1 ml/min (Isocratic), Detection: UV absorbance at 214 nm, Run Time: 50 mins Charge Heterogeneity Proteins possess charge heterogeneity caused by post-translational modifications such as deamidation and fragmentation. Imaged capillary isoelectric focusing (iCE) separates protein species based on their charge differences (pI value) in a pH gradient. iCE was used in monitor charge heterogeneity in various formulations of Ab-L1-FGF21ΔH-H125C and Ab-L1-FGF21ΔH-A1290, shown in Table 19. Running conditions for iCE include: approximately 1 mg/mL protein with 2M urea, and Pharmalyte 3-10. Formulations in 20 mM histidine, pH 6 as well as 20 mM sodium phosphate, pH 8 for both candidates showed a higher trend of acidic species formation compared to those in 20 mM sodium acetate, pH 4. Therefore, formulations in 20 mM sodium acetate, pH 4 provide superior stability. Additionally, Ab-L1-FGF21ΔH-A129C showed a trend of lesser acidic species formation in 20 mM sodium acetate, pH 4 than Ab-L1-FGF21ΔH-H125C in the same formulation, therefore demonstrating superior stability for charge heterogeneity.

TABLE 19

% Acidic species measured by iCE Charge Heterogeneity data of Ab-L1-FGF21ΔH-H125C and Ab-L1-FGF21ΔH-A129C

| | Storage Temperature | | | | | | | |
|---|---|---|---|---|---|---|---|---|
| | 5° C. | | | 25° C. | | | 40° C. | |
| | Time Point (week) | | | | | | | |
| | initial | 2 wk | 4 wk | 1 wk | 2 wk | 4 wk | 1 wk | 2 wk |
| H125C-His6 | 60.0 | 62.8 | 64.9 | 60.3 | 71.9 | 74.2 | 75.1 | 82.9 |
| H125C-NaAc4 | 62.4 | 61.7 | 60.7 | | | | 53.3 | |
| H125C-NaP8 | 77.4 | 92.3 | 95.3 | | | | 96.2 | |
| H125C-His6-50 | 61.9 | | 78.5 | | | | | |
| A129C-His6 | 58.4 | 62.7 | 62.5 | 64.2 | 73.0 | 75.2 | 75.7 | 81.9 |
| A129C-NaAc4 | 49.3 | 52.7 | 48.8 | | | | 45.2 | |
| A129C-NaP8 | 68.3 | 87.5 | 89.0 | | | | 97.4 | |
| A129C-His6-50 | 62.5 | | 53.9 | | | | | |

Differential Scanning Calorimetry (DSC)

Thermal stability of the two candidates was investigated using DSC by measuring midpoint of transition (Tm) of temperature-induced unfolding. The Tm value of the major unfolding transition for h38C2 was 73.5° C. The conjugates showed higher Tm of the major unfolding transition, suggesting higher thermal stability against unfolding (Tm of both Ab-L1-FGF21ΔH-H125C (h38C2-(FGF21ΔH-A129C-L1)$_2$) and Ab-L1-FGF21ΔH-A129C (h38C2-(FGF21ΔH-H125C-L1)$_2$) was 79° C.).

Thermal stability of the two candidates was also investigated using intrinsic protein tryptophan fluorescence by measuring midpoint of transition (Tm-FL) of temperature-induced unfolding. This assay monitors changes in tertiary structure semi-quantitatively upon unfolding induced by high temperature. The Tm-FL values of the major unfolding transition were approximately 74.1° C., 77.7° C., and 79.7° C. for h38C2, Ab-L1-FGF21ΔH-A129C, and Ab-L1-FGF21ΔH-H125C, respectively. Consistent with the Tm values measured by DSC, the two candidates show similar Tm-FL that are slightly higher than Tm-FL of h38C2, suggesting higher thermodynamic stability of the conjugates than h38C2 alone.

Analytical Ultracentrifugation Assay

This assay was used as an orthogonal measurement of qualitative amount of HMWS in selected formulations tested. It shows a level of HMWS in 20 mM histidine, pH 6 formulations similar to those seen in SEC. It also shows lower level of HMWS in 20 mM sodium acetate, pH 4 for Ab-L1-FGF21ΔH-A129C, qualitatively consistent with trend seen in SEC assay. Analytical ultracentrifugation data provides orthogonal verification that 20 mM sodium acetate, pH 4 formulation provides superior stabilization compared to 20 mM histidine, pH6 formulation (Table 20).

TABLE 20

HMWS data measured by analytical ultracentrifugation of Ab-L1-FGF21ΔH-H125C and Ab-L1-FGF21ΔH-A129C

| Formulation | % HMWS |
|---|---|
| Ab-L1-FGF21ΔH-H125C in 20 mM histidine, pH 6 | 25.2 |
| Ab-L1-FGF21ΔH-A129C in 20 mM histidine, pH 6 | 24.3 |
| Ab-L1-FGF21ΔH-A129C in 20 mM sodium acetate, pH 4 | 5.2 |

Comparing data of several stability indicators discussed in this example, the overall stability profile of Ab-L1-FGF21ΔH-A129C appears to be superior than Ab-L1-FGF21ΔH-H125C. It is also evident that lowering pH of formulation (e.g. acetate, pH 4) provides better stability compared to higher pH (e.g. pH 6-8).

Example 73 pH-Buffer Screen of Ab-L1-FGF21ΔH-A129C

The stability of Ab-L1-FGF21ΔH-A129C (h38C2-(FGF21ΔH-A129C-L1)$_2$) in various aqueous buffers was investigated with the goal of finding an appropriate stabilizing medium. Instability of Linker-1, as well as any hydrolytic clipping of the protein components (i.e. h38C2 and FG21) results in the generation of low molecular weight species (LMWS). Additionally, high molecular weight species can be formed if the conjugates aggregate in the formulation tested. Formulations were prepared by buffer exchange into the desired formulation with a target protein concentration in the range of 5-8 mg/mL. Formulations were filtered using 0.2 um filter, packaged in glass vials and stored at desired temperature. At indicated time points, samples were assayed.

HMWS and LMWS Measurement by SEC

Pronounced effect of buffer and pH was observed upon temperature stress (40° C.) for 2 weeks. The data is presented in Table 21. At initial time point, a trend of increasing HMWS was seen at higher pH formulations. Histidine formulations were among the ones showing high % HMWS. Sodium acetate, sodium lactate, sodium malate, and sodium citrate formulations in the pH range 4.5 to 5 showed relatively less aggregate at initial point. Upon storage at 40° C. for weeks, % HMWS actually decreased in formulations at pH 6.5 and 7. Sodium lactate, pH 4.5 formulation showed relatively superior performance for % HMWS.

The LMWS trend was different from that of HMWS. Except sodium citrate, pH 5 formulation, all formulations showed consistent values of % LMWS at initial time point. Upon storage at 40° C. for 2 weeks, some of the low pH formulations showed pronounced increase in % LMWS presumably due to fragmentation. However, it is apparent that effects of buffer species also play a role in stabilizing against LMWS formation. The trend of pH-dependent % LMWS suggests further refinement in formulation could achieve a further improvement in stability.

TABLE 21

SEC data of formulations of Ab-L1-FGF21ΔH-A129C

| ID | Formulation | % HMWS at initial | % HMWS after 2 weeks at 40° C. | % LMWS at initial | % LMWS after 2 weeks at 40° C. |
|---|---|---|---|---|---|
| A | 20 mM Sodium Acetate, pH 4.5 | 8.9 | 13.7 | 26.8 | 38.1 |
| B | 20 mM Sodium Acetate, pH 5 | 9.4 | 22.6 | 26.1 | 33.8 |
| C | 20 mM Sodium Acetate, pH 5.5 | 12.1 | 29.2 | 26.1 | 33.2 |
| D | 20 mM Histidine, pH 5.5 | 16.9 | 26.0 | 25.3 | 29.7 |
| E | 20 mM Histidine, pH 6 | 23.0 | 28.2 | 24.6 | 29.7 |
| F | 20 mM Histidine, pH 6.5 | 18.0 | 14.8 | 25.5 | 38.6 |
| G | 20 mM Sodium Lactate, pH 4.5 | 8.9 | 11.3 | 26.7 | 55.2 |
| H | 13 mM Sodium Malate, pH 4.5 | 9.2 | 20.8 | 27.6 | 52.7 |
| I | 13 mM Sodium Malate, pH 5 | 9.9 | 34.3 | 27.6 | 28.3 |
| J | 10 mM Sodium Citrate, pH 5 | 7.8 | 24.3 | 36.5 | 47.5 |
| K | 10 mM Sodium Citrate, pH 6.5 | 21.5 | 15.9 | 26.0 | 37.8 |
| L | 13 mM Sodium Succinate, pH 6 | 16.8 | 13.3 | 26.2 | 42.1 |
| N | 10 mM Sodium Phosphate, pH 6.5 | 22.2 | 12.9 | 25.3 | 45.3 |
| P | 10 mM Sodium Phosphate, 100 mM NaCl, pH 6.5 | 19.3 | 15.4 | 25.7 | 40.0 |
| Q | 10 mM Sodium Phosphate, pH 7 | 16.4 | 13.1 | 27.1 | 43.9 |
| R | 7 mM Sodium acetate, 7 mM Histidine, 4 mM Sodium malate, pH 5 | 9.9 | 22.6 | 27.0 | 33.7 |
| S | 5 mM Sodium citrate, 5 mM Sodium Phosphate, pH 6.5 | 22.1 | 12.1 | 25.9 | 44.7 |

Example 74

Stability of Ab-L1-FGF21ΔH-A129C Against Agitation

Formulations were prepared by buffer exchange and excipient addition with a target protein concentration in the range of 9-11 mg/mL. The prepared formulations were filtered using 0.2 um filter, packaged in glass vials. Agitation was applied using an orbital shaker at 300 rpm speed. At indicated time points, samples were assayed. Results in Table 22 demonstrate that the presence of polysorbate 80 helps prevent agitation-induced instability.

TABLE 22

Stability data of formulations against agitation stress

| Formulation | Appearance at initial | Appearance after 24 hr agitation | Change in % HMWS after 24 hr agitation |
|---|---|---|---|
| 30 mM Sodium Lactate, 90 mg/mL trehalose dihydrate, pH 4.8 | Clear | Milky liquid and precipitation | 1.4 |

TABLE 22-continued

Stability data of formulations against agitation stress

| Formulation | Appearance at initial | Appearance after 24 hr agitation | Change in % HMWS after 24 hr agitation |
|---|---|---|---|
| 30 mM Sodium Lactate, 90 mg/mL trehalose dihydrate, 0.5 mg/mL polysorbate 80, pH 4.8 | Clear | Clear with few particulates | 0.1 |

Example 75

Lyophilized Formulations of Ab-L1-FGF21ΔH-A129C

Although liquid formulations can be used with compounds of the invention, lyophilized formulations can provide greater longevity of stability. Example 72 demonstrated the surprising result that compounds of the invention were most stable in sodium acetate. However, sodium acetate sublimes, and accordingly is difficult to incorporate into a lyophilized buffer. There therefore exists a need to develop an alternative buffer for compounds of the invention that provides optimum long term stability in a lyophilized formulation.

Formulations were prepared by buffer exchange and excipient addition with a target protein concentration of approximately 10 mg/mL except formulations J and K that target approximately 20 mg/mL. The prepared formulations were filtered using 0.2 um filter, and packaged in glass vials. To prepare lyophilized formulations, the vials were lyophilized, stoppered and capped. At indicated time points, samples were pulled and assayed by various analytical methods including SEC, and iCE. The liquid formulations were also evaluated for 2 weeks to evaluate stability.

The performance of the lyophilized formulations upon storage at elevated temperature was assessed. Table 23 shows SEC and iCE data at indicated time points. The lyophilized formulations performed superior even when compared to higher temperature stress. Among the lyophilized formulations, lactate and acetate formulations performed relatively better. However, acetate is known to undergo sublimation when lyophilized causing pH drift. Indeed the acetate formulations showed an increase of 0.3-0.5 pH unit upon lyophilization. Therefore, it is concluded that lyophilized lactate formulation (formulation C) is appropriate to achieve adequate stability, and provides sufficient protection from formation of particulates, HMWS, LMWS, and acidic species. When comparing with formulations presented in example 73, it is clear that formulation C (comprised of lactate, trehalose dihydrate, PS20, EDTA, L-Met) helps in prevention of linker instability and protein clipping (both of which give rise to LMWS formation), as well aggregation (formation of particulates and HMWS). Examples 72 and 73 show that formulations of h38C2-(FGF21ΔH-A129C-L1)$_2$ with only lactate, albeit superior to other buffers such as histidine, may not provide adequate stability for desired longer term use. The combination of lactate with various types of stabilizers such as a sugar or polyol serving as cryoprotectant and lyoprotectant (e.g. trehalose, sucrose, mannitol), and a surfactant for agitation stability (e.g. polysorbate 80, polysorbate 20, poloxamer), and a chelator (e.g. EDTA, DTPA), and an anti-oxidant (e.g. L-Methionine) provides synergistic enhancement of stability. The combination formulations in Table 23 where lactate is replaced by one of malate, succinate or acetate, provide superior stability when compared to the corresponding buffer-only formulations. Therefore, the combinations clearly enhance stability of Ab-L1-FGF21ΔH-A129C.

Example 76

Lyophilized Formulations of Ab-L1-FGF21ΔH-A129C

Formulations were prepared by buffer exchange and excipient addition with a target protein concentration that varied between formulations. The prepared formulations were filtered using 0.2 μm filter, and packaged in glass vials. To prepare lyophilized formulations, the vials were lyophilized, stoppered and capped. At indicated time points, samples assayed by various analytical methods including SEC, and iCE. Additionally, the liquid formulations were also evaluated for 2 weeks to evaluate stability trend of liquid formulations. Water content of the lyophilized formulations were tested after lyophilization, and were all below 0.5%.

The lyophilized formulations were stored under various temperature stress, and Table 24 shows SEC, iCE, and reduced CGE (capillary gel electrophoresis) data at indicated time points. CGE produces semi-quantitative estimate of protein fragments. The lyophilized formulations showed better stability when compared to their liquid counterparts. The lyophilized formulations of lactic acid (sodium lactate) in the presence of stabilizing excipients (in the presence of a cryoprotectant/lyoprotectant) showed good stability. Therefore, it is concluded that lyophilized lactic acid formulations are appropriate to test for longer term storage stability. Among the lactic acid formulations, a balance of pH of formulations is needed to prevent excessive fragmentation due to linker instability and protein clipping. For example, formulation F, pH 4.5, in liquid state, produces substantial fragmentation compared to other formulations. Finally, when formulations B and L are compared, stabilizers (namely, EDTA and L-Methionine) are seen to minimize fragmentations, providing a substantial benefit, especially to the liquid formulations. Other combinations of metal chelators (e.g. EDTA, DTPA) and anti-oxidants (e.g. L-Methionine, pure ascorbic acid) are expected to be beneficial to achieve stability.

Selected formulations were also tested for relative bioactivity to explore if there are correlations to physical and chemical degradations seen in the data in Table 24. Bioactivity was measured by an Indirect FGF-R/β-Klotho HEK-293 Cell Binding ELISA, and expressed as relative % to that of a reference material. Bioactivity data are presented in Table 25. From the data, it appears that physical and chemical degradations are correlated, and the formulations that show significant degradation assayed by analytical methods (Table 24) also show significant reduction in bioactivity. These data provides further confidence in stability and functional integrity provided by the components of formulation A.

TABLE 25

Bioactivity (relative %) data of selected Lyophilized and Liquid formulations of Ab-L1-FGF21ΔH-A129C listed in Table 24

| Formulation ID | Bioactivity after 2 weeks at 5° C. | Bioactivity after 2 weeks at 25° C. | Bioactivity after 2 weeks at 40° C. | Liquid/Lyophilized |
|---|---|---|---|---|
| A | 105 | — | — | Lyophilized |
| B | — | 107 | 64 | Liquid |
| D | — | 97 | 61 | Liquid |
| F | — | 98 | 49 | Liquid |

Accordingly, in some aspects the invention provides for a formulation comprising between about 0.1 and about 200 mg/ml of FGF21-conjugate and between about 1 and 150 mM lactic acid or sodium acetate, pH between about 4 and about 5.5; and at least one of the following:
(i) between about 10 to about 150 mg/ml cryoprotectant;
(ii) between about 0.001 and about 1.0 mg/ml chelator;
(iii) between about 0.01 and about 10 mg/ml anti-oxidant;
(iv) between about 0.02-2.0 mg/mL surfactant.
In some aspects, formulations of the invention comprise two or more of (i) to (iv). In some aspects formulations of the invention comprise three or more of (i) to (iv). In some aspects, formulations of the invention comprise (i), (ii), (iii), and (iv).

In some aspects the invention provides for a lyophilized formulation comprising:
(i) between about 0.1 and about 200 mg/ml of FGF21-conjugate
(ii) between about 1 and 150 mM lactic acid pH between about 4 and about 5.5; and
(iii) between about 10 to about 150 mg/ml cryoprotectant;
(iv) between about 0.02-2.0 mg/mL surfactant.

In some aspects, the lyophilized formulation may further comprise between about 0.001 and about 1.0 mg/ml chelator. The chelator may be EDTA or DTPA, and may be present in an amount of between about 0.02 to about 0.5 mg/mL. The chelator may be present in an amount of about 0.05 mg/mL.

In some aspects, the lyophilized formulation may further comprise between about 0.01 and about 10 mg/ml anti-oxidant. In some aspects, the antioxidant may be L-methionine. The antioxidant may be present in an amount of between about 0.02 and about 5 mg/mL. The antioxidant may be present in an amount of between about 0.05 and about 0.2 mg/mL. The antioxidant may be present in an amount of about 0.1 mg/mL.

In some aspects, the FGF21-conjugate is a compound of the invention as herein described. In some aspects, the FGF21-conjugate is Ab-L1-FGF21ΔH-H125C or Ab-L1-FGF21ΔH-A129C. In some aspects, the FGF21 conjugate is the specific species h38C2-(SEQ ID NO:9-L1)$_2$. In some aspects, the FGF21-conjugate is present in an amount of between about 5 mg/ml and about 200 mg/ml. In some aspects, the FGF21-conjugate is present in an amount of between about 5 mg/ml and about 100 mg/ml. the FGF21-conjugate is present in an amount of between about 5 mg/ml and about 50 mg/ml. the FGF21-conjugate is present in an amount of about 10 mg/ml.

In some aspects, the lactic acid is present in an amount of between about 1 to about 100 mM. In some aspects, the lactic acid is present in an amount of between about 10 mM and about 50 mM. In some aspects, the lactic acid is present in an amount of about 30 mM. The pH may be between about 4.3 and about 5.3. The pH may be about 4.8±0.5. The pH may be about 4.8.

In some aspects, the cryoprotectant is selected from the group consisting of trehalose dihydrate, sucrose, and mannitol. The cryoprotectant may be trehalose dihydrate. The cryoprotectant may be present in an amount of between about 50 and about 120 mg/ml. The cryoprotectant may be present in an amount of about 90 mg/ml.

In some aspects, the surfactant may be selected from the group consisting of polysorbate 80, polysorbate 20 and poloxamer. The surfactant may be polysorbate 20. In some aspects, the surfactant is present in an amount of about 0.05 to about 1.0 mg/mL. In some aspects the surfactant is present in an amount of about 0.1 to about 0.5 mg/mL. In some aspects, the surfactant is present in an amount of about 0.2 mg/mL.

In some aspects, the invention comprises a formulation suitable for lypholization comprising the following:
(i) about 10 mg/mL h38C2-(FGF21ΔH-A129C-L1)$_2$;
(ii) about 30 mM lactic acid, pH 4.8±0.5;
(iii) about 90 mg/mL trehalose dehydrate;
(iv) about 0.05 mg/mL disodium EDTA dihydrate;
(v) about 0.1 mg/mL L-methionine; and
(vi) about 0.2 mg/mL polysorbate 20.

Unless otherwise indicated, where the term "Ab-L1-FGF21ΔH-A129C" is used in the context of the specific examples, this refers to the h38C2 antibody (SEQ ID NO:25 and 26), with each arm of the antibody covalently linked through $K^{99}$ of SEQ ID NO:26 to linker-1 (L1), and each L1 molecule covalently conjugated to the thiol group of $Cys^{129}$ in SEQ ID NO:9 (according to the numbering of SEQ ID NO:1). The compound may also be described as Ab-(FGF21ΔH-A129C-L1)$_2$, h38C2 (FGF21ΔH-A129C-L1)$_2$, and h38C2-(SEQ ID NO:9-L1)$_2$. It will be apparent that minor modifications to the sequence of the antibody, specific linker and FGF21 molecule may be possible.

The invention thus has been disclosed broadly and illustrated in reference to representative embodiments described above. Those skilled in the art will recognize that various modifications can be made to the present invention without departing from the spirit and scope thereof. All publications, patent applications, and issued patents, are herein incorporated by reference to the same extent as if each individual publication, patent application or issued patent were specifically and individually indicated to be incorporated by reference in its entirety. Definitions that are contained in text incorporated by reference are excluded to the extent that they contradict definitions in this disclosure.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. In particular, any aspect of the invention described in the claims, alone or in combination with one or more additional claims and/or aspects of the description, is to be understood as being combinable with other aspects of the invention set out elsewhere in the claims and/or description.

The use of the term "or" in the claims is used to mean "and/or" unless explicitly indicated to refer to alternatives only or the alternative are mutually exclusive, although the disclosure supports a definition that refers to only alternatives and "and/or."

As used herein the specification, "a" or "an" may mean one or more, unless clearly indicated otherwise. As used herein in the claim (s), when used in conjunction with the word "comprising, "the words "a" or "an" may mean one or more than one. As used herein "another" may mean at least a second or more.

The words "comprises/comprising" and the words "having/including" when used herein with reference to the present invention are used to specify the presence of stated features, integers, steps or components but does not preclude the presence or addition of one or more other features, integers, steps, components or groups thereof.

TABLE 23

Lyophilized and Liquid formulations of Ab-L1-FGF21ΔH-A129C

| ID | Buffer | pH | Sugar | Surfactant | EDTA mg/mL | L-Met mg/mL | % HMWS at initial (liquid) | % HMWS after 2 weeks at 25° C. (Liquid) | % HMWS after 9 weeks at 25° C. (Lyophilized) | % HMWS after 4 weeks at 40° C. (Lyophilized) | % Acidic species at initial (Liquid) | % Acidic species after 4 weeks at 40° C (Lyophilized) |
|---|---|---|---|---|---|---|---|---|---|---|---|---|
| A | 30 mM Acetate | 4.5 | 90 mg/mL trehalose dihydrate | 0.5 mg/mL PS20 | 0.05 | 0.1 | 5.2 | 7.2 | 3.7 | 4.7 | 31.1 | 34.3 |
| B | 20 mM Succinate | 4.5 | 90 mg/mL trehalose dihydrate | 0.5 mg/mL PS20 | 0.05 | 0.1 | 5.9 | 25.2 | 4.0 | 4.9 | 31.8 | 40.2 |
| C | 30 mM Lactate | 4.8 | 90 mg/mL trehalose dihydrate | 0.5 mg/mL PS20 | 0.05 | 0.1 | 5.2 | 7.8 | 3.7 | 4.7 | 31.8 | 32.0 |
| D | 30 mM Malate | 4.8 | 90 mg/mL trehalose dihydrate | 0.5 mg/mL PS20 | 0.05 | 0.1 | 7.6 | 16.8 | 4.4 | 5.6 | 32.3 | 34.7 |
| E | 30 mM Malate | 4.8 | 45 mg/mL trehalose dihydrate | 0.25 mg/mL PS20 | 0.025 | 0.05 | 7.8 | 15.7 | 4.9 | 7.4 | 32.1 | 34.0 |
| F | 20 mM Succinate | 4.8 | 45 mg/mL trehalose dihydrate | 0.25 mg/mL PS20 | 0.025 | 0.05 | 6.6 | 23.5 | 4.3 | 5.7 | 31.3 | 38.2 |
| G | 30 mM Malate 50 mM NaCl | 4.8 | 60 mg/mL trehalose dihydrate | 0.25 mg/mL PS20 | 0.05 | 0.1 | 9.7 | 16.7 | 5.0 | 6.9 | 31.9 | 33.1 |
| H | 30 mM Malate | 4.8 | 90 mg/mL trehalose dihydrate | 0.4 mg/mL Poloxamer188 | 0.05 | 0.1 | 7.9 | 17.8 | 4.7 | 5.8 | 31.5 | 34.4 |
| I | 30 mM Malate 50 mM KCl | 4.8 | 60 mg/mL trehalose dihydrate, 20 mg/ml mannitol | 0.25 mg/mL PS20 | 0.025 | 0.05 | 9.5 | 15.6 | 5.1 | 6.7 | 32.9 | 34.5 |
| J 20 mg/mL | 30 mM Acetate | 4.8 | 90 mg/mL trehalose dihydrate | 0.5 mg/mL PS20 | 0.05 | 0.1 | 6.7 | 13.1 | 4.5 | 4.8 | 32.4 | 32.8 |
| K 20 mg/mL | 20 mM Succinate | 4.8 | 90 mg/mL trehalose dihydrate | 0.5 mg/mL PS20 | 0.05 | 0.1 | 8.1 | 16.7 | 5.0 | 5.8 | 32.0 | 35.9 |
| L | 30 mM Acetate | 5 | 90 mg/mL trehalose dihydrate | 0.5 mg/mL PS20 | 0.05 | 0.1 | 6.4 | 7.8 | 4.5 | 4.8 | 32.2 | 31.9 |
| M | 20 mM Succinate | 5 | 90 mg/mL trehalose dihydrate | 0.5 mg/mL PS20 | 0.05 | 0.1 | 7.1 | 19.2 | 4.6 | 4.9 | 31.4 | 36.2 |

TABLE 24

Lyophilized and Liquid formulations of Ab-L1-FGF21ΔH-A129C

| ID | protein conc mg/mL | Buffer | pH | Excipients | Liq/Lyo | % HMWS at initial | % HMWS after 2 weeks at 40° C. | % HMWS after 8 weeks at 25° C. | % HMWS after 4 weeks at 40° C. | % Acidic species at initial | % Acidic species after 4 wks at 40° C. | % Frag at initial | % Frag after 2 weeks at 40° C. |
|---|---|---|---|---|---|---|---|---|---|---|---|---|---|
| A | 10 | 30 mM Lactic Acid | 4.8 | 90 mg/mL Trehalose dihydrate, 0.05 mg/mL EDTA, 0.1 mg/mL L-Methionine, 0.5 mg/mL PS20 | Lyo | 5.5 | 5.4 | 5.5 | 5.2 | 38.1 | 40.4 | 2.1 | 2.0 |
| B | 10 | 30 mM Lactic Acid | 4.8 | 90 mg/mL Trehalose dihydrate, 0.05 mg/mL EDTA, 0.1 mg/mL L-Methionine, 0.5 mg/mL PS20 | Liq | 5.5 | 14.1 | 8.7 | — | 38.2 | — | 1.7 | 1.4 |

TABLE 24-continued

Lyophilized and Liquid formulations of Ab-L1-FGF21ΔH-A129C

| ID | protein conc mg/mL | Buffer | pH | Excipients | Liq/Lyo | % HMWS at initial | % HMWS after 2 weeks at 40° C. | % HMWS after 8 weeks at 25° C. | % HMWS after 4 weeks at 40° C. | % Acidic species at initial | % Acidic species after 4 wks at 40° C. | % Frag at initial | % Frag after 2 weeks at 40° C. |
|---|---|---|---|---|---|---|---|---|---|---|---|---|---|
| C | 10 | 30 mM Lactic Acid | 5.1 | 90 mg/mL Trehalose dihydrate, 0.05 mg/mL EDTA, 0.1 mg/mL L-Methionine, 0.5 mg/mL PS20 | Lyo | 5.8 | 5.6 | 5.9 | 5.1 | 38.5 | 40.4 | 1.7 | 2.2 |
| D | 10 | 30 mM Lactic Acid | 5.1 | 90 mg/mL Trehalose dihydrate, 0.05 mg/mL EDTA, 0.1 mg/mL L-Methionine, 0.5 mg/mL PS20 | Liq | 5.8 | 16 | 9.3 | — | 39.1 | — | 1.7 | 1.3 |
| E | 10 | 30 mM Lactic Acid | 4.5 | 90 mg/mL Trehalose dihydrate, 0.05 mg/mL EDTA, 0.1 mg/mL L-Methionine, 0.5 mg/mL PS20 | Lyo | 5.5 | 5.4 | 5.3 | 5.1 | 38.9 | 40.3 | 2.0 | 0.8d |
| F | 10 | 30 mM Lactic Acid | 4.5 | 90 mg/mL Trehalose dihydrate, 0.05 mg/mL EDTA, 0.1 mg/mL L-Methionine, 0.5 mg/mL PS20 | Liq | 5.5 | 13.5 | 8.7 | — | 39.1 | — | 1.7 | 12.4 |
| G | 10 | 15 mM Lactic Acid | 4.8 | 45 mg/mL Trehalose dihydrate, 0.5 mg/mL PS20 | Lyo | 5.4 | 5.5 | 5.3 | 6.4 | 38.6 | 40 | 1.7 | 2.2 |
| H | 20 | 30 mM Lactic Acid | 4.8 | 90 mg/mL Trehalose dihydrate, 0.5 mg/mL PS20 | Lyo | 5.8 | 5.5 | 5.6 | 5.4 | 38.5 | 39.5 | 2.0 | 2.0 |
| J | 40 | 30 mM Lactic Acid | 4.8 | 90 mg/mL Trehalose dihydrate, 0.5 mg/mL PS20 | Lyo | 7.3 | 6.4 | 5.7 | 6.2 | 40.4 | 39.3 | 1.7 | 2.2 |
| K | 10 | 30 mM Lactic Acid | 4.8 | 90 mg/mL Trehalose dihydrate, 0.5 mg/mL PS20 | Lyo | 5.4 | 5.2 | 5.2 | 5.1 | 40.2 | 40.3 | 2.0 | 2.1 |
| L | 10 | 30 mM Lactic Acid | 4.8 | 90 mg/mL Trehalose dihydrate, 0.5 mg/mL PS20 | Liq | 5.4 | 13.5 | nc | — | 39.7 | — | 1.7 | 10.9 |

(Liq = Liquid, Lyo = lyophilized)

The invention claimed is:

1. A composition comprising an FGF21 molecule covalently attached to the combining site of an antibody or antigen binding portion thereof via a linker, wherein the FGF21 molecule has a cysteine at position 79, 125 or 129 according of the numbering of SEQ ID NO:1 and wherein the linker is covalently attached to the FGF21 molecule through the thiol group of the cysteine.

2. The composition as claimed in claim 1, wherein residue 129 is cysteine and the linker is covalently attached to the thiol group of cysteine 129.

3. The composition as claimed in claim 1, wherein the linker comprises the formula X—Y—Z; wherein X is a biologically compatible connecting chain including any atom selected from the group consisting of C, H, N, O, P, S, F, Cl, Br, and I, and may comprise a polymer or block co-polymer, and is covalently linked to the linking residue where the linker is linear, Y is an optionally present recognition group comprising at least a ring structure; and Z is an attachment moiety comprising a covalent link to an amino acid side chain in a combining site of the antibody.

4. The composition as claimed in claim 3, wherein Y has the optionally substituted structure:

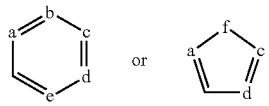

wherein a, b, c, d, and e are independently carbon or nitrogen; f is carbon, nitrogen, oxygen, or sulfur.

5. The composition as claimed in claim 3, wherein Y is phenyl.

6. The composition as claimed in claim 3, wherein Z has the formula

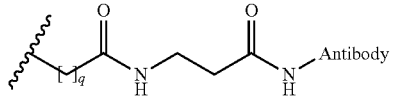

when covalently attached to the antibody, and q=1 or 2.

7. The composition as claimed in claim 3, comprising a formula selected from the group consisting

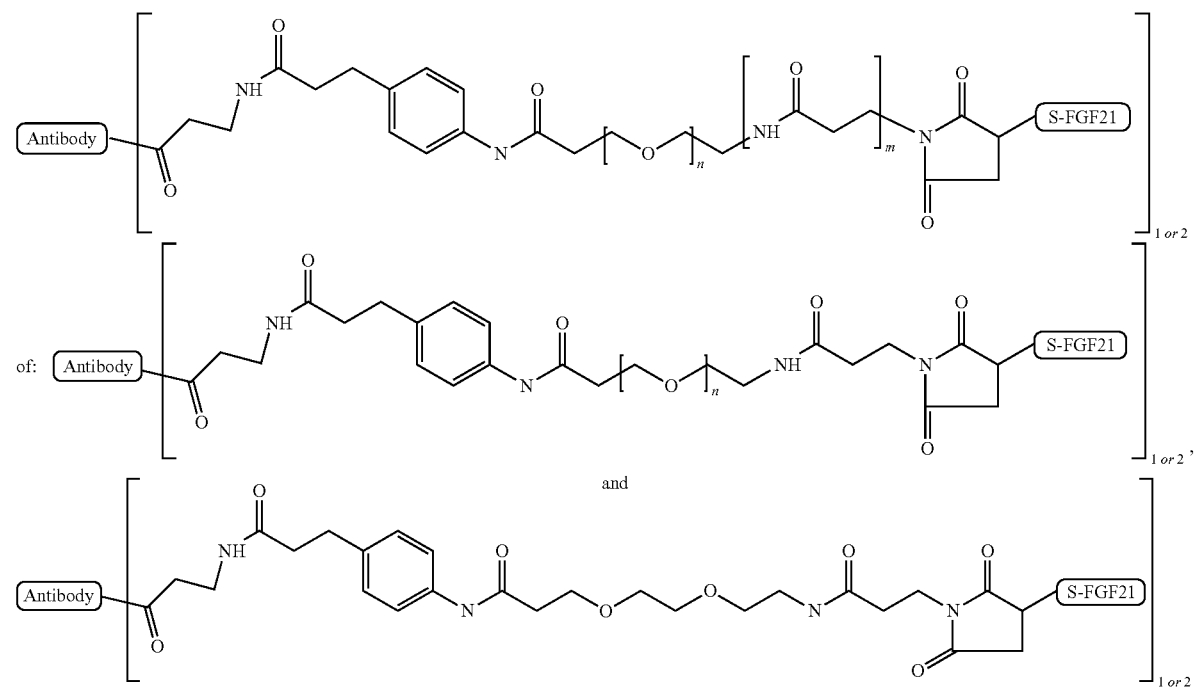

wherein the antibody combining site is covalently linked to the linker, S-FGF21 is the covalent linkage to a thiol-bearing side chain of the cysteine residue, n=1, or 2, 3, 4, 5, 6, 7, 8, 9, or 10; and m is present or absent.

8. The composition as claimed in claim 7, wherein n=1, 2, 3, or 4.

9. The composition as claimed in claim 1, wherein the antibody is a full-length antibody, Fab, Fab', F(ab')2, Fv, dsFv, scFv, VH, VL, diabody, minibody comprising VH and VL domains from h38c2 or m38C2, or full length antibody comprising the VH and VL domains from h38c2 or m38C2 and a constant domain selected from the group consisting of IgG1, IgG2, IgG3, and IgG4, and may be h38C2 IgG1.

10. The composition as claimed in claim 9, wherein the linker is covalently conjugated to the ε-amino group of lysine93 of the heavy chain of the antibody according to Kabat numbering.

11. The composition as claimed in claim 1, wherein the antibody is an aldolase antibody.

12. The composition as claimed in claim 11, wherein the aldolase antibody comprises a VL region comprising SEQ ID NO:27 and a VH region comprising SEQ ID NO:28.

13. The composition as claimed in claim 1, wherein the FGF21 molecule comprises a sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16.

14. The composition as claimed in claim 1, comprising a sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:13.

15. The composition as claimed in claim 1, comprising a sequence selected from the group consisting of SEQ ID NO:8, SEQ ID NO:9, and SEQ ID NO:10.

16. The composition as claimed in claim 1, comprising the formula

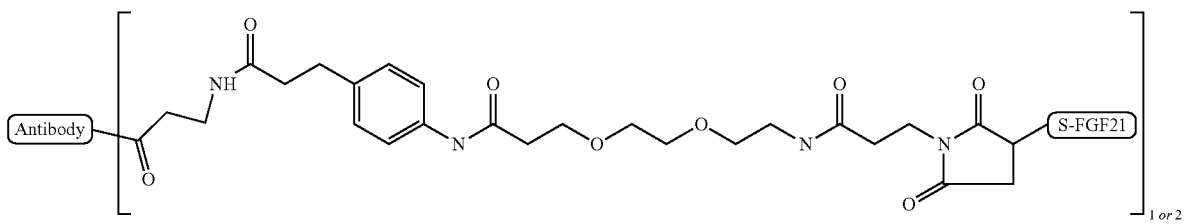

wherein the antibody is linked at the combining site and comprises SEQ ID NO:25 and SEQ ID NO:26, and S-FGF21 is the thiol-bearing side chain of Cys129 of SEQ ID NO: 10.

17. The composition as claimed in claim 1, having at least one of the following characteristics:
   a. a potency of less than about 4 nM in a Glut1 Taqman assay,
   b. a plasma T1/2 following SC injection of at least about 30 hrs in murine models,
   c. a plasma T1/2 following SC injection of at least about 33 hrs in murine models,
   d. a plasma T1/2 following SC injection of at least about 35 hrs in rat models,
   e. a plasma T1/2 following SC injection of at least about 45 hrs in primate models,
   a potency of less than about 3 nM in a Glut1 Taqman assay.

18. The composition as claimed in claim 17, wherein the conjugated protein antibody complex has the formula:

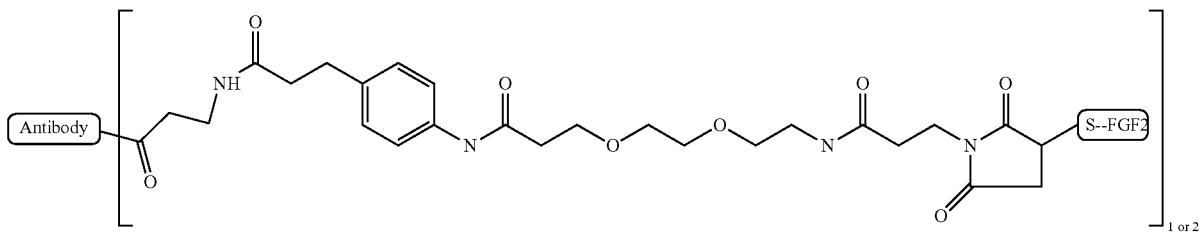

wherein the antibody is linked at a combining site and comprises SEQ ID NO:25 and SEQ ID NO:26, and S-FGF-21 is linked via a thiol-bearing side chain at either Cys 125 from one of SEQ ID NO: 5, SEQ ID NO: 6, or SEQ ID NO:7 or at Cys129 from one of SEQ ID NO: 8, SEQ ID NO: 9, or SEQ ID NO:10.

19. A pharmaceutical composition comprising a therapeutically effective amount of a compound as claimed in claim 1, in combination with a pharmaceutically acceptable carrier.

20. The composition as claimed in claim 1, comprising the formula

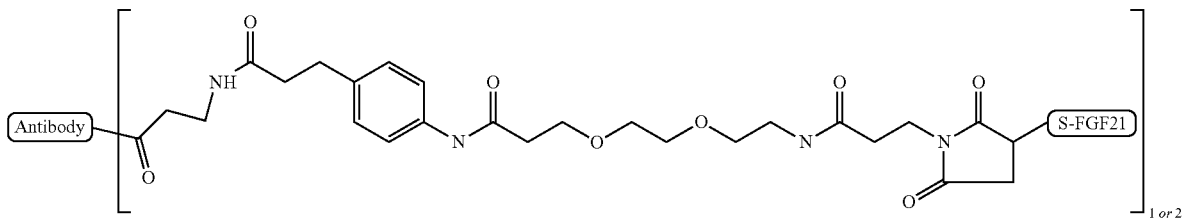

wherein the antibody is linked at a combining site and comprises SEQ ID NO:25 and SEQ ID NO:26, and S-FGF21 is linked via a thiol-bearing side chain at Cys129 from SEQ ID NO:8.

21. The composition as claimed in claim 1, comprising the formula

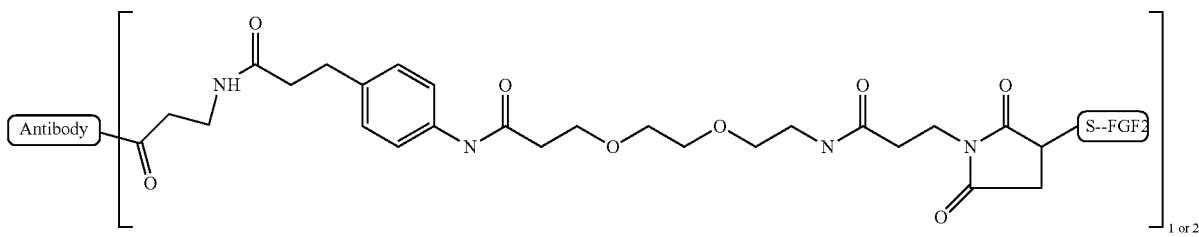

wherein the antibody is linked at a combining site and comprises SEQ ID NO:25 and SEQ ID NO:26, and S-FGF21 is linked via a thiol-bearing side chain at Cys129 from SEQ ID NO:9.

* * * * *

SEQUENCE LISTING

```
<160> NUMBER OF SEQ ID NOS: 33

<210> SEQ ID NO 1
<211> LENGTH: 181
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = H or absent
<220> FEATURE:
<221> NAME/KEY: MISC_FEATURE
<222> LOCATION: (146)..(146)
<223> OTHER INFORMATION: X = L or P

<400> SEQUENCE: 1

Xaa Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30
```

-continued

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Xaa Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 2
<211> LENGTH: 180
<212> TYPE: PRT
<213> ORGANISM: Homo sapiens

<400> SEQUENCE: 2

Pro Ile Pro Asp Ser Ser Pro Leu Leu Gln Phe Gly Gly Gln Val Arg
1               5                  10                  15

Gln Arg Tyr Leu Tyr Thr Asp Asp Ala Gln Gln Thr Glu Ala His Leu
             20                  25                  30

Glu Ile Arg Glu Asp Gly Thr Val Gly Gly Ala Ala Asp Gln Ser Pro
         35                  40                  45

Glu Ser Leu Leu Gln Leu Lys Ala Leu Lys Pro Gly Val Ile Gln Ile
 50                  55                  60

Leu Gly Val Lys Thr Ser Arg Phe Leu Cys Gln Arg Pro Asp Gly Ala
65                  70                  75                  80

Leu Tyr Gly Ser Leu His Phe Asp Pro Glu Ala Cys Ser Phe Arg Glu
                85                  90                  95

Leu Leu Leu Glu Asp Gly Tyr Asn Val Tyr Gln Ser Glu Ala His Gly
            100                 105                 110

Leu Pro Leu His Leu Pro Gly Asn Lys Ser Pro His Arg Asp Pro Ala
        115                 120                 125

Pro Arg Gly Pro Ala Arg Phe Leu Pro Leu Pro Gly Leu Pro Pro Ala
    130                 135                 140

Pro Leu Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
        180

<210> SEQ ID NO 3
<211> LENGTH: 181
<212> TYPE: PRT
<213> ORGANISM: Homo sapiens

```
<220> FEATURE:
<221> NAME/KEY: MISC_FEATURE
<222> LOCATION: (1)..(1)
<223> OTHER INFORMATION: X = H or Absent
<220> FEATURE:
<221> NAME/KEY: MISC_FEATURE
<222> LOCATION: (79)..(79)
<223> OTHER INFORMATION: X = D or C
<220> FEATURE:
<221> NAME/KEY: MISC_FEATURE
<222> LOCATION: (125)..(125)
<223> OTHER INFORMATION: X = H or C
<220> FEATURE:
<221> NAME/KEY: MISC_FEATURE
<222> LOCATION: (129)..(129)
<223> OTHER INFORMATION: X = A or C
<220> FEATURE:
<221> NAME/KEY: MISC_FEATURE
<222> LOCATION: (146)..(146)
<223> OTHER INFORMATION: X = P or L

<400> SEQUENCE: 3

Xaa Pro Ile Pro Asp Ser Ser Pro Leu Leu Gln Phe Gly Gly Gln Val
1               5                   10                  15

Arg Gln Arg Tyr Leu Tyr Thr Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Xaa Gly
65              70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro Xaa Arg Asp Pro
        115                 120                 125

Xaa Pro Arg Gly Pro Ala Arg Phe Leu Pro Leu Pro Gly Leu Pro Pro
130                 135                 140

Ala Xaa Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 4
<211> LENGTH: 181
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = H or Absent
<220> FEATURE:
<221> NAME/KEY: MISC_FEATURE
<222> LOCATION: (125)..(125)
<223> OTHER INFORMATION: X = C or H
<220> FEATURE:
<221> NAME/KEY: MISC_FEATURE
<222> LOCATION: (129)..(129)
<223> OTHER INFORMATION: X = A or C
<220> FEATURE:
<221> NAME/KEY: MISC_FEATURE
<222> LOCATION: (146)..(146)
<223> OTHER INFORMATION: X = L or P
```

-continued

```
<400> SEQUENCE: 4

Xaa Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro Xaa Arg Asp Pro
        115                 120                 125

Xaa Pro Arg Gly Pro Ala Arg Phe Leu Pro Leu Pro Gly Leu Pro Pro
130                 135                 140

Ala Xaa Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 5
<211> LENGTH: 181
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = H or Absent
<220> FEATURE:
<221> NAME/KEY: MISC_FEATURE
<222> LOCATION: (146)..(146)
<223> OTHER INFORMATION: X = L or P

<400> SEQUENCE: 5

Xaa Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro Cys Arg Asp Pro
        115                 120                 125

Ala Pro Arg Gly Pro Ala Arg Phe Leu Pro Leu Pro Gly Leu Pro Pro
```

```
                    130                 135                 140
Ala Xaa Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                    165                 170                 175

Pro Ser Tyr Ala Ser
            180

<210> SEQ ID NO 6
<211> LENGTH: 180
<212> TYPE: PRT
<213> ORGANISM: Homo sapiens

<400> SEQUENCE: 6

Pro Ile Pro Asp Ser Ser Pro Leu Leu Gln Phe Gly Gly Gln Val Arg
1               5                   10                  15

Gln Arg Tyr Leu Tyr Thr Asp Asp Ala Gln Gln Thr Glu Ala His Leu
                20                  25                  30

Glu Ile Arg Glu Asp Gly Thr Val Gly Gly Ala Ala Asp Gln Ser Pro
            35                  40                  45

Glu Ser Leu Leu Gln Leu Lys Ala Leu Lys Pro Gly Val Ile Gln Ile
50                  55                  60

Leu Gly Val Lys Thr Ser Arg Phe Leu Cys Gln Arg Pro Asp Gly Ala
65                  70                  75                  80

Leu Tyr Gly Ser Leu His Phe Asp Pro Glu Ala Cys Ser Phe Arg Glu
                85                  90                  95

Leu Leu Leu Glu Asp Gly Tyr Asn Val Tyr Gln Ser Glu Ala His Gly
            100                 105                 110

Leu Pro Leu His Leu Pro Gly Asn Lys Ser Pro Cys Arg Asp Pro Ala
        115                 120                 125

Pro Arg Gly Pro Ala Arg Phe Leu Pro Leu Pro Gly Leu Pro Pro Ala
130                 135                 140

Leu Pro Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 7
<211> LENGTH: 180
<212> TYPE: PRT
<213> ORGANISM: Homo sapiens

<400> SEQUENCE: 7

Pro Ile Pro Asp Ser Ser Pro Leu Leu Gln Phe Gly Gly Gln Val Arg
1               5                   10                  15

Gln Arg Tyr Leu Tyr Thr Asp Asp Ala Gln Gln Thr Glu Ala His Leu
                20                  25                  30

Glu Ile Arg Glu Asp Gly Thr Val Gly Gly Ala Ala Asp Gln Ser Pro
            35                  40                  45

Glu Ser Leu Leu Gln Leu Lys Ala Leu Lys Pro Gly Val Ile Gln Ile
50                  55                  60

Leu Gly Val Lys Thr Ser Arg Phe Leu Cys Gln Arg Pro Asp Gly Ala
65                  70                  75                  80

Leu Tyr Gly Ser Leu His Phe Asp Pro Glu Ala Cys Ser Phe Arg Glu
                85                  90                  95
```

```
Leu Leu Leu Glu Asp Gly Tyr Asn Val Tyr Gln Ser Glu Ala His Gly
            100                 105                 110

Leu Pro Leu His Leu Pro Gly Asn Lys Ser Pro Cys Arg Asp Pro Ala
            115                 120                 125

Pro Arg Gly Pro Ala Arg Phe Leu Pro Leu Pro Gly Leu Pro Pro Ala
            130                 135                 140

Pro Pro Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 8
<211> LENGTH: 181
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = H or Absent
<220> FEATURE:
<221> NAME/KEY: misc_feature
<222> LOCATION: (146)..(146)
<223> OTHER INFORMATION: Xaa can be any naturally occurring amino acid

<400> SEQUENCE: 8

Xaa Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Cys Pro Arg Gly Pro Ala Arg Phe Leu Pro Leu Pro Gly Leu Pro Pro
            130                 135                 140

Ala Xaa Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 9
<211> LENGTH: 180
<212> TYPE: PRT
<213> ORGANISM: Homo sapiens

<400> SEQUENCE: 9

Pro Ile Pro Asp Ser Ser Pro Leu Leu Gln Phe Gly Gly Gln Val Arg
```

```
                 1               5                  10                 15
Gln Arg Tyr Leu Tyr Thr Asp Asp Ala Gln Gln Thr Glu Ala His Leu
                20                  25                 30

Glu Ile Arg Glu Asp Gly Thr Val Gly Gly Ala Ala Asp Gln Ser Pro
                35                  40                 45

Glu Ser Leu Leu Gln Leu Lys Ala Leu Lys Pro Gly Val Ile Gln Ile
 50                 55                  60

Leu Gly Val Lys Thr Ser Arg Phe Leu Cys Gln Arg Pro Asp Gly Ala
 65                  70                  75                  80

Leu Tyr Gly Ser Leu His Phe Asp Pro Glu Ala Cys Ser Phe Arg Glu
                 85                  90                  95

Leu Leu Leu Glu Asp Gly Tyr Asn Val Tyr Gln Ser Glu Ala His Gly
                100                 105                110

Leu Pro Leu His Leu Pro Gly Asn Lys Ser Pro His Arg Asp Pro Cys
                115                 120                125

Pro Arg Gly Pro Ala Arg Phe Leu Pro Leu Pro Gly Leu Pro Pro Ala
                130                 135                140

Leu Pro Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
                180

<210> SEQ ID NO 10
<211> LENGTH: 180
<212> TYPE: PRT
<213> ORGANISM: Homo sapiens

<400> SEQUENCE: 10

Pro Ile Pro Asp Ser Ser Pro Leu Leu Gln Phe Gly Gly Gln Val Arg
 1               5                  10                 15

Gln Arg Tyr Leu Tyr Thr Asp Asp Ala Gln Gln Thr Glu Ala His Leu
                20                  25                 30

Glu Ile Arg Glu Asp Gly Thr Val Gly Gly Ala Ala Asp Gln Ser Pro
                35                  40                 45

Glu Ser Leu Leu Gln Leu Lys Ala Leu Lys Pro Gly Val Ile Gln Ile
 50                 55                  60

Leu Gly Val Lys Thr Ser Arg Phe Leu Cys Gln Arg Pro Asp Gly Ala
 65                  70                  75                  80

Leu Tyr Gly Ser Leu His Phe Asp Pro Glu Ala Cys Ser Phe Arg Glu
                 85                  90                  95

Leu Leu Leu Glu Asp Gly Tyr Asn Val Tyr Gln Ser Glu Ala His Gly
                100                 105                110

Leu Pro Leu His Leu Pro Gly Asn Lys Ser Pro His Arg Asp Pro Cys
                115                 120                125

Pro Arg Gly Pro Ala Arg Phe Leu Pro Leu Pro Gly Leu Pro Pro Ala
                130                 135                140

Pro Pro Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
                180
```

```
<210> SEQ ID NO 11
<211> LENGTH: 181
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = H or Absent
<220> FEATURE:
<221> NAME/KEY: MISC_FEATURE
<222> LOCATION: (146)..(146)
<223> OTHER INFORMATION: X = P or L

<400> SEQUENCE: 11
```

Xaa Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Cys Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Xaa Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

```
<210> SEQ ID NO 12
<211> LENGTH: 180
<212> TYPE: PRT
<213> ORGANISM: Homo sapiens

<400> SEQUENCE: 12
```

Pro Ile Pro Asp Ser Ser Pro Leu Leu Gln Phe Gly Gly Gln Val Arg
1               5                   10                  15

Gln Arg Tyr Leu Tyr Thr Asp Asp Ala Gln Gln Thr Glu Ala His Leu
            20                  25                  30

Glu Ile Arg Glu Asp Gly Thr Val Gly Gly Ala Ala Asp Gln Ser Pro
        35                  40                  45

Glu Ser Leu Leu Gln Leu Lys Ala Leu Lys Pro Gly Val Ile Gln Ile
    50                  55                  60

Leu Gly Val Lys Thr Ser Arg Phe Leu Cys Gln Arg Pro Cys Gly Ala
65                  70                  75                  80

Leu Tyr Gly Ser Leu His Phe Asp Pro Glu Ala Cys Ser Phe Arg Glu
                85                  90                  95

Leu Leu Leu Glu Asp Gly Tyr Asn Val Tyr Gln Ser Glu Ala His Gly
            100                 105                 110

```
Leu Pro Leu His Leu Pro Gly Asn Lys Ser Pro His Arg Asp Pro Ala
            115                 120                 125

Pro Arg Gly Pro Ala Arg Phe Leu Pro Leu Pro Gly Leu Pro Pro Ala
        130                 135                 140

Pro Pro Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 13
<211> LENGTH: 180
<212> TYPE: PRT
<213> ORGANISM: Homo sapiens

<400> SEQUENCE: 13

Pro Ile Pro Asp Ser Ser Pro Leu Leu Gln Phe Gly Gly Gln Val Arg
1               5                   10                  15

Gln Arg Tyr Leu Tyr Thr Asp Ala Gln Gln Thr Glu Ala His Leu
            20                  25                  30

Glu Ile Arg Glu Asp Gly Thr Val Gly Gly Ala Ala Asp Gln Ser Pro
            35                  40                  45

Glu Ser Leu Leu Gln Leu Lys Ala Leu Lys Pro Gly Val Ile Gln Ile
        50                  55                  60

Leu Gly Val Lys Thr Ser Arg Phe Leu Cys Gln Arg Pro Cys Gly Ala
65                  70                  75                  80

Leu Tyr Gly Ser Leu His Phe Asp Pro Glu Ala Cys Ser Phe Arg Glu
                85                  90                  95

Leu Leu Leu Glu Asp Gly Tyr Asn Val Tyr Gln Ser Glu Ala His Gly
            100                 105                 110

Leu Pro Leu His Leu Pro Gly Asn Lys Ser Pro His Arg Asp Pro Ala
            115                 120                 125

Pro Arg Gly Pro Ala Arg Phe Leu Pro Leu Pro Gly Leu Pro Pro Ala
        130                 135                 140

Leu Pro Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 14
<211> LENGTH: 180
<212> TYPE: PRT
<213> ORGANISM: Homo sapiens

<400> SEQUENCE: 14

Pro Ile Pro Asp Ser Ser Pro Leu Leu Gln Phe Gly Gly Gln Val Arg
1               5                   10                  15

Gln Arg Tyr Leu Tyr Thr Asp Ala Gln Gln Thr Glu Ala His Leu
            20                  25                  30

Glu Ile Arg Glu Asp Gly Thr Val Gly Gly Ala Ala Asp Gln Ser Pro
            35                  40                  45

Glu Ser Leu Leu Gln Leu Lys Ala Leu Lys Pro Gly Val Ile Gln Ile
        50                  55                  60

Leu Gly Val Lys Thr Ser Arg Phe Leu Cys Gln Arg Pro Asp Gly Ala
```

```
                65                  70                  75                  80
Leu Tyr Gly Ser Cys His Phe Asp Pro Glu Ala Cys Ser Phe Arg Glu
                    85                  90                  95

Leu Leu Leu Glu Asp Gly Tyr Asn Val Tyr Gln Ser Glu Ala His Gly
                100                 105                 110

Leu Pro Leu His Leu Pro Gly Asn Lys Ser Pro His Arg Asp Pro Ala
            115                 120                 125

Pro Arg Gly Pro Ala Arg Phe Leu Pro Leu Pro Gly Leu Pro Pro Ala
        130                 135                 140

Pro Leu Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 15
<211> LENGTH: 180
<212> TYPE: PRT
<213> ORGANISM: Homo sapiens

<400> SEQUENCE: 15

Pro Ile Pro Asp Ser Ser Pro Leu Leu Gln Phe Gly Gly Gln Val Arg
1               5                   10                  15

Gln Arg Tyr Leu Tyr Thr Asp Ala Gln Gln Thr Glu Ala His Leu
            20                  25                  30

Glu Ile Arg Glu Asp Gly Cys Val Gly Gly Ala Ala Asp Gln Ser Pro
        35                  40                  45

Glu Ser Leu Leu Gln Leu Lys Ala Leu Lys Pro Gly Val Ile Gln Ile
    50                  55                  60

Leu Gly Val Lys Thr Ser Arg Phe Leu Cys Gln Arg Pro Asp Gly Ala
65                  70                  75                  80

Leu Tyr Gly Ser Leu His Phe Asp Pro Glu Ala Cys Ser Phe Arg Glu
                    85                  90                  95

Leu Leu Leu Glu Asp Gly Tyr Asn Val Tyr Gln Ser Glu Ala His Gly
                100                 105                 110

Leu Pro Leu His Leu Pro Gly Asn Lys Ser Pro His Arg Asp Pro Ala
            115                 120                 125

Pro Arg Gly Pro Ala Arg Phe Leu Pro Leu Pro Gly Leu Pro Pro Ala
        130                 135                 140

Pro Leu Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 16
<211> LENGTH: 181
<212> TYPE: PRT
<213> ORGANISM: Homo sapiens

<400> SEQUENCE: 16

Cys Pro Ile Pro Asp Ser Ser Pro Leu Leu Gln Phe Gly Gly Gln Val
1               5                   10                  15

Arg Gln Arg Tyr Leu Tyr Thr Asp Ala Gln Gln Thr Glu Ala His
            20                  25                  30
```

```
Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 17
<211> LENGTH: 181
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X = H or Absent
<220> FEATURE:
<221> NAME/KEY: MISC_FEATURE
<222> LOCATION: (56)..(56)
<223> OTHER INFORMATION: X = K or R
<220> FEATURE:
<221> NAME/KEY: MISC_FEATURE
<222> LOCATION: (59)..(59)
<223> OTHER INFORMATION: X = K or R
<220> FEATURE:
<221> NAME/KEY: MISC_FEATURE
<222> LOCATION: (122)..(122)
<223> OTHER INFORMATION: X = K or R
<220> FEATURE:
<221> NAME/KEY: MISC_FEATURE
<222> LOCATION: (146)..(146)
<223> OTHER INFORMATION: X = L or P

<400> SEQUENCE: 17

Xaa Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Xaa Ala Leu Xaa Pro Gly Val Ile Gln
 50                  55                  60

Ile Leu Gly Val Arg Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110
```

```
Gly Leu Pro Leu His Leu Pro Gly Asn Xaa Ser Pro His Arg Asp Pro
        115                 120                 125

Ala Pro Arg Gly Pro Ala Arg Phe Leu Pro Leu Pro Gly Leu Pro Pro
130                 135                 140

Ala Xaa Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 18
<211> LENGTH: 180
<212> TYPE: PRT
<213> ORGANISM: Homo sapiens

<400> SEQUENCE: 18

Pro Ile Pro Asp Ser Ser Pro Leu Leu Gln Phe Gly Gly Gln Val Arg
1               5                   10                  15

Gln Arg Tyr Leu Tyr Thr Asp Ala Gln Gln Thr Glu Ala His Leu
        20                  25                  30

Glu Ile Arg Glu Asp Gly Thr Val Gly Gly Ala Ala Asp Gln Ser Pro
        35                  40                  45

Glu Ser Leu Leu Gln Leu Lys Ala Leu Arg Pro Gly Val Ile Gln Ile
50                  55                  60

Leu Gly Val Arg Thr Ser Arg Phe Leu Cys Gln Arg Pro Asp Gly Ala
65                  70                  75                  80

Leu Tyr Gly Ser Leu His Phe Asp Pro Glu Ala Cys Ser Phe Arg Glu
                85                  90                  95

Leu Leu Leu Glu Asp Gly Tyr Asn Val Tyr Gln Ser Glu Ala His Gly
            100                 105                 110

Leu Pro Leu His Leu Pro Gly Asn Arg Ser Pro His Arg Asp Pro Ala
        115                 120                 125

Pro Arg Gly Pro Ala Arg Phe Leu Pro Leu Pro Gly Leu Pro Pro Ala
130                 135                 140

Pro Leu Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 19
<211> LENGTH: 180
<212> TYPE: PRT
<213> ORGANISM: Homo sapiens

<400> SEQUENCE: 19

Pro Ile Pro Asp Ser Ser Pro Leu Leu Gln Phe Gly Gly Gln Val Arg
1               5                   10                  15

Gln Arg Tyr Leu Tyr Thr Asp Ala Gln Gln Thr Glu Ala His Leu
        20                  25                  30

Glu Ile Arg Glu Asp Gly Thr Val Gly Gly Ala Ala Asp Gln Ser Pro
        35                  40                  45

Glu Ser Leu Leu Gln Leu Arg Ala Leu Lys Pro Gly Val Ile Gln Ile
50                  55                  60

Leu Gly Val Arg Thr Ser Arg Phe Leu Cys Gln Arg Pro Asp Gly Ala
```

```
                65                  70                  75                  80
Leu Tyr Gly Ser Leu His Phe Asp Pro Glu Ala Cys Ser Phe Arg Glu
                85                  90                  95

Leu Leu Leu Glu Asp Gly Tyr Asn Val Tyr Gln Ser Glu Ala His Gly
            100                 105                 110

Leu Pro Leu His Leu Pro Gly Asn Arg Ser Pro His Arg Asp Pro Ala
            115                 120                 125

Pro Arg Gly Pro Ala Arg Phe Leu Pro Leu Pro Gly Leu Pro Pro Ala
        130                 135                 140

Pro Leu Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 20
<211> LENGTH: 180
<212> TYPE: PRT
<213> ORGANISM: Homo sapiens

<400> SEQUENCE: 20

Pro Ile Pro Asp Ser Ser Pro Leu Leu Gln Phe Gly Gly Gln Val Arg
1               5                   10                  15

Gln Arg Tyr Leu Tyr Thr Asp Asp Ala Gln Gln Thr Glu Ala His Leu
            20                  25                  30

Glu Ile Arg Glu Asp Gly Thr Val Gly Gly Ala Ala Asp Gln Ser Pro
        35                  40                  45

Glu Ser Leu Leu Gln Leu Arg Ala Leu Arg Pro Gly Val Ile Gln Ile
    50                  55                  60

Leu Gly Val Lys Thr Ser Arg Phe Leu Cys Gln Arg Pro Asp Gly Ala
65                  70                  75                  80

Leu Tyr Gly Ser Leu His Phe Asp Pro Glu Ala Cys Ser Phe Arg Glu
                85                  90                  95

Leu Leu Leu Glu Asp Gly Tyr Asn Val Tyr Gln Ser Glu Ala His Gly
            100                 105                 110

Leu Pro Leu His Leu Pro Gly Asn Arg Ser Pro His Arg Asp Pro Ala
            115                 120                 125

Pro Arg Gly Pro Ala Arg Phe Leu Pro Leu Pro Gly Leu Pro Pro Ala
        130                 135                 140

Pro Leu Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 21
<211> LENGTH: 180
<212> TYPE: PRT
<213> ORGANISM: Homo sapiens

<400> SEQUENCE: 21

Pro Ile Pro Asp Ser Ser Pro Leu Leu Gln Phe Gly Gly Gln Val Arg
1               5                   10                  15

Gln Arg Tyr Leu Tyr Thr Asp Asp Ala Gln Gln Thr Glu Ala His Leu
            20                  25                  30
```

```
Glu Ile Arg Glu Asp Gly Thr Val Gly Gly Ala Ala Asp Gln Ser Pro
        35                  40                  45

Glu Ser Leu Leu Gln Leu Arg Ala Leu Arg Pro Gly Val Ile Gln Ile
 50                  55                  60

Leu Gly Val Arg Thr Ser Arg Phe Leu Cys Gln Arg Pro Asp Gly Ala
 65                  70                  75                  80

Leu Tyr Gly Ser Leu His Phe Asp Pro Glu Ala Cys Ser Phe Arg Glu
                 85                  90                  95

Leu Leu Leu Glu Asp Gly Tyr Asn Val Tyr Gln Ser Glu Ala His Gly
                100                 105                 110

Leu Pro Leu His Leu Pro Gly Asn Lys Ser Pro His Arg Asp Pro Ala
                115                 120                 125

Pro Arg Gly Pro Ala Arg Phe Leu Pro Leu Pro Gly Leu Pro Pro Ala
130                 135                 140

Pro Leu Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 22
<211> LENGTH: 180
<212> TYPE: PRT
<213> ORGANISM: Homo sapiens

<400> SEQUENCE: 22

Pro Ile Pro Asp Ser Ser Pro Leu Leu Gln Phe Gly Gly Gln Val Arg
 1               5                  10                  15

Gln Arg Tyr Leu Tyr Thr Asp Asp Ala Gln Gln Thr Glu Ala His Leu
                20                  25                  30

Glu Ile Arg Glu Asp Gly Thr Val Gly Gly Ala Ala Asp Gln Ser Pro
        35                  40                  45

Glu Ser Leu Leu Gln Leu Arg Ala Leu Arg Pro Gly Val Ile Gln Ile
 50                  55                  60

Leu Gly Val Arg Thr Ser Arg Phe Leu Cys Gln Arg Pro Asp Gly Ala
 65                  70                  75                  80

Leu Tyr Gly Ser Leu His Phe Asp Pro Glu Ala Cys Ser Phe Arg Glu
                 85                  90                  95

Leu Leu Leu Glu Asp Gly Tyr Asn Val Tyr Gln Ser Glu Ala His Gly
                100                 105                 110

Leu Pro Leu His Leu Pro Gly Asn Arg Ser Pro His Arg Asp Pro Ala
                115                 120                 125

Pro Arg Gly Pro Ala Arg Phe Leu Pro Leu Pro Gly Leu Pro Pro Ala
130                 135                 140

Pro Leu Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 23
<211> LENGTH: 181
<212> TYPE: PRT
<213> ORGANISM: Homo sapiens
```

```
<400> SEQUENCE: 23

Lys Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Arg Ala Leu Arg Pro Gly Val Ile Gln
    50                  55                  60

Ile Leu Gly Val Arg Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Arg Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 24
<211> LENGTH: 180
<212> TYPE: PRT
<213> ORGANISM: Homo sapiens

<400> SEQUENCE: 24

Pro Ile Pro Asp Ser Ser Pro Leu Leu Gln Phe Gly Gly Gln Val Arg
1               5                   10                  15

Gln Arg Tyr Leu Tyr Thr Asp Asp Ala Gln Gln Thr Glu Ala His Leu
            20                  25                  30

Glu Ile Arg Glu Asp Gly Thr Val Gly Gly Ala Ala Asp Gln Ser Pro
        35                  40                  45

Glu Ser Leu Leu Gln Leu Arg Ala Leu Arg Pro Gly Val Ile Gln Ile
    50                  55                  60

Leu Gly Val Arg Thr Ser Arg Phe Leu Cys Gln Arg Pro Asp Gly Ala
65                  70                  75                  80

Leu Tyr Gly Ser Leu His Phe Asp Pro Glu Ala Cys Ser Phe Arg Glu
                85                  90                  95

Leu Leu Leu Glu Asp Gly Tyr Asn Val Tyr Gln Ser Glu Ala His Gly
            100                 105                 110

Leu Pro Leu His Leu Pro Gly Asn Arg Ser Pro His Arg Asp Pro Ala
        115                 120                 125

Pro Arg Gly Pro Ala Arg Phe Leu Pro Leu Pro Gly Leu Pro Pro Ala
    130                 135                 140

Pro Leu Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175
```

Ser Tyr Ala Lys
            180

<210> SEQ ID NO 25
<211> LENGTH: 219
<212> TYPE: PRT
<213> ORGANISM: Homo sapiens

<400> SEQUENCE: 25

Glu Leu Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Phe Cys Ser Gln Gly
                85                  90                  95

Thr His Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 26
<211> LENGTH: 448
<212> TYPE: PRT
<213> ORGANISM: Homo sapiens

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

Ser Glu Ile Arg Leu Arg Ser Asp Asn Tyr Ala Thr His Tyr Ala Glu
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Gly Ile Tyr
                85                  90                  95

Tyr Cys Lys Thr Tyr Phe Tyr Ser Phe Ser Tyr Trp Gly Gln Gly Thr

```
                    100                 105                 110
Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 27
<211> LENGTH: 112
<212> TYPE: PRT
<213> ORGANISM: Homo sapiens

<400> SEQUENCE: 27

Glu Leu Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
```

```
                35                  40                  45
Pro Lys Leu Leu Ile Tyr Lys Val Ser Asn Arg Phe Ser Gly Val Pro
 50                  55                  60
Ser Arg Phe Ser Gly Ser Gly Ser Gly Thr Asp Phe Thr Leu Thr Ile
 65                  70                  75                  80
Ser Ser Leu Gln Pro Glu Asp Phe Ala Val Tyr Phe Cys Ser Gln Gly
             85                  90                  95
Thr His Leu Pro Tyr Thr Phe Gly Gly Gly Thr Lys Val Glu Ile Lys
            100                 105                 110

<210> SEQ ID NO 28
<211> LENGTH: 118
<212> TYPE: PRT
<213> ORGANISM: Homo sapiens

<400> SEQUENCE: 28

Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Asn Tyr
             20                  25                  30
Trp Met Ser Trp Val Arg Gln Ser Pro Glu Lys Gly Leu Glu Trp Val
         35                  40                  45
Ser Glu Ile Arg Leu Arg Ser Asp Asn Tyr Ala Thr His Tyr Ala Glu
 50                  55                  60
Ser Val Lys Gly Arg Phe Thr Ile Ser Arg Asp Asn Ser Lys Asn Thr
 65                  70                  75                  80
Leu Tyr Leu Gln Met Asn Ser Leu Arg Ala Glu Asp Thr Gly Ile Tyr
             85                  90                  95
Tyr Cys Lys Thr Tyr Phe Tyr Ser Phe Ser Tyr Trp Gly Gln Gly Thr
            100                 105                 110
Leu Val Thr Val Ser Ser
            115

<210> SEQ ID NO 29
<211> LENGTH: 112
<212> TYPE: PRT
<213> ORGANISM: Mus musculus

<400> SEQUENCE: 29

Asp Val Val Met Thr Gln Thr Pro Leu Ser Leu Pro Val Arg Leu Gly
 1               5                  10                  15
Asp Gln Ala Ser Ile Ser Cys Arg Ser Ser Gln Ser Leu Leu His Thr
             20                  25                  30
Tyr Gly Ser Pro Tyr Leu Asn Trp Tyr Leu Gln Lys Pro Gly Gln Ser
         35                  40                  45
Pro Lys Leu Leu Ile Tyr Lys Val Ser Asn Arg Phe Ser Gly Val Pro
 50                  55                  60
Asp Arg Phe Ser Gly Ser Gly Ser Gly Thr Asp Phe Thr Leu Arg Ile
 65                  70                  75                  80
Ser Arg Val Glu Ala Glu Asp Leu Gly Val Tyr Phe Cys Ser Gln Gly
             85                  90                  95
Thr His Leu Pro Tyr Thr Phe Gly Gly Gly Thr Lys Leu Glu Ile Lys
            100                 105                 110

<210> SEQ ID NO 30
<211> LENGTH: 118
<212> TYPE: PRT
<213> ORGANISM: Mus musculus
```

<400> SEQUENCE: 30

Glu Val Lys Leu Val Glu Ser Gly Gly Gly Leu Val Gln Pro Gly Gly
1               5                   10                  15

Thr Met Lys Leu Ser Cys Glu Ile Ser Gly Leu Thr Phe Arg Asn Tyr
            20                  25                  30

Trp Met Ser Trp Val Arg Gln Ser Pro Glu Lys Gly Leu Glu Trp Val
        35                  40                  45

Ala Glu Ile Arg Leu Arg Ser Asp Asn Tyr Ala Thr His Tyr Ala Glu
    50                  55                  60

Ser Val Lys Gly Lys Phe Thr Ile Ser Arg Asp Asp Ser Lys Ser Arg
65                  70                  75                  80

Leu Tyr Leu Gln Met Asn Ser Leu Arg Thr Glu Asp Thr Gly Ile Tyr
                85                  90                  95

Tyr Cys Lys Tyr Tyr Phe Tyr Ser Phe Ser Tyr Trp Gly Gln Gly Thr
            100                 105                 110

Leu Val Thr Val Ser Ala
        115

<210> SEQ ID NO 31
<211> LENGTH: 15
<212> TYPE: PRT
<213> ORGANISM: Artificial Sequence
<220> FEATURE:
<223> OTHER INFORMATION: Amino Acid Linker

<400> SEQUENCE: 31

Gly Gly Gly Gly Ser Gly Gly Gly Gly Ser Gly Gly Gly Gly Ser
1               5                   10                  15

<210> SEQ ID NO 32
<211> LENGTH: 28
<212> TYPE: PRT
<213> ORGANISM: Homo sapiens

<400> SEQUENCE: 32

Met Asn Ser Asn Glu Thr Gly Phe Glu His Ser Gly Leu Trp Val Ser
1               5                   10                  15

Val Leu Ala Gly Leu Leu Gly Ala Cys Gln Ala
            20                  25

<210> SEQ ID NO 33
<211> LENGTH: 209
<212> TYPE: PRT
<213> ORGANISM: Homo sapiens

<400> SEQUENCE: 33

Met Asn Ser Asn Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

```
Ser Leu His Phe Asp Pro Glu Ala Cys Ser Phe Arg Glu Leu Leu Leu
        115             120             125

Glu Asp Gly Tyr Asn Val Tyr Gln Ser Glu Ala His Gly Leu Pro Leu
        130             135             140

His Leu Pro Gly Asn Lys Ser Pro His Arg Asp Pro Ala Pro Arg Gly
145             150             155             160

Pro Ala Arg Phe Leu Pro Leu Pro Gly Leu Pro Pro Ala Leu Pro Glu
                165             170             175

Pro Pro Gly Ile Leu Ala Pro Gln Pro Pro Asp Val Gly Ser Ser Asp
            180             185             190

Pro Leu Ser Met Val Gly Pro Ser Gln Gly Arg Ser Pro Ser Tyr Ala
        195             200             205

Ser
```